(12) United States Patent
Stapleton et al.

(10) Patent No.: US 7,951,531 B2
(45) Date of Patent: May 31, 2011

(54) FLAVIVIRUS NS5A PROTEINS FOR THE TREATMENT OF HIV

(75) Inventors: Jack T. Stapleton, Iowa City, IA (US); Jinhua Xiang, Iowa City, IA (US); Qing Chang, Iowa City, IA (US); James McLinden, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 562 days.

(21) Appl. No.: 11/345,662

(22) Filed: Feb. 1, 2006

(65) Prior Publication Data

US 2007/0036825 A1 Feb. 15, 2007

Related U.S. Application Data

(60) Provisional application No. 60/653,823, filed on Feb. 17, 2005.

(51) Int. Cl.
*C12Q 1/70* (2006.01)
*A61K 39/21* (2006.01)
*A61K 39/29* (2006.01)

(52) U.S. Cl. .................. 435/5; 424/208.1; 424/228.1

(58) Field of Classification Search .................. None
See application file for complete search history.

(56) References Cited

U.S. PATENT DOCUMENTS

| | | | |
|---|---|---|---|
| 5,441,936 A | 8/1995 | Houghten et al. | 514/16 |
| 5,766,840 A | 6/1998 | Kim et al. | 435/5 |
| 5,824,507 A | 10/1998 | Kim et al. | 435/69.3 |
| 5,849,532 A | 12/1998 | Kim et al. | 435/69.3 |
| 5,856,134 A | 1/1999 | Kim et al. | 435/69.3 |
| 5,874,563 A | 2/1999 | Kim et al. | 536/23.72 |
| 5,981,172 A | 11/1999 | Simons et al. | 435/5 |
| 6,020,199 A | 2/2000 | Schmolke et al. | 435/399 |
| 6,051,374 A | 4/2000 | Simons et al. | 435/5 |
| 6,156,495 A | 12/2000 | Pilot-Matias et al. | 435/5 |
| 6,451,578 B1 | 9/2002 | Simons et al. | 435/235.1 |
| 6,558,898 B1 | 5/2003 | Simons et al. | 435/5 |
| 6,586,568 B1 | 7/2003 | Simons et al. | 530/300 |
| 6,720,166 B2 | 4/2004 | Simons et al. | 435/69.1 |
| 2004/0151735 A1* | 8/2004 | Maertens et al. | 424/189.1 |
| 2004/0247615 A1* | 12/2004 | Emini et al. | 424/189.1 |
| 2005/0013828 A1 | 1/2005 | George et al. | 424/189.1 |

FOREIGN PATENT DOCUMENTS

| | | |
|---|---|---|
| EP | 0747482 | 11/1996 |
| WO | WO 2004/037202 | 6/2004 |
| WO | WO 2004/108159 | 12/2004 |

OTHER PUBLICATIONS

Chang et al., Journal of General Virology, 2007, 88:3341-3346.*
Desrosiers, R., Nature Medicine, Mar. 2004, 10(3):221-223.*
Feinberg et al., Nature Medicine, Mar. 2002, 8(3):207-210.*
Henkel, J., FDA Consumer, Jul.-Aug. 1999, 33(4), 10 pages.*
Gale et al, "Antiapoptotic and oncogenic potentials of hepatitis C virus are linked to interferon resistance by viral repression of the PKR protein kinase," *J. Virol.*, 73:6506-6516, 1999.
George et al., "Clinical isolates of GB virus type C vary in their ability to persist and replicate in peripheral blood mononuclear cell cultures," *Virology*, 316:191-201, 2003.
Lefrère et al, "Prevalence of GB virus type C/hepatitis G virus RNA and of anti-E2 in individuals at high or low risk for blood-borne or sexually transmitted viruses: evidence of sexual and parenteral transmission," *Transfusion*, 39:83, 1999.
Natterman et al., "Regulation of CC chemokine receptor 5 in hepatitis G virus infection," *AIDS*, 17:1457-1462, 2003.
Sabin et al., "Effect of Coinfection with Hepatitis G Virus on HIV Disease Progression in Hemophilic Men," *Journal of Acquired Immune Deficiency Syndromes & Human Retrovirus*, 19(5):546-547, 1998.
Stapleton et al., "GB virus C: A beneficial infection?" *J. Clin. Microbiol.*, 42:3915-3919, 2004.
Toyoda et al., "Effect of GB Virus C/Hepatitis G Virus Coinfection on the Course of HIV Infection in Hemophilia Patients in Japan," *Journal of Acquires Immune Deficiency Syndrome & Human Retrovirus*, 17(3):209-213, 1998.
Xiang et al., "Effect of coinfection with GB virus C (hepatitis G virus) on survival among patients with HIV infection," *N. Engl J Med*, 345:707-714, 2001.
Xiang et al., "Full-length GB virus C (Hepatitis G Virus) RNA transcripts are infectious in primary CD4 positive T cells," *J Virol*, 74:9125-9133, 2000.
Xiang et al., "GB virus type C NS5A sequence polymorphisms: Association with interferon susceptibility and inhibition of PKR-mediated eIF-2a phosphorylation," *J Interferon Cytokine Res*, 25:261-270, 2005.
Xiang et al., "Inhibition of HIV-1 replication by GB virus C infection through increases in RANTES, MIP-1alpha, MIP-1beta, and SDF-1," *Lancet*, 363: 2040-2046, 2004.
Jones et al., "Inhibition of influenza virus infection by a novel antiviral peptide that targets viral attachment to cells," *J. Virol.*, 80:11960-11967, 2006.
Pan et al., "Antiviral properties of milk proteins and peptides," *Int. Dairy Journal*, 16:1252-1261, 2006.

* cited by examiner

*Primary Examiner* — Stacy B Chen
(74) *Attorney, Agent, or Firm* — Fulbright & Jaworski

(57) ABSTRACT

GB virus C (GBV-C or hepatitis G virus) is a flavivirus that frequently leads to chronic viremia in humans. The invention provides compositions and methods involving a-GBV-C NS5A peptide or polypeptide for inhibiting and treating HIV infections.

6 Claims, 21 Drawing Sheets

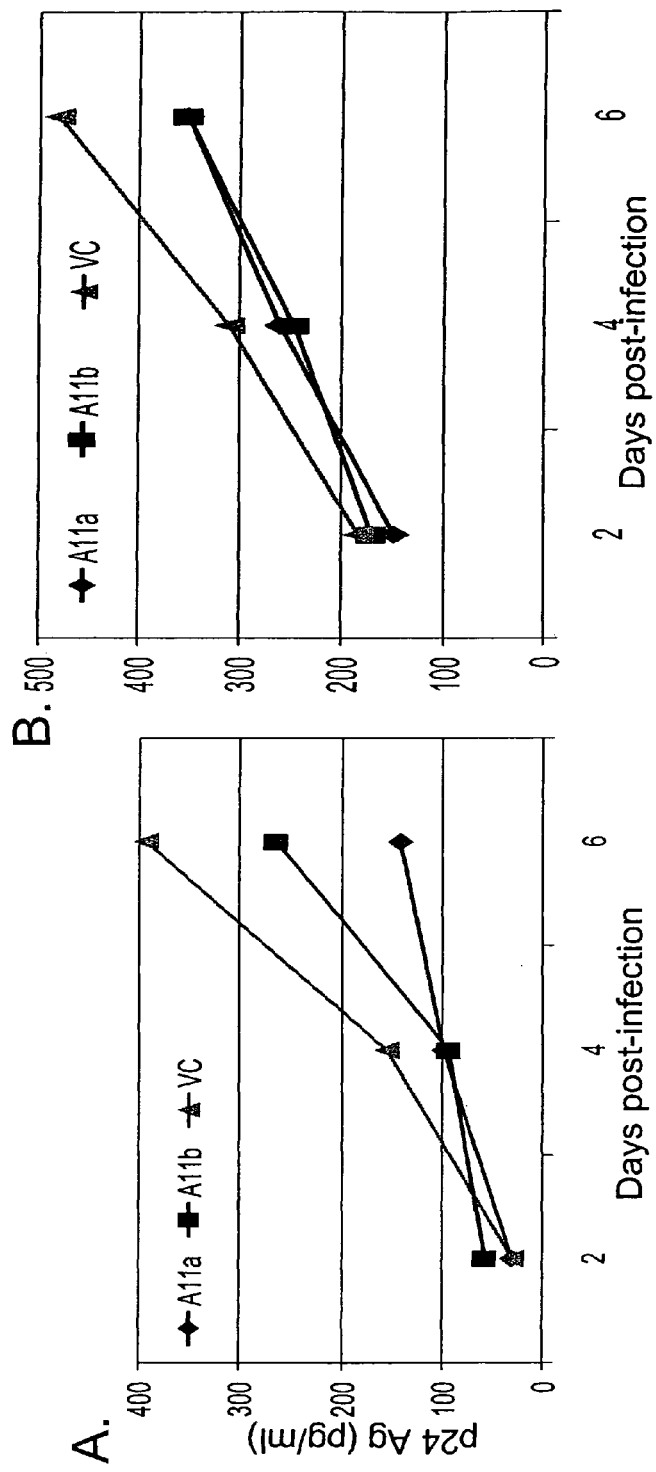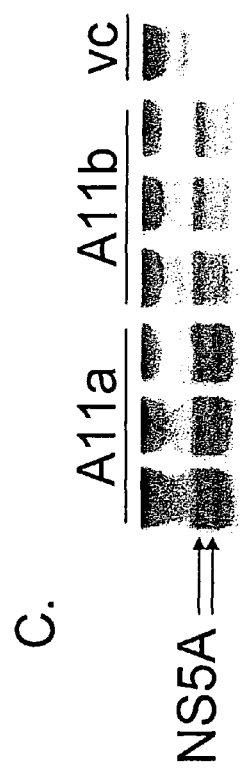
FIG. 2A-C

NS5A Inhibits HIV MN (X4) Clade B

Legend: VC-GFP, IFN-R, IFN-S-GFP, IFN-R-GFP

Y-axis: HIV p24 Antigen Release (0–5000)
X-axis: D3, D4, D5, D6

FIG. 11A

NS5A (414 aa) – IFN-R
NS5A (414 aa) – IFN-R + GFP
NS5A (414 aa) – IFN-S + GFP
NS5A (363 aa) – IFN-R + GFP
NS5A (250 aa) – IFN-R + GFP
NS5A (167 aa) – IFN-R + GFP
5A (123 aa) – R
NS5A (314 aa) – IFN-S + GFP
NS5A (123-363 aa) – IFN-R + GFP
167-250 – R

| | | |
|---|---|---|
| IFN-sens. | VGYVWDLWEWIMRQVRMVMARLRALCPVVSLPLMWHCGEGWSGEWLLDGHVESRCLCGCVITGDVLNGQLKEPVYSTKLCR | 80 |
| IFN-res-1 | ---------------------------------------------------------------------------- | 80 |
| IFN-res-2 | ---------------------------------------------------------------------------- | 80 |
| IFN-res-3 | ---------------------------------------------------------------------------- | 80 |
| IFN-sens. | HYWMETVPVNMLGY

SEQUENCE LISTING

<160> NUMBER OF SEQ ID NOS: 9

<210> SEQ ID NO 1
<211> LENGTH: 9377
<212> TYPE: DNA
<213> ORGANISM: Hepatitis GB virus C
<220> FEATURE:
<221> NAME/KEY: CDS
<222> LOCATION: (534)..(9065)

-continued

<400> SEQUENCE: 1

```
cccccccccc ggcactgggt gcaagcccca gaaaccgacg cctactgaag tagacgtaat      60
ggccccgcgc cgaaccggcg accggccaaa aggtggtgga tgggtgatga cagggttggt     120
aggtcgtaaa tcccggtcat cctggtagcc actataggtg ggtcttaagg ggaggctacg     180
gtccctcttg cgcatatgga ggaaaagcgc acggtccaca ggtgttggtc ctaccggtgt     240
aataaggacc cggcgctagg cacgccgtta aaccgagccc gttactcccc tgggcaaacg     300
acgcccacgt acgtccacg tcgcccttca atgtctctct tgaccaatag gcgtagccgg      360
cgagttgaca aggaccagtg ggggccgggc gggaggggga aggacccca ccgctgccct      420 tcccggggag gcgggaaatg catggggcca cccagctccg cggcggccta cagccgggt      480 agcccaagaa ccttcgggtg agggcgggtg gcatttcttt tcctataccg atc atg       536
                                                              Met
                                                               1
```

```
gca gtc ctt ctg ctc cta ctc gtg gtg gag gcc ggg gct att tta gcc      584
Ala Val Leu Leu Leu Leu Leu Val Val Glu Ala Gly Ala Ile Leu Ala
         5                  10                  15 ccg gcc acc cat gct tgt agc gcg aaa ggg caa tat tts ctc aca aac      632
Pro Ala Thr His Ala Cys Ser Ala Lys Gly Gln Tyr Xaa Leu Thr Asn
     20                  25                  30 tgt tgc gcc ctg gag gac ata ggc ttc tgc ctg gag ggc gga tgc ctg      680
Cys Cys Ala Leu Glu Asp Ile Gly Phe Cys Leu Glu Gly Gly Cys Leu
 35                  40                  45 gtg gct ctg ggg tgc acc att tgc acc gac cgc tgc tgg cca ctg tat      728
Val Ala Leu Gly Cys Thr Ile Cys Thr Asp Arg Cys Trp Pro Leu Tyr
 50                  55                  60                  65 cag gcg ggt ttg gcc gtg cgg ccc ggc aag tcc gcc gcc cag ttg gtg      776
Gln Ala Gly Leu Ala Val Arg Pro Gly Lys Ser Ala Ala Gln Leu Val
             70                  75                  80 ggg gaa ctc ggt agt ctc tac ggg ccc ttg tcg gtc tcg gct tat gtg      824
Gly Glu Leu Gly Ser Leu Tyr Gly Pro Leu Ser Val Ser Ala Tyr Val
         85                  90                  95 gcc ggg atc ctg ggg ctt ggg gag gtc tac tcg ggg gtc ctc acc gtc      872
Ala Gly Ile Leu Gly Leu Gly Glu Val Tyr Ser Gly Val Leu Thr Val
    100                 105                 110 ggg gtg gcg ttg acg cgc agg gtc tac ccg gtc ccg aac ctg acg tgt      920
Gly Val Ala Leu Thr Arg Arg Val Tyr Pro Val Pro Asn Leu Thr Cys
115                 120                 125 gca gta gag tgt gag ttg aag tgg gaa agt gag ttt tgg aga tgg act      968
Ala Val Glu Cys Glu Leu Lys Trp Glu Ser Glu Phe Trp Arg Trp Thr
130                 135                 140                 145 gaa cag ctg gcc tca aac tac tgg att ctg gaa tac ctc tgg aag gtg     1016
Glu Gln Leu Ala Ser Asn Tyr Trp Ile Leu Glu Tyr Leu Trp Lys Val
             150                 155                 160 cct ttc gac ttt tgg cgg gga gtg atg agc ctt act cct ctc ttg gtg     1064
Pro Phe Asp Phe Trp Arg Gly Val Met Ser Leu Thr Pro Leu Leu Val
         165                 170                 175 tgc gtg gcg gcc ctc ctc ctg ctg gag cag cgt att gtc atg gtc ttc     1112
Cys Val Ala Ala Leu Leu Leu Leu Glu Gln Arg Ile Val Met Val Phe
    180                 185                 190 ctc ctg gtc act atg gcg ggc atg tcg caa ggc gcg ccc gcc tca gtg     1160
Leu Leu Val Thr Met Ala Gly Met Ser Gln Gly Ala Pro Ala Ser Val
195                 200                 205 ttg ggg tca cgg cct ttc gag gcc ggg ttg act tgg cag tct tgt tct     1208
Leu Gly Ser Arg Pro Phe Glu Ala Gly Leu Thr Trp Gln Ser Cys Ser
210                 215                 220                 225 tgc agg tcg aac ggg tcc cgc gtg ccg acg ggg gag agg gtt tgg gaa     1256
Cys Arg Ser Asn Gly Ser Arg Val Pro Thr Gly Glu Arg Val Trp Glu
```

-continued

|  |  |  |  |  |  |  |  |  |  |  |  |  |  |  |  |
|---|---|---|---|---|---|---|---|---|---|---|---|---|---|---|---|
|  |  | 230 |  |  |  | 235 |  |  |  |  | 240 |  |  |  |  |
| cgt | ggg | aac | gtc | aca | ctt | ttg | tgt | gac | tgc | ccc | aac | ggt | cct | tgg gtg | 1304 |
| Arg | Gly | Asn | Val | Thr | Leu | Leu | Cys | Asp | Cys | Pro | Asn | Gly | Pro | Trp Val |  |
|  |  | 245 |  |  |  | 250 |  |  |  |  | 255 |  |  |  |  |

| tgg gtc ccg gcc ctt tgc cag gca atc gga tgg ggc gac cct atc act | 1352 |
| Trp Val Pro Ala Leu Cys Gln Ala Ile Gly Trp Gly Asp Pro Ile Thr |  |
| 260 265 270 |  |

| cat tgg agc cac gga caa aat cag tgg ccc ctt tct tgt ccc caa ttt | 1400 |
| His Trp Ser His Gly Gln Asn Gln Trp Pro Leu Ser Cys Pro Gln Phe |  |
| 275 280 285 |  |

| gtc tac ggc gcc gtt tca gtg acc tgc gtg tgg ggt tct gtg tct tgg | 1448 |
| Val Tyr Gly Ala Val Ser Val Thr Cys Val Trp Gly Ser Val Ser Trp |  |
| 290 295 300 305 |  |

| ttt gct tcc act ggg ggt cgc gac tcc aag gtt gat gtg tgg agt ttg | 1496 |
| Phe Ala Ser Thr Gly Gly Arg Asp Ser Lys Val Asp Val Trp Ser Leu |  |
| 310 315 320 |  |

| gtt cca gtt ggc tct gcc agc tgc acc ata gcc gca ctg gga tct tcg | 1544 |
| Val Pro Val Gly Ser Ala Ser Cys Thr Ile Ala Ala Leu Gly Ser Ser |  |
| 325 330 335 |  |

| gat cgc gac aca gtg gtt gag ctc tcc gag tgg gga att ccc tgc gcc | 1592 |
| Asp Arg Asp Thr Val Val Glu Leu Ser Glu Trp Gly Ile Pro Cys Ala |  |
| 340 345 350 |  |

| act tgt atc ctg gac agg cgg cct gcc tcg tgt ggc acc tgt gtg agg | 1640 |
| Thr Cys Ile Leu Asp Arg Arg Pro Ala Ser Cys Gly Thr Cys Val Arg |  |
| 355 360 365 |  |

| gac tgc tgg ccc gag acc ggg tcg gta cgt ttc cca ttc cac agg tgt | 1688 |
| Asp Cys Trp Pro Glu Thr Gly Ser Val Arg Phe Pro Phe His Arg Cys |  |
| 370 375 380 385 |  |

| ggc gcg gga ccg agg ctg acc aga gac ctt gag gct gtg ccc ttc gtc | 1736 |
| Gly Ala Gly Pro Arg Leu Thr Arg Asp Leu Glu Ala Val Pro Phe Val |  |
| 390 395 400 |  |

| aat agg aca act ccc ttc acc ata agg ggg ccc ctg ggc aac cag ggg | 1784 |
| Asn Arg Thr Thr Pro Phe Thr Ile Arg Gly Pro Leu Gly Asn Gln Gly |  |
| 405 410 415 |  |

| cga ggc aac ccg gtg cgg tcg ccc ttg ggt ttt ggg tcc tac acc atg | 1832 |
| Arg Gly Asn Pro Val Arg Ser Pro Leu Gly Phe Gly Ser Tyr Thr Met |  |
| 420 425 430 |  |

| acc aag atc cga gac tcc tta cac ttg gtg aaa tgt ccc acc cca gcc | 1880 |
| Thr Lys Ile Arg Asp Ser Leu His Leu Val Lys Cys Pro Thr Pro Ala |  |
| 435 440 445 |  |

| att gag cct ccc acc gga acg ttt ggg ttc ttc cca gga gtc ccc ccc | 1928 |
| Ile Glu Pro Pro Thr Gly Thr Phe Gly Phe Phe Pro Gly Val Pro Pro |  |
| 450 455 460 465 |  |

| ctt aac aac tgc atg ctt ctc ggc act gag gtg tca gag gta ttg ggt | 1976 |
| Leu Asn Asn Cys Met Leu Leu Gly Thr Glu Val Ser Glu Val Leu Gly |  |
| 470 475 480 |  |

| ggg gcg ggc ctc act ggg ggg ttt tac gaa cct ctg gtg cgg cgg tgt | 2024 |
| Gly Ala Gly Leu Thr Gly Gly Phe Tyr Glu Pro Leu Val Arg Arg Cys |  |
| 485 490 495 |  |

| tca gag ctg atg ggt cgg cgg aat ccg gtc tgc ccg ggg ttt gca tgg | 2072 |
| Ser Glu Leu Met Gly Arg Arg Asn Pro Val Cys Pro Gly Phe Ala Trp |  |
| 500 505 510 |  |

| ctc tct tcg gga cgg cct gat ggg ttc ata cat gtt cag ggc cac ttg | 2120 |
| Leu Ser Ser Gly Arg Pro Asp Gly Phe Ile His Val Gln Gly His Leu |  |
| 515 520 525 |  |

| cag gag gtg gat gcg ggc aac ttc att ccg ccc cca cgc tgg ttg ctc | 2168 |
| Gln Glu Val Asp Ala Gly Asn Phe Ile Pro Pro Pro Arg Trp Leu Leu |  |
| 530 535 540 545 |  |

| ttg gac ttt gta ttt gtc ctg tta tac ctg atg aag ctg gca gag gca | 2216 |
| Leu Asp Phe Val Phe Val Leu Leu Tyr Leu Met Lys Leu Ala Glu Ala |  |

| | | |
|---|---|---|
| | 550 555 560 | |
| cgg ttg gtc ccg ctg atc ctc ctc ctg cta tgg tgg tgg gtg aac cag<br>Arg Leu Val Pro Leu Ile Leu Leu Leu Trp Trp Trp Val Asn Gln<br>565 570 575 | 2264 |
| ttg gcg gtc ctt gkt gtg scg gct gck crc gcc gcc gtg gct gga gag<br>Leu Ala Val Leu Xaa Val Xaa Ala Xaa Xaa Ala Ala Val Ala Gly Glu<br>580 585 590 | 2312 |
| gtg ttt gcg ggc cct gcc ttg tcc tgg tgt ctg ggc cta ccc ttc gtg<br>Val Phe Ala Gly Pro Ala Leu Ser Trp Cys Leu Gly Leu Pro Phe Val<br>595 600 605 | 2360 |
| agt atg atc ctg ggg cta gca aac ctg gtg ttg tac ttc cgc tgg atg<br>Ser Met Ile Leu Gly Leu Ala Asn Leu Val Leu Tyr Phe Arg Trp Met<br>610 615 620 625 | 2408 |
| ggt cct caa cgc ctg atg ttc ctc gtg ttg tgg aag ctc gct cgg ggg<br>Gly Pro Gln Arg Leu Met Phe Leu Val Leu Trp Lys Leu Ala Arg Gly<br>630 635 640 | 2456 |
| gct ttc ccg ctg gca tta ctg atg ggg att tcc gcc act cgc ggc cgc<br>Ala Phe Pro Leu Ala Leu Leu Met Gly Ile Ser Ala Thr Arg Gly Arg<br>645 650 655 | 2504 |
| acc tct gtg ctt ggc gcc gaa ttc tgc ttt gat gtc acc ttt gaa gtg<br>Thr Ser Val Leu Gly Ala Glu Phe Cys Phe Asp Val Thr Phe Glu Val<br>660 665 670 | 2552 |
| gac acg tca gtc ttg ggt tgg gtg gtt gct agt gtg gtg gct tgg gcc<br>Asp Thr Ser Val Leu Gly Trp Val Val Ala Ser Val Val Ala Trp Ala<br>675 680 685 | 2600 |
| ata gcg ctc ctg agc tct atg agc gcg ggg ggg tgg aag cac aaa gcc<br>Ile Ala Leu Leu Ser Ser Met Ser Ala Gly Gly Trp Lys His Lys Ala<br>690 695 700 705 | 2648 |
| ata atc tat agg acg tgg tgt aaa ggg tac cag gcy ctt cgc cag cgc<br>Ile Ile Tyr Arg Thr Trp Cys Lys Gly Tyr Gln Xaa Leu Arg Gln Arg<br>710 715 720 | 2696 |
| gtg gtg cgt agc ccc ctc ggg gag ggg cgg ccc acc aag ccg ctg acg<br>Val Val Arg Ser Pro Leu Gly Glu Gly Arg Pro Thr Lys Pro Leu Thr<br>725 730 735 | 2744 |
| ata gcc tgg tgt ctg gcc tct tac atc tgg ccg gac gct gtg atg ttg<br>Ile Ala Trp Cys Leu Ala Ser Tyr Ile Trp Pro Asp Ala Val Met Leu<br>740 745 750 | 2792 |
| gtg gtt gtg gcc atg gtc ctc ctc ttc ggc ctt ttc gac gcg ctc gat<br>Val Val Val Ala Met Val Leu Leu Phe Gly Leu Phe Asp Ala Leu Asp<br>755 760 765 | 2840 |
| tgg gcc ttg gag gag ctc ctt gtg tcg cgg cct tcg ttg cgt cgt ttg<br>Trp Ala Leu Glu Glu Leu Leu Val Ser Arg Pro Ser Leu Arg Arg Leu<br>770 775 780 785 | 2888 |
| gca agg gtg gtg gag tgt tgt gtg atg gcg ggc gag aag gcc act acc<br>Ala Arg Val Val Glu Cys Cys Val Met Ala Gly Glu Lys Ala Thr Thr<br>790 795 800 | 2936 |
| gtc cgg ctt gtg tcc aag atg tgc gcg aga ggg gcc tac ctg ttt gac<br>Val Arg Leu Val Ser Lys Met Cys Ala Arg Gly Ala Tyr Leu Phe Asp<br>805 810 815 | 2984 |
| cac atg ggg tcg ttc tcg cgc gcg gtc aag gag cgc ttg ctg gag tgg<br>His Met Gly Ser Phe Ser Arg Ala Val Lys Glu Arg Leu Leu Glu Trp<br>820 825 830 | 3032 |
| gac gcg gct ttg gag mcc ctg tca ttc act agg acg gac tgt cgc atc<br>Asp Ala Ala Leu Glu Xaa Leu Ser Phe Thr Arg Thr Asp Cys Arg Ile<br>835 840 845 | 3080 |
| ata cga gac gcc gcc agg acc ctg agc tgc ggc caa tgc gtc atg ggc<br>Ile Arg Asp Ala Ala Arg Thr Leu Ser Cys Gly Gln Cys Val Met Gly<br>850 855 860 865 | 3128 |
| ttg ccc gtg gtg gct agg cgc ggc gat gag gtc ctg att ggg gtc ttt<br>Leu Pro Val Val Ala Arg Arg Gly Asp Glu Val Leu Ile Gly Val Phe | 3176 |

|  |  |
|---|---|
| cag gat gtg aac cac ttg cct ccg ggg ttt gyt cct aca gcg cct gtt<br>Gln Asp Val Asn His Leu Pro Pro Gly Phe Xaa Pro Thr Ala Pro Val<br>885              890              895 | 3224 |
| gtc atc cgt cgg tgc gga aag ggc ttc ctc ggg gtc act aag gct gcc<br>Val Ile Arg Arg Cys Gly Lys Gly Phe Leu Gly Val Thr Lys Ala Ala<br>900              905              910 | 3272 |
| ttg act ggt cgg gat cct gac tta cac cca gga aac gtc atg gtt ttg<br>Leu Thr Gly Arg Asp Pro Asp Leu His Pro Gly Asn Val Met Val Leu<br>915              920              925 | 3320 |
| ggg acg gct acc tcg cgc agc atg gga acg tgc tta aac ggg ttg ctg<br>Gly Thr Ala Thr Ser Arg Ser Met Gly Thr Cys Leu Asn Gly Leu Leu<br>930              935              940              945 | 3368 |
| ttc acg aca ttc cat ggg gct tct tcc cga acc att gcg aca cct gtg<br>Phe Thr Thr Phe His Gly Ala Ser Ser Arg Thr Ile Ala Thr Pro Val<br>950              955              960 | 3416 |
| ggg gcc ctt aac cca agg tgg tgg tcg gcc agt gat gac gtc acg gtc<br>Gly Ala Leu Asn Pro Arg Trp Trp Ser Ala Ser Asp Asp Val Thr Val<br>965            970              975 | 3464 |
| tat ccc ctc ccc gat gga gct aac tcg ttg gtt ccc tgc tcg tgt cag<br>Tyr Pro Leu Pro Asp Gly Ala Asn Ser Leu Val Pro Cys Ser Cys Gln<br>980              985              990 | 3512 |
| gct gag tcc tgt tgg gtc aty cga tcc gat ggg gct ctt tgc cat ggc<br>Ala Glu Ser Cys Trp Val Xaa Arg Ser Asp Gly Ala Leu Cys His Gly<br>995            1000            1005 | 3560 |
| ttg agc aag ggg gac aag gta gaa ctg gac gtg gcc atg gag gtt gct<br>Leu Ser Lys Gly Asp Lys Val Glu Leu Asp Val Ala Met Glu Val Ala<br>1010           1015           1020           1025 | 3608 |
| gac ttt cgt ggg tcg tct ggg tct cct gtc cta tgc gac gag ggg cac<br>Asp Phe Arg Gly Ser Ser Gly Ser Pro Val Leu Cys Asp Glu Gly His<br>1030           1035           1040 | 3656 |
| gct gta gga atg ctc gtg tcc gtc ctt cat tcg ggg ggg agg gtg acc<br>Ala Val Gly Met Leu Val Ser Val Leu His Ser Gly Gly Arg Val Thr<br>1045           1050           1055 | 3704 |
| gcg gct cga ttc act cgg ccg tgg acc caa gtc cca aca gac gcc aag<br>Ala Ala Arg Phe Thr Arg Pro Trp Thr Gln Val Pro Thr Asp Ala Lys<br>1060           1065           1070 | 3752 |
| act acc act gag cca ccc ccg gtg cca gct aaa ggg gtt ttc aaa gag<br>Thr Thr Thr Glu Pro Pro Pro Val Pro Ala Lys Gly Val Phe Lys Glu<br>1075           1080           1085 | 3800 |
| gct cct ctt ttc atg cca aca ggg gcg ggg aaa agc aca cgc gtc cct<br>Ala Pro Leu Phe Met Pro Thr Gly Ala Gly Lys Ser Thr Arg Val Pro<br>1090           1095           1100           1105 | 3848 |
| ttg gag tat gga aac atg ggg cac aag gtc ctg att ctc aac ccg tcg<br>Leu Glu Tyr Gly Asn Met Gly His Lys Val Leu Ile Leu Asn Pro Ser<br>1110           1115           1120 | 3896 |
| gtt gcc act gtg agg gcc atg ggc cct tac atg gag agg ctg gcg ggg<br>Val Ala Thr Val Arg Ala Met Gly Pro Tyr Met Glu Arg Leu Ala Gly<br>1125           1130           1135 | 3944 |
| aaa cat cct agc att ttc tgt gga cac gac aca aca gct ttc aca cgg<br>Lys His Pro Ser Ile Phe Cys Gly His Asp Thr Thr Ala Phe Thr Arg<br>1140           1145           1150 | 3992 |
| atc acg gac tct cca ttg acg tac tct acc tat ggg agg ttt ctg gcc<br>Ile Thr Asp Ser Pro Leu Thr Tyr Ser Thr Tyr Gly Arg Phe Leu Ala<br>1155           1160           1165 | 4040 |
| aac ccg agg cag atg ctg agg gga gtt tcc gtg gtc atc tgt gat gag<br>Asn Pro Arg Gln Met Leu Arg Gly Val Ser Val Val Ile Cys Asp Glu<br>1170           1175           1180           1185 | 4088 |
| tgc cac agt cat gac tca act gtg ttg ctg ggt ata ggc agg gtc agg<br>Cys His Ser His Asp Ser Thr Val Leu Leu Gly Ile Gly Arg Val Arg | 4136 |

-continued

|  |  |  |
|---|---|---|
| gac gtg gcg cgg ggg tgt gga gtg caa tta gtg ctc tac gct act gcg<br>Asp Val Ala Arg Gly Cys Gly Val Gln Leu Val Leu Tyr Ala Thr Ala<br>    1205                1210                1215 | 4184 |  |
| act ccc ccg ggc tcg cct atg act cag cat cca tcc ata att gag aca<br>Thr Pro Pro Gly Ser Pro Met Thr Gln His Pro Ser Ile Ile Glu Thr<br>1220                1225                1230 | 4232 |  |
| aag ctg gac gtt ggt gag atc ccc ttt tat ggg cat ggt atc ccc ctc<br>Lys Leu Asp Val Gly Glu Ile Pro Phe Tyr Gly His Gly Ile Pro Leu<br>    1235                1240                1245 | 4280 |  |
| gag cgt atg agg act ggt cgc cac ctt gta ttc tgc cat tcc aag gcg<br>Glu Arg Met Arg Thr Gly Arg His Leu Val Phe Cys His Ser Lys Ala<br>1250                1255                1260                1265 | 4328 |  |
| gag tgc gag aga ttg gcc ggc cag ttc tcc gcg cgg ggg gtt aat gcc<br>Glu Cys Glu Arg Leu Ala Gly Gln Phe Ser Ala Arg Gly Val Asn Ala<br>            1270                1275                1280 | 4376 |  |
| atc gcc tat tat agg ggt aag gac agt tcc atc atc aaa gac gga gac<br>Ile Ala Tyr Tyr Arg Gly Lys Asp Ser Ser Ile Ile Lys Asp Gly Asp<br>    1285                1290                1295 | 4424 |  |
| ctg gtg gtt tgt gcg aca gac gcg ctc tct acc ggg tac aca gga aac<br>Leu Val Val Cys Ala Thr Asp Ala Leu Ser Thr Gly Tyr Thr Gly Asn<br>1300                1305                1310 | 4472 |  |
| ttc gat tct gtc acc gac tgt ggg ttg gtg gtg gag gag gtc gtt gag<br>Phe Asp Ser Val Thr Asp Cys Gly Leu Val Val Glu Glu Val Val Glu<br>    1315                1320                1325 | 4520 |  |
| gtg acc ctt gat ccc acc att acc att tcc ttg cgg act gtc cct gct<br>Val Thr Leu Asp Pro Thr Ile Thr Ile Ser Leu Arg Thr Val Pro Ala<br>1330                1335                1340                1345 | 4568 |  |
| tcg gct gaa ttg tcg atg cag cgg cgc gga cgc acg ggg aga ggt cgg<br>Ser Ala Glu Leu Ser Met Gln Arg Arg Gly Arg Thr Gly Arg Gly Arg<br>            1350                1355                1360 | 4616 |  |
| tcg ggc cgc tac tac tac gct ggg gtc ggt aag gct ccc gcg ggg gtg<br>Ser Gly Arg Tyr Tyr Tyr Ala Gly Val Gly Lys Ala Pro Ala Gly Val<br>    1365                1370                1375 | 4664 |  |
| gtg cgg tct ggt ccg gtc tgg tcg gca gtg gaa gct gga gtg acc tgg<br>Val Arg Ser Gly Pro Val Trp Ser Ala Val Glu Ala Gly Val Thr Trp<br>1380                1385                1390 | 4712 |  |
| tat gga atg gaa cct gac ttg aca gca aac ctt ctg aga ctt tac gac<br>Tyr Gly Met Glu Pro Asp Leu Thr Ala Asn Leu Leu Arg Leu Tyr Asp<br>    1395                1400                1405 | 4760 |  |
| gac tgc cct tac acc gca gcc gtc gca gct gac att ggt gaa gcc gcg<br>Asp Cys Pro Tyr Thr Ala Ala Val Ala Ala Asp Ile Gly Glu Ala Ala<br>1410                1415                1420                1425 | 4808 |  |
| gtg ttc ttt gcg ggc ctc gcg ccc ctc agg atg cat ccc gat gtt agc<br>Val Phe Phe Ala Gly Leu Ala Pro Leu Arg Met His Pro Asp Val Ser<br>            1430                1435                1440 | 4856 |  |
| tgg gca aaa gtt cgc ggc gtc aat tgg ccc ctc ctg gtg ggt gtt cag<br>Trp Ala Lys Val Arg Gly Val Asn Trp Pro Leu Leu Val Gly Val Gln<br>    1445                1450                1455 | 4904 |  |
| cgg acg atg tgt cgg gaa aca ctg tct ccc ggc ccg tcg gac gac cct<br>Arg Thr Met Cys Arg Glu Thr Leu Ser Pro Gly Pro Ser Asp Asp Pro<br>1460                1465                1470 | 4952 |  |
| cag tgg gca ggt ctg aaa ggc ccg aat cct gtc cca cta ctg ctg agg<br>Gln Trp Ala Gly Leu Lys Gly Pro Asn Pro Val Pro Leu Leu Leu Arg<br>    1475                1480                1485 | 5000 |  |
| tgg ggc aat gat ttg cca tca aaa gtg gcc ggc cac cac ata gtt gac<br>Trp Gly Asn Asp Leu Pro Ser Lys Val Ala Gly His His Ile Val Asp<br>1490                1495                1500                1505 | 5048 |  |
| gat ctg gtc cgt cgg ctc ggt gtg gcg gag gga tac gtg cgc tgt gat<br>Asp Leu Val Arg Arg Leu Gly Val Ala Glu Gly Tyr Val Arg Cys Asp | 5096 |  |

```
                    1510              1515              1520
gct ggr ccc atc ctc atg gtg ggc ttg gcc ata gcg ggc ggc atg atc         5144
Ala Xaa Pro Ile Leu Met Val Gly Leu Ala Ile Ala Gly Gly Met Ile
        1525              1530              1535 tac gcc tct tac act ggg tcg cta gtg gtg gta aca gac tgg gat gtg         5192
Tyr Ala Ser Tyr Thr Gly Ser Leu Val Val Val Thr Asp Trp Asp Val
    1540              1545              1550 aag gga ggt ggc aat ccc ctt tat agg agt ggt gac cag gcc acc cct         5240
Lys Gly Gly Gly Asn Pro Leu Tyr Arg Ser Gly Asp Gln Ala Thr Pro
        1555              1560              1565 caa ccc gtg gtg cag gtc ccc ccg gta gac cat cgg ccg ggg ggg gag         5288
Gln Pro Val Val Gln Val Pro Pro Val Asp His Arg Pro Gly Gly Glu
1570              1575              1580              1585 tct gcg cca cgg gat gcc aag aca gtg aca gat gcg gtg gca gcc atc         5336
Ser Ala Pro Arg Asp Ala Lys Thr Val Thr Asp Ala Val Ala Ala Ile
        1590              1595              1600 cag gtg aac tgc gat tgg tct gtg atg acc ctg tcg atc ggg gaa gtc         5384
Gln Val Asn Cys Asp Trp Ser Val Met Thr Leu Ser Ile Gly Glu Val
    1605              1610              1615 ctc acc ttg gct cag gct aag aca gcc gag gcc tac gca gct act tcc         5432
Leu Thr Leu Ala Gln Ala Lys Thr Ala Glu Ala Tyr Ala Ala Thr Ser
        1620              1625              1630 agg tgg ctc gct ggc tgc tac acg ggg acg cgg gcc gtc ccc act gta         5480
Arg Trp Leu Ala Gly Cys Tyr Thr Gly Thr Arg Ala Val Pro Thr Val
    1635              1640              1645 tca att gtt gac aag ctc ttc gcc ggg ggt tgg gcc gcc gtg gtg ggt         5528
Ser Ile Val Asp Lys Leu Phe Ala Gly Gly Trp Ala Ala Val Val Gly
1650              1655              1660              1665 cac tgt cac agc gtc att gct gcg gcg gtg gct gcc tat gga gct tct         5576
His Cys His Ser Val Ile Ala Ala Ala Val Ala Ala Tyr Gly Ala Ser
        1670              1675              1680 cga agt cct cca ctg gcc gcg gcg gcg tcc tac ctc atg ggg ttg ggc         5624
Arg Ser Pro Pro Leu Ala Ala Ala Ala Ser Tyr Leu Met Gly Leu Gly
    1685              1690              1695 gtc gga ggc aac gca cag gcg cgc ttg gct tca gct ctt cta ctg ggg         5672
Val Gly Gly Asn Ala Gln Ala Arg Leu Ala Ser Ala Leu Leu Leu Gly
        1700              1705              1710 gct gct ggt acg gct ctg ggg acc cct gtc gtg gga ctc acc atg gcg         5720
Ala Ala Gly Thr Ala Leu Gly Thr Pro Val Val Gly Leu Thr Met Ala
    1715              1720              1725 ggg gcc ttc atg ggc ggt gcc agc gtg tcc ccc tcc ctc gtc act gtc         5768
Gly Ala Phe Met Gly Gly Ala Ser Val Ser Pro Ser Leu Val Thr Val
1730              1735              1740              1745 cta ctt ggg gct gtg gga ggt tgg gag ggc gtt gtc aac gct gcc agt         5816
Leu Leu Gly Ala Val Gly Gly Trp Glu Gly Val Val Asn Ala Ala Ser
        1750              1755              1760 ctc gtc ttc gac ttc atg gct ggg aaa ctt tca aca gaa gac ctt tgg         5864
Leu Val Phe Asp Phe Met Ala Gly Lys Leu Ser Thr Glu Asp Leu Trp
    1765              1770              1775 tat gcc atc ccg gta ctc act agt cct ggr gcg ggc ctc gcg ggg att         5912
Tyr Ala Ile Pro Val Leu Thr Ser Pro Xaa Ala Gly Leu Ala Gly Ile
        1780              1785              1790 gcc ctt ggt ctg gtt ttg tac tca gca aac aac tct ggc act acc aca         5960
Ala Leu Gly Leu Val Leu Tyr Ser Ala Asn Asn Ser Gly Thr Thr Thr
    1795              1800              1805 tgg ctg aac cgt ctg ctg acg acg ttg cca cgg tca tct tgc ata ccc         6008
Trp Leu Asn Arg Leu Leu Thr Thr Leu Pro Arg Ser Ser Cys Ile Pro
1810              1815              1820              1825 gac agc tac ttc caa cag gct gac tac tgc gac aag gtc tcg gca atc         6056
Asp Ser Tyr Phe Gln Gln Ala Asp Tyr Cys Asp Lys Val Ser Ala Ile
```

|   |   |
|---|---|
| gtg cgc cgc ctg agc ctt act cgc acc gtg gtg gcc ctg gtc aac agg<br>Val Arg Arg Leu Ser Leu Thr Arg Thr Val Val Ala Leu Val Asn Arg<br>         1845                    1850                  1855 | 6104 |
| gag cct aag gtg gat gag gtc cag gtg ggg tac gtc tgg gat ctg tgg<br>Glu Pro Lys Val Asp Glu Val Gln Val Gly Tyr Val Trp Asp Leu Trp<br>1860                    1865                  1870 | 6152 |
| gag tgg gtg atg cgc cag gtg cgc atg gtg atg tct aga ctc cgg gcc<br>Glu Trp Val Met Arg Gln Val Arg Met Val Met Ser Arg Leu Arg Ala<br>    1875                    1880                  1885 | 6200 |
| ctc tgc cct gtg gtg tca ctc ccc ttg tgg cac tgc ggg gag ggg tgg<br>Leu Cys Pro Val Val Ser Leu Pro Leu Trp His Cys Gly Glu Gly Trp<br>1890                    1895                  1900                  1905 | 6248 |
| tcc ggt gaa tgg ctt ctc gat ggg cac gtg gag agt cgt tgt ctg tgc<br>Ser Gly Glu Trp Leu Leu Asp Gly His Val Glu Ser Arg Cys Leu Cys<br>         1910                    1915                  1920 | 6296 |
| ggg tgt gta atc acc ggc gac gtc ctc aat ggg caa ctc aaa gat cca<br>Gly Cys Val Ile Thr Gly Asp Val Leu Asn Gly Gln Leu Lys Asp Pro<br>              1925                  1930                  1935 | 6344 |
| gtt tac tct acc aag ctg tgc agg cac tac tgg atg gga act gtg ccg<br>Val Tyr Ser Thr Lys Leu Cys Arg His Tyr Trp Met Gly Thr Val Pro<br>        1940                    1945                  1950 | 6392 |
| gtc aac atg ctg ggc tac ggg gaa acc tca cct ctt ctc gcc tct gac<br>Val Asn Met Leu Gly Tyr Gly Glu Thr Ser Pro Leu Leu Ala Ser Asp<br>    1955                    1960                  1965 | 6440 |
| acc ccg aag gtg gta ccc ttc ggg acg tcg ggg tgg gct gag gtg gtg<br>Thr Pro Lys Val Val Pro Phe Gly Thr Ser Gly Trp Ala Glu Val Val<br>1970                    1975                  1980                  1985 | 6488 |
| gtg acc cct acc cac gtg gtg atc agg cgc acg tcc tgt tac aaa ctg<br>Val Thr Pro Thr His Val Val Ile Arg Arg Thr Ser Cys Tyr Lys Leu<br>         1990                    1995                  2000 | 6536 |
| ctt cgc cag caa att ctt tca gca gct gta gct gag ccc tac tac gtt<br>Leu Arg Gln Gln Ile Leu Ser Ala Ala Val Ala Glu Pro Tyr Tyr Val<br>              2005                  2010                  2015 | 6584 |
| gat ggc att ccg gtc tct tgg gag gct gac gcg aga gcg ccg gcc atg<br>Asp Gly Ile Pro Val Ser Trp Glu Ala Asp Ala Arg Ala Pro Ala Met<br>        2020                    2025                  2030 | 6632 |
| gtc tac ggt ccg ggc caa agt gtt acc att gat ggg gag cgc tac acc<br>Val Tyr Gly Pro Gly Gln Ser Val Thr Ile Asp Gly Glu Arg Tyr Thr<br>    2035                    2040                  2045 | 6680 |
| ctt ccg cac cag ttg cgg atg cgg aat gtg gcg ccc tct gag gtt tca<br>Leu Pro His Gln Leu Arg Met Arg Asn Val Ala Pro Ser Glu Val Ser<br>2050                    2055                  2060                  2065 | 6728 |
| tct gag gtc agc atc gag atc ggg acg gag act gaa gac tca gaa ctg<br>Ser Glu Val Ser Ile Glu Ile Gly Thr Glu Thr Glu Asp Ser Glu Leu<br>              2070                  2075                  2080 | 6776 |
| act gag gcc gat ttg cca cca gcg gct gct gcc ctc caa gcg ata gag<br>Thr Glu Ala Asp Leu Pro Pro Ala Ala Ala Ala Leu Gln Ala Ile Glu<br>        2085                    2090                  2095 | 6824 |
| aat gct gcg aga att ctc gaa ccg cac atc gat gtc ayc atg gag gat<br>Asn Ala Ala Arg Ile Leu Glu Pro His Ile Asp Val Xaa Met Glu Asp<br>    2100                    2105                  2110 | 6872 |
| tgc agt aca ccc tct ctc tgt ggt agt agc cga gag atg cct gtg tgg<br>Cys Ser Thr Pro Ser Leu Cys Gly Ser Ser Arg Glu Met Pro Val Trp<br>2115                    2120                  2125 | 6920 |
| gga gaa gac ata ccc cgc act cca tcg cct gca ctt atc tcg gtt acg<br>Gly Glu Asp Ile Pro Arg Thr Pro Ser Pro Ala Leu Ile Ser Val Thr<br>         2130                    2135                  2140                  2145 | 6968 |
| gag agc agc tca gat gag aag acc ctg tcg gtg acc tcc tcg cag gag<br>Glu Ser Ser Ser Asp Glu Lys Thr Leu Ser Val Thr Ser Ser Gln Glu | 7016 |

```
                     2150              2155              2160
gac acc ccg tcc tca gac tca ttt gaa gtc atc caa gag tct gat act       7064
Asp Thr Pro Ser Ser Asp Ser Phe Glu Val Ile Gln Glu Ser Asp Thr
            2165              2170              2175 gct gaa tca gag gaa agc gtc ttc aac gtg gct ctt tcc gta cta aaa       7112
Ala Glu Ser Glu Glu Ser Val Phe Asn Val Ala Leu Ser Val Leu Lys
        2180              2185              2190 gcc tta ttt cca cag agc gat gcc aca cga aag cta acg gtt aag atg       7160
Ala Leu Phe Pro Gln Ser Asp Ala Thr Arg Lys Leu Thr Val Lys Met
    2195              2200              2205 tct tgc tgt gtt gag aag agc gta aca cgc ttc ttt tct tta ggg ttg       7208
Ser Cys Cys Val Glu Lys Ser Val Thr Arg Phe Phe Ser Leu Gly Leu
2210              2215              2220              2225 acc gtg gct gac gtg gct agc ctg tgt gag atg gag atc cag aac cat       7256
Thr Val Ala Asp Val Ala Ser Leu Cys Glu Met Glu Ile Gln Asn His
            2230              2235              2240 aca gcc tat tgt gac aag gtg cgc act ccg ctc gaa ttg caa gtt ggg       7304
Thr Ala Tyr Cys Asp Lys Val Arg Thr Pro Leu Glu Leu Gln Val Gly
        2245              2250              2255 tgc ttg gtg ggc aat gaa ctt acc ttt gaa tgt gac aag tgt gag gca       7352
Cys Leu Val Gly Asn Glu Leu Thr Phe Glu Cys Asp Lys Cys Glu Ala
    2260              2265              2270 cgc caa gag acc ctt gcc tcc ttc tcc tac ata tgg tcc ggg gtc cca       7400
Arg Gln Glu Thr Leu Ala Ser Phe Ser Tyr Ile Trp Ser Gly Val Pro
2275              2280              2285 ctt act cgg gcc act ccg gcc aaa cca cca gtg gtg agg ccg gtg ggg       7448
Leu Thr Arg Ala Thr Pro Ala Lys Pro Pro Val Val Arg Pro Val Gly
2290              2295              2300              2305 tcc ttg ttg gtg gca gac acc acc aag gtc tac gtg acc aat ccg gac       7496
Ser Leu Leu Val Ala Asp Thr Thr Lys Val Tyr Val Thr Asn Pro Asp
            2310              2315              2320 aat gtt ggg agg agg gtt gac aag gtg act ttc tgg cgc gct cct cgg       7544
Asn Val Gly Arg Arg Val Asp Lys Val Thr Phe Trp Arg Ala Pro Arg
        2325              2330              2335 gta cac gac aag ttc ctc gtg gac tcg atc gag cgc gct cgg aga gct       7592
Val His Asp Lys Phe Leu Val Asp Ser Ile Glu Arg Ala Arg Arg Ala
    2340              2345              2350 gct caa ggc tgc cta agc atg ggt tac act tat gag gag gca ata agg       7640
Ala Gln Gly Cys Leu Ser Met Gly Tyr Thr Tyr Glu Glu Ala Ile Arg
2355              2360              2365 act gtt agg ccg cat gct gcc atg ggc tgg gga tct aag gtg tcg gtc       7688
Thr Val Arg Pro His Ala Ala Met Gly Trp Gly Ser Lys Val Ser Val
2370              2375              2380              2385 aag gac ttg gcc acc cct gcg ggg aag atg gct gtt cat gac cgg ctt       7736
Lys Asp Leu Ala Thr Pro Ala Gly Lys Met Ala Val His Asp Arg Leu
            2390              2395              2400 cag gag ata ctt gaa ggg act ccg gtc cct ttt acc ctg act gtc aaa       7784
Gln Glu Ile Leu Glu Gly Thr Pro Val Pro Phe Thr Leu Thr Val Lys
        2405              2410              2415 aag gag gtg ttc ttc aaa gat cgt aag gag gag aag gcc ccc cgc ctc       7832
Lys Glu Val Phe Phe Lys Asp Arg Lys Glu Glu Lys Ala Pro Arg Leu
    2420              2425              2430 att gtg ttc ccc ccc ctg gac ttc cgg ata gct gaa aag ctc att ctg       7880
Ile Val Phe Pro Pro Leu Asp Phe Arg Ile Ala Glu Lys Leu Ile Leu
2435              2440              2445 gga gac ccg ggg cgg gtt gca aag gcc ggt gtt ggg ggg gct tac gcc       7928
Gly Asp Pro Gly Arg Val Ala Lys Ala Gly Val Gly Gly Ala Tyr Ala
2450              2455              2460              2465 ttc cag tac acc ccc aac cag cgg gtt aag gag atg cta aag ctg tgg       7976
Phe Gln Tyr Thr Pro Asn Gln Arg Val Lys Glu Met Leu Lys Leu Trp
```

```
                    2470                2475                2480
gaa tca aag aag acc ccg tgc gcc atc tgt gtg gat gcc act tgc ttc       8024
Glu Ser Lys Lys Thr Pro Cys Ala Ile Cys Val Asp Ala Thr Cys Phe
            2485                2490                2495 gac agt agc att act gar gag gac gtg gca cta gag aca gag ctt tac       8072
Asp Ser Ser Ile Thr Glu Glu Asp Val Ala Leu Glu Thr Glu Leu Tyr
    2500                2505                2510 gcc ctg gcc tcg gac cat cca gaa tgg gtg cgc gcc ctg ggg aaa tac       8120
Ala Leu Ala Ser Asp His Pro Glu Trp Val Arg Ala Leu Gly Lys Tyr
        2515                2520                2525 trt gcc tct ggc aca atg gtg acc ccg gaa ggg gtg cca gtg ggc gag       8168
Xaa Ala Ser Gly Thr Met Val Thr Pro Glu Gly Val Pro Val Gly Glu
2530                2535                2540                2545 agg tat tgt agg tcc tcg ggt gtg ttg acc aca agt gct agc aac tgt       8216
Arg Tyr Cys Arg Ser Ser Gly Val Leu Thr Thr Ser Ala Ser Asn Cys
            2550                2555                2560 ttg acc tgc tac atc aaa gtg aga gcc gcc tgt gag agg atc gga ctg       8264
Leu Thr Cys Tyr Ile Lys Val Arg Ala Ala Cys Glu Arg Ile Gly Leu
    2565                2570                2575 aaa aat gtc tcg ctt ctc atc gcg ggc gat gac tgc tta att gtg tgc       8312
Lys Asn Val Ser Leu Leu Ile Ala Gly Asp Asp Cys Leu Ile Val Cys
        2580                2585                2590 gag agg cct gta tgc gac cct tgc gag gcc ctg ggc cga acc ctg gct       8360
Glu Arg Pro Val Cys Asp Pro Cys Glu Ala Leu Gly Arg Thr Leu Ala
2595                2600                2605 tcg tac ggg tac gcg tgt gag ccc tcg tat cac gct tca ctg gac aca       8408
Ser Tyr Gly Tyr Ala Cys Glu Pro Ser Tyr His Ala Ser Leu Asp Thr
2610                2615                2620                2625 gcc ccc ttc tgc tcc act tgg ctc gct gag tgc aat gcg gat ggg raa       8456
Ala Pro Phe Cys Ser Thr Trp Leu Ala Glu Cys Asn Ala Asp Gly Xaa
            2630                2635                2640 agg cat ttc ttc ctg acc acg gac ttt cgg aga cca ctc gct cgc atg       8504
Arg His Phe Phe Leu Thr Thr Asp Phe Arg Arg Pro Leu Ala Arg Met
    2645                2650                2655 tcg agc gag tac agt gac cct atg gct tcg gcc att ggt tac att ctc       8552
Ser Ser Glu Tyr Ser Asp Pro Met Ala Ser Ala Ile Gly Tyr Ile Leu
        2660                2665                2670 ctc tac ccc tgg crt ccc atc aca cgg tgg gtc atc atc ccg cat gtg       8600
Leu Tyr Pro Trp Xaa Pro Ile Thr Arg Trp Val Ile Ile Pro His Val
2675                2680                2685 cta aca tgc gct tct tcc cgg ggt ggt ggc aca csg tct gat ccg gtt       8648
Leu Thr Cys Ala Ser Ser Arg Gly Gly Gly Thr Xaa Ser Asp Pro Val
2690                2695                2700                2705 tgg tgt cag gtt cat ggt aac tac tac aag ttt ccc ctg gac aaa ctg       8696
Trp Cys Gln Val His Gly Asn Tyr Tyr Lys Phe Pro Leu Asp Lys Leu
            2710                2715                2720 cct aac atc atc gtg gcc ctc cac gga cca gca gcg ttg agg gtt acc       8744
Pro Asn Ile Ile Val Ala Leu His Gly Pro Ala Ala Leu Arg Val Thr
    2725                2730                2735 gca gac aca acc aaa aca aag atg gag gct ggg aag gtt ctg agc gac       8792
Ala Asp Thr Thr Lys Thr Lys Met Glu Ala Gly Lys Val Leu Ser Asp
        2740                2745                2750 ctc aag ctc cct ggt cta gcc gtc cac cgc aag aag gcc ggg gca ttg       8840
Leu Lys Leu Pro Gly Leu Ala Val His Arg Lys Lys Ala Gly Ala Leu
2755                2760                2765 cga aca cgc atg ctc cgg tcg cgc ggt tgg gcg gag ttg gct agg ggc       8888
Arg Thr Arg Met Leu Arg Ser Arg Gly Trp Ala Glu Leu Ala Arg Gly
2770                2775                2780                2785 ctg ttg tgg cat cca gga ctc cgg ctt cct ccc cct gag att gct ggt       8936
Leu Leu Trp His Pro Gly Leu Arg Leu Pro Pro Pro Glu Ile Ala Gly
```

-continued

```
                          2790                    2795                    2800
atc cca ggg ggt ttc cct ctg tcc ccc ccc tac atg ggg gtg gtt cat        8984
Ile Pro Gly Gly Phe Pro Leu Ser Pro Pro Tyr Met Gly Val Val His
            2805                    2810                    2815 caa ttg gat ttc aca gcs cag cgg agt cgc tgg cgg tgg ttg ggg ttc        9032
Gln Leu Asp Phe Thr Xaa Gln Arg Ser Arg Trp Arg Trp Leu Gly Phe
            2820                    2825                    2830 tta gcc ctg ctc atc gta gcg ctc ttt ggg tga actaaattca tctgttgcgg     9085
Leu Ala Leu Leu Ile Val Ala Leu Phe Gly
            2835                    2840 caaggttgag cggctgatca ccgctcaagg aggttcccgc cctccccgcc ccagggtct       9145 ccccgctggg taaaaagggc ccggccttgg gaggcatggt ggttactaac cccctggcag     9205
ggttaacgcc tgatggtgct aatgcactgc cgcttcggcg gcgggtcgct accttatagc     9265
gtaatccgtg actacgggct gctcgcagag ccctccccgg atggggcaca gtgcactgtg     9325
atctgaaggg gtgcaccccg gtaagagctc ggcccaaagg ccgggttcta ct             9377
```

<210> SEQ ID NO 2
<211> LENGTH: 2843
<212> TYPE: PRT
<213> ORGANISM: Hepatitis GB virus C
<220> FEATURE:
<221> NAME/KEY: MOD_RES
<222> LOCATION: (30)..(2823)
<223> OTHER INFORMATION: X = anything

<400> SEQUENCE: 2

```
Met Ala Val Leu Leu Leu Leu Val Glu Ala Gly Ala Ile Leu
  1               5                  10                  15

Ala Pro Ala Thr His Ala Cys Ser Ala Lys Gly Gln Tyr Xaa Leu Thr
                 20                  25                  30

Asn Cys Cys Ala Leu Glu Asp Ile Gly Phe Cys Leu Glu Gly Gly Cys
             35                  40                  45

Leu Val Ala Leu Gly Cys Thr Ile Cys Thr Asp Arg Cys Trp Pro Leu
         50                  55                  60

Tyr Gln Ala Gly Leu Ala Val Arg Pro Gly Lys Ser Ala Ala Gln Leu
 65                  70                  75                  80

Val Gly Glu Leu Gly Ser Leu Tyr Gly Pro Leu Ser Val Ser Ala Tyr
                 85                  90                  95

Val Ala Gly Ile Leu Gly Leu Gly Glu Val Tyr Ser Gly Val Leu Thr
            100                 105                 110

Val Gly Val Ala Leu Thr Arg Arg Val Tyr Pro Val Pro Asn Leu Thr
        115                 120                 125

Cys Ala Val Glu Cys Glu Leu Lys Trp Glu Ser Glu Phe Trp Arg Trp
    130                 135                 140

Thr Glu Gln Leu Ala Ser Asn Tyr Trp Ile Leu Glu Tyr Leu Trp Lys
145                 150                 155                 160

Val Pro Phe Asp Phe Trp Arg Gly Val Met Ser Leu Thr Pro Leu Leu
                165                 170                 175

Val Cys Val Ala Ala Leu Leu Leu Leu Glu Gln Arg Ile Val Met Val
            180                 185                 190

Phe Leu Leu Val Thr Met Ala Gly Met Ser Gln Gly Ala Pro Ala Ser
        195                 200                 205

Val Leu Gly Ser Arg Pro Phe Glu Ala Gly Leu Thr Trp Gln Ser Cys
    210                 215                 220

Ser Cys Arg Ser Asn Gly Ser Arg Val Pro Thr Gly Glu Arg Val Trp
225                 230                 235                 240
```

```
Glu Arg Gly Asn Val Thr Leu Leu Cys Asp Cys Pro Asn Pro Trp
                245                 250                 255

Val Trp Val Pro Ala Leu Cys Gln Ala Ile Gly Trp Gly Asp Pro Ile
        260                 265                 270

Thr His Trp Ser His Gly Gln Asn Gln Trp Pro Leu Ser Cys Pro Gln
            275                 280                 285

Phe Val Tyr Gly Ala Val Ser Val Thr Cys Val Trp Gly Ser Val Ser
        290                 295                 300

Trp Phe Ala Ser Thr Gly Gly Arg Asp Ser Lys Val Asp Val Trp Ser
305                 310                 315                 320

Leu Val Pro Val Gly Ser Ala Ser Cys Thr Ile Ala Ala Leu Gly Ser
                325                 330                 335

Ser Asp Arg Asp Thr Val Val Glu Leu Ser Glu Trp Gly Ile Pro Cys
            340                 345                 350

Ala Thr Cys Ile Leu Asp Arg Arg Pro Ala Ser Cys Gly Thr Cys Val
        355                 360                 365

Arg Asp Cys Trp Pro Glu Thr Gly Ser Val Arg Phe Pro Phe His Arg
370                 375                 380

Cys Gly Ala Gly Pro Arg Leu Thr Arg Asp Leu Glu Ala Val Pro Phe
385                 390                 395                 400

Val Asn Arg Thr Thr Pro Phe Thr Ile Arg Gly Pro Leu Gly Asn Gln
                405                 410                 415

Gly Arg Gly Asn Pro Val Arg Ser Pro Leu Gly Phe Gly Ser Tyr Thr
            420                 425                 430

Met Thr Lys Ile Arg Asp Ser Leu His Leu Val Lys Cys Pro Thr Pro
        435                 440                 445

Ala Ile Glu Pro Pro Thr Gly Thr Phe Gly Phe Phe Pro Gly Val Pro
    450                 455                 460

Pro Leu Asn Asn Cys Met Leu Leu Gly Thr Glu Val Ser Glu Val Leu
465                 470                 475                 480

Gly Gly Ala Gly Leu Thr Gly Gly Phe Tyr Glu Pro Leu Val Arg Arg
                485                 490                 495

Cys Ser Glu Leu Met Gly Arg Arg Asn Pro Val Cys Pro Gly Phe Ala
            500                 505                 510

Trp Leu Ser Ser Gly Arg Pro Asp Gly Phe Ile His Val Gln Gly His
        515                 520                 525

Leu Gln Glu Val Asp Ala Gly Asn Phe Ile Pro Pro Pro Arg Trp Leu
    530                 535                 540

Leu Leu Asp Phe Val Phe Val Leu Leu Tyr Leu Met Lys Leu Ala Glu
545                 550                 555                 560

Ala Arg Leu Val Pro Leu Ile Leu Leu Leu Leu Trp Trp Trp Val Asn
                565                 570                 575

Gln Leu Ala Val Leu Xaa Val Xaa Ala Xaa Xaa Ala Ala Val Ala Gly
            580                 585                 590

Glu Val Phe Ala Gly Pro Ala Leu Ser Trp Cys Leu Gly Leu Pro Phe
        595                 600                 605

Val Ser Met Ile Leu Gly Leu Ala Asn Leu Val Leu Tyr Phe Arg Trp
    610                 615                 620

Met Gly Pro Gln Arg Leu Met Phe Leu Val Leu Trp Lys Leu Ala Arg
625                 630                 635                 640

Gly Ala Phe Pro Leu Ala Leu Leu Met Gly Ile Ser Ala Thr Arg Gly
                645                 650                 655

Arg Thr Ser Val Leu Gly Ala Glu Phe Cys Phe Asp Val Thr Phe Glu
```

-continued

```
                660                 665                 670
Val Asp Thr Ser Val Leu Gly Trp Val Val Ala Ser Val Ala Trp
            675                 680                 685
Ala Ile Ala Leu Leu Ser Ser Met Ser Ala Gly Gly Trp Lys His Lys
            690                 695                 700
Ala Ile Ile Tyr Arg Thr Trp Cys Lys Gly Tyr Gln Xaa Leu Arg Gln
705                 710                 715                 720
Arg Val Val Arg Ser Pro Leu Gly Glu Gly Arg Pro Thr Lys Pro Leu
            725                 730                 735
Thr Ile Ala Trp Cys Leu Ala Ser Tyr Ile Trp Pro Asp Ala Val Met
            740                 745                 750
Leu Val Val Val Ala Met Val Leu Leu Phe Gly Leu Phe Asp Ala Leu
            755                 760                 765
Asp Trp Ala Leu Glu Glu Leu Leu Val Ser Arg Pro Ser Leu Arg Arg
            770                 775                 780
Leu Ala Arg Val Val Glu Cys Cys Val Met Ala Gly Glu Lys Ala Thr
785                 790                 795                 800
Thr Val Arg Leu Val Ser Lys Met Cys Ala Arg Gly Ala Tyr Leu Phe
            805                 810                 815
Asp His Met Gly Ser Phe Ser Arg Ala Val Lys Glu Arg Leu Leu Glu
            820                 825                 830
Trp Asp Ala Ala Leu Glu Xaa Leu Ser Phe Thr Arg Thr Asp Cys Arg
            835                 840                 845
Ile Ile Arg Asp Ala Ala Arg Thr Leu Ser Cys Gly Gln Cys Val Met
850                 855                 860
Gly Leu Pro Val Val Ala Arg Arg Gly Asp Glu Val Leu Ile Gly Val
865                 870                 875                 880
Phe Gln Asp Val Asn His Leu Pro Pro Gly Phe Xaa Pro Thr Ala Pro
            885                 890                 895
Val Val Ile Arg Arg Cys Gly Lys Gly Phe Leu Gly Val Thr Lys Ala
            900                 905                 910
Ala Leu Thr Gly Arg Asp Pro Asp Leu His Pro Gly Asn Val Met Val
            915                 920                 925
Leu Gly Thr Ala Thr Ser Arg Ser Met Gly Thr Cys Leu Asn Gly Leu
            930                 935                 940
Leu Phe Thr Thr Phe His Gly Ala Ser Ser Arg Thr Ile Ala Thr Pro
945                 950                 955                 960
Val Gly Ala Leu Asn Pro Arg Trp Trp Ser Ala Ser Asp Asp Val Thr
            965                 970                 975
Val Tyr Pro Leu Pro Asp Gly Ala Asn Ser Leu Val Pro Cys Ser Cys
            980                 985                 990
Gln Ala Glu Ser Cys Trp Val Xaa Arg Ser Asp Gly Ala Leu Cys His
            995                 1000                1005
Gly Leu Ser Lys Gly Asp Lys Val Glu Leu Asp Val Ala Met Glu Val
            1010                1015                1020
Ala Asp Phe Arg Gly Ser Ser Gly Ser Pro Val Leu Cys Asp Glu Gly
1025                1030                1035                1040
His Ala Val Gly Met Leu Val Ser Val Leu His Ser Gly Gly Arg Val
            1045                1050                1055
Thr Ala Ala Arg Phe Thr Arg Pro Trp Thr Gln Val Pro Thr Asp Ala
            1060                1065                1070
Lys Thr Thr Thr Glu Pro Pro Pro Val Pro Ala Lys Gly Val Phe Lys
            1075                1080                1085
```

-continued

```
Glu Ala Pro Leu Phe Met Pro Thr Gly Ala Gly Lys Ser Thr Arg Val
    1090                1095                1100

Pro Leu Glu Tyr Gly Asn Met Gly His Lys Val Leu Ile Leu Asn Pro
1105                1110                1115                1120

Ser Val Ala Thr Val Arg Ala Met Gly Pro Tyr Met Glu Arg Leu Ala
            1125                1130                1135

Gly Lys His Pro Ser Ile Phe Cys Gly His Asp Thr Thr Ala Phe Thr
        1140                1145                1150

Arg Ile Thr Asp Ser Pro Leu Thr Tyr Ser Thr Tyr Gly Arg Phe Leu
    1155                1160                1165

Ala Asn Pro Arg Gln Met Leu Arg Gly Val Ser Val Val Ile Cys Asp
1170                1175                1180

Glu Cys His Ser His Asp Ser Thr Val Leu Leu Gly Ile Gly Arg Val
1185                1190                1195                1200

Arg Asp Val Ala Arg Gly Cys Gly Val Gln Leu Val Leu Tyr Ala Thr
        1205                1210                1215

Ala Thr Pro Pro Gly Ser Pro Met Thr Gln His Pro Ser Ile Ile Glu
        1220                1225                1230

Thr Lys Leu Asp Val Gly Glu Ile Pro Phe Tyr Gly His Gly Ile Pro
        1235                1240                1245

Leu Glu Arg Met Arg Thr Gly Arg His Leu Val Phe Cys His Ser Lys
    1250                1255                1260

Ala Glu Cys Glu Arg Leu Ala Gly Gln Phe Ser Ala Arg Gly Val Asn
1265                1270                1275                1280

Ala Ile Ala Tyr Tyr Arg Gly Lys Asp Ser Ser Ile Ile Lys Asp Gly
        1285                1290                1295

Asp Leu Val Val Cys Ala Thr Asp Ala Leu Ser Thr Gly Tyr Thr Gly
        1300                1305                1310

Asn Phe Asp Ser Val Thr Asp Cys Gly Leu Val Val Glu Glu Val Val
        1315                1320                1325

Glu Val Thr Leu Asp Pro Thr Ile Thr Ile Ser Leu Arg Thr Val Pro
    1330                1335                1340

Ala Ser Ala Glu Leu Ser Met Gln Arg Arg Gly Arg Thr Gly Arg Gly
1345                1350                1355                1360

Arg Ser Gly Arg Tyr Tyr Tyr Ala Gly Val Gly Lys Ala Pro Ala Gly
        1365                1370                1375

Val Val Arg Ser Gly Pro Val Trp Ser Ala Val Glu Ala Gly Val Thr
        1380                1385                1390

Trp Tyr Gly Met Glu Pro Asp Leu Thr Ala Asn Leu Leu Arg Leu Tyr
        1395                1400                1405

Asp Asp Cys Pro Tyr Thr Ala Ala Val Ala Ala Asp Ile Gly Glu Ala
        1410                1415                1420

Ala Val Phe Phe Ala Gly Leu Ala Pro Leu Arg Met His Pro Asp Val
1425                1430                1435                1440

Ser Trp Ala Lys Val Arg Gly Val Asn Trp Pro Leu Leu Val Gly Val
            1445                1450                1455

Gln Arg Thr Met Cys Arg Glu Thr Leu Ser Pro Gly Pro Ser Asp Asp
        1460                1465                1470

Pro Gln Trp Ala Gly Leu Lys Gly Pro Asn Pro Val Pro Leu Leu Leu
        1475                1480                1485

Arg Trp Gly Asn Asp Leu Pro Ser Lys Val Ala Gly His His Ile Val
    1490                1495                1500

Asp Asp Leu Val Arg Arg Leu Gly Val Ala Glu Gly Tyr Val Arg Cys
1505                1510                1515                1520
```

-continued

Asp Ala Xaa Pro Ile Leu Met Val Gly Leu Ala Ile Ala Gly Gly Met
            1525                1530                1535

Ile Tyr Ala Ser Tyr Thr Gly Ser Leu Val Val Val Thr Asp Trp Asp
        1540                1545                1550

Val Lys Gly Gly Gly Asn Pro Leu Tyr Arg Ser Gly Asp Gln Ala Thr
1555                1560                1565

Pro Gln Pro Val Val Gln Val Pro Val Asp His Arg Pro Gly Gly
    1570                1575                1580

Glu Ser Ala Pro Arg Asp Ala Lys Thr Val Thr Asp Ala Val Ala Ala
1585                1590                1595                1600

Ile Gln Val Asn Cys Asp Trp Ser Val Met Thr Leu Ser Ile Gly Glu
            1605                1610                1615

Val Leu Thr Leu Ala Gln Ala Lys Thr Ala Glu Ala Tyr Ala Ala Thr
        1620                1625                1630

Ser Arg Trp Leu Ala Gly Cys Tyr Thr Gly Thr Arg Ala Val Pro Thr
    1635                1640                1645

Val Ser Ile Val Asp Lys Leu Phe Ala Gly Gly Trp Ala Ala Val Val
        1650                1655                1660

Gly His Cys His Ser Val Ile Ala Ala Ala Val Ala Ala Tyr Gly Ala
1665                1670                1675                1680

Ser Arg Ser Pro Pro Leu Ala Ala Ala Ala Ser Tyr Leu Met Gly Leu
        1685                1690                1695

Gly Val Gly Gly Asn Ala Gln Ala Arg Leu Ala Ser Ala Leu Leu Leu
    1700                1705                1710

Gly Ala Ala Gly Thr Ala Leu Gly Thr Pro Val Val Gly Leu Thr Met
        1715                1720                1725

Ala Gly Ala Phe Met Gly Gly Ala Ser Val Ser Pro Ser Leu Val Thr
    1730                1735                1740

Val Leu Leu Gly Ala Val Gly Gly Trp Glu Gly Val Val Asn Ala Ala
1745                1750                1755                1760

Ser Leu Val Phe Asp Phe Met Ala Gly Lys Leu Ser Thr Glu Asp Leu
        1765                1770                1775

Trp Tyr Ala Ile Pro Val Leu Thr Ser Pro Xaa Ala Gly Leu Ala Gly
            1780                1785                1790

Ile Ala Leu Gly Leu Val Leu Tyr Ser Ala Asn Asn Ser Gly Thr Thr
        1795                1800                1805

Thr Trp Leu Asn Arg Leu Leu Thr Thr Leu Pro Arg Ser Ser Cys Ile
1810                1815                1820

Pro Asp Ser Tyr Phe Gln Gln Ala Asp Tyr Cys Asp Lys Val Ser Ala
1825                1830                1835                1840

Ile Val Arg Arg Leu Ser Leu Thr Arg Thr Val Val Ala Leu Val Asn
        1845                1850                1855

Arg Glu Pro Lys Val Asp Glu Val Gln Val Gly Tyr Val Trp Asp Leu
            1860                1865                1870

Trp Glu Trp Val Met Arg Gln Val Arg Met Val Met Ser Arg Leu Arg
        1875                1880                1885

Ala Leu Cys Pro Val Val Ser Leu Pro Leu Trp His Cys Gly Glu Gly
    1890                1895                1900

Trp Ser Gly Glu Trp Leu Leu Asp Gly His Val Glu Ser Arg Cys Leu
1905                1910                1915                1920

Cys Gly Cys Val Ile Thr Gly Asp Val Leu Asn Gly Gln Leu Lys Asp
            1925                1930                1935

Pro Val Tyr Ser Thr Lys Leu Cys Arg His Tyr Trp Met Gly Thr Val

```
                   1940                1945                1950
Pro Val Asn Met Leu Gly Tyr Gly Glu Thr Ser Pro Leu Leu Ala Ser
           1955                1960                1965

Asp Thr Pro Lys Val Val Pro Phe Gly Thr Ser Gly Trp Ala Glu Val
       1970                1975                1980

Val Val Thr Pro Thr His Val Val Ile Arg Arg Thr Ser Cys Tyr Lys
1985                1990                1995                2000

Leu Leu Arg Gln Gln Ile Leu Ser Ala Ala Val Ala Glu Pro Tyr Tyr
                2005                2010                2015

Val Asp Gly Ile Pro Val Ser Trp Glu Ala Asp Ala Arg Ala Pro Ala
           2020                2025                2030

Met Val Tyr Gly Pro Gly Gln Ser Val Thr Ile Asp Gly Glu Arg Tyr
       2035                2040                2045

Thr Leu Pro His Gln Leu Arg Met Arg Asn Val Ala Pro Ser Glu Val
   2050                2055                2060

Ser Ser Glu Val Ser Ile Glu Ile Gly Thr Glu Thr Glu Asp Ser Glu
2065                2070                2075                2080

Leu Thr Glu Ala Asp Leu Pro Pro Ala Ala Ala Leu Gln Ala Ile
                2085                2090                2095

Glu Asn Ala Ala Arg Ile Leu Glu Pro His Ile Asp Val Xaa Met Glu
           2100                2105                2110

Asp Cys Ser Thr Pro Ser Leu Cys Gly Ser Ser Arg Glu Met Pro Val
       2115                2120                2125

Trp Gly Glu Asp Ile Pro Arg Thr Pro Ser Pro Ala Leu Ile Ser Val
   2130                2135                2140

Thr Glu Ser Ser Ser Asp Glu Lys Thr Leu Ser Val Thr Ser Ser Gln
2145                2150                2155                2160

Glu Asp Thr Pro Ser Ser Asp Ser Phe Glu Val Ile Gln Glu Ser Asp
                2165                2170                2175

Thr Ala Glu Ser Glu Glu Ser Val Phe Asn Val Ala Leu Ser Val Leu
           2180                2185                2190

Lys Ala Leu Phe Pro Gln Ser Asp Ala Thr Arg Lys Leu Thr Val Lys
       2195                2200                2205

Met Ser Cys Cys Val Glu Lys Ser Val Thr Arg Phe Phe Ser Leu Gly
   2210                2215                2220

Leu Thr Val Ala Asp Val Ala Ser Leu Cys Glu Met Glu Ile Gln Asn
2225                2230                2235                2240

His Thr Ala Tyr Cys Asp Lys Val Arg Thr Pro Leu Gly Leu Gln Val
                2245                2250                2255

Gly Cys Leu Val Gly Asn Glu Leu Thr Phe Glu Cys Asp Lys Cys Glu
           2260                2265                2270

Ala Arg Gln Glu Thr Leu Ala Ser Phe Ser Tyr Ile Trp Ser Gly Val
       2275                2280                2285

Pro Leu Thr Arg Ala Thr Pro Ala Lys Pro Val Arg Pro Val
   2290                2295                2300

Gly Ser Leu Leu Val Ala Asp Thr Thr Lys Val Tyr Val Thr Asn Pro
2305                2310                2315                2320

Asp Asn Val Gly Arg Arg Val Asp Lys Val Thr Phe Trp Arg Ala Pro
                2325                2330                2335

Arg Val His Asp Lys Phe Leu Val Asp Ser Ile Glu Arg Ala Arg Arg
           2340                2345                2350

Ala Ala Gln Gly Cys Leu Ser Met Gly Tyr Thr Tyr Glu Glu Ala Ile
       2355                2360                2365
```

```
Arg Thr Val Arg Pro His Ala Met Gly Trp Gly Ser Lys Val Ser
    2370            2375                2380

Val Lys Asp Leu Ala Thr Pro Ala Gly Lys Met Ala Val His Asp Arg
2385                2390                2395                2400

Leu Gln Glu Ile Leu Glu Gly Thr Pro Val Pro Phe Thr Leu Thr Val
            2405                2410                2415

Lys Lys Glu Val Phe Phe Lys Asp Arg Lys Glu Lys Ala Pro Arg
    2420                2425                2430

Leu Ile Val Phe Pro Pro Leu Asp Phe Arg Ile Ala Glu Lys Leu Ile
        2435                2440                2445

Leu Gly Asp Pro Gly Arg Val Ala Lys Ala Gly Val Gly Gly Ala Tyr
    2450                2455                2460

Ala Phe Gln Tyr Thr Pro Asn Gln Arg Val Lys Glu Met Leu Lys Leu
2465                2470                2475                2480

Trp Glu Ser Lys Lys Thr Pro Cys Ala Ile Cys Val Asp Ala Thr Cys
            2485                2490                2495

Phe Asp Ser Ser Ile Thr Glu Glu Asp Val Ala Leu Glu Thr Glu Leu
            2500                2505                2510

Tyr Ala Leu Ala Ser Asp His Pro Glu Trp Val Arg Ala Leu Gly Lys
    2515                2520                2525

Tyr Xaa Ala Ser Gly Thr Met Val Thr Pro Glu Gly Val Pro Val Gly
    2530                2535                2540

Glu Arg Tyr Cys Arg Ser Ser Gly Val Leu Thr Thr Ser Ala Ser Asn
2545                2550                2555                2560

Cys Leu Thr Cys Tyr Ile Lys Val Arg Ala Ala Cys Glu Arg Ile Gly
            2565                2570                2575

Leu Lys Asn Val Ser Leu Leu Ile Ala Gly Asp Asp Cys Leu Ile Val
        2580                2585                2590

Cys Glu Arg Pro Val Cys Asp Pro Cys Glu Ala Leu Gly Arg Thr Leu
    2595                2600                2605

Ala Ser Tyr Gly Tyr Ala Cys Glu Pro Ser Tyr His Ala Ser Leu Asp
2610                2615                2620

Thr Ala Pro Phe Cys Ser Thr Trp Leu Ala Glu Cys Asn Ala Asp Gly
2625                2630                2635                2640

Xaa Arg His Phe Phe Leu Thr Thr Asp Phe Arg Arg Pro Leu Ala Arg
            2645                2650                2655

Met Ser Ser Glu Tyr Ser Asp Pro Met Ala Ser Ala Ile Gly Tyr Ile
            2660                2665                2670

Leu Leu Tyr Pro Trp Xaa Pro Ile Thr Arg Trp Val Ile Ile Pro His
        2675                2680                2685

Val Leu Thr Cys Ala Ser Ser Arg Gly Gly Gly Thr Xaa Ser Asp Pro
    2690                2695                2700

Val Trp Cys Gln Val His Gly Asn Tyr Tyr Lys Phe Pro Leu Asp Lys
2705                2710                2715                2720

Leu Pro Asn Ile Ile Val Ala Leu His Gly Pro Ala Ala Leu Arg Val
            2725                2730                2735

Thr Ala Asp Thr Thr Lys Thr Lys Met Glu Ala Gly Lys Val Leu Ser
            2740                2745                2750

Asp Leu Lys Leu Pro Gly Leu Ala Val His Arg Lys Lys Ala Gly Ala
        2755                2760                2765

Leu Arg Thr Arg Met Leu Arg Ser Arg Gly Trp Ala Glu Leu Ala Arg
    2770                2775                2780

Gly Leu Leu Trp His Pro Gly Leu Arg Leu Pro Pro Glu Ile Ala
2785                2790                2795                2800
```

```
Gly Ile Pro Gly Gly Phe Pro Leu Ser Pro Pro Tyr Met Gly Val Val
            2805                2810                2815

His Gln Leu Asp Phe Thr Xaa Gln Arg Ser Arg Trp Arg Trp Leu Gly
        2820                2825                2830

Phe Leu Ala Leu Leu Ile Val Ala Leu Phe Gly
        2835                2840

<210> SEQ ID NO 3
<211> LENGTH: 936
<212> TYPE: DNA
<213> ORGANISM: Hepatitis GB virus C
<220> FEATURE:
<221> NAME/KEY: CDS
<222> LOCATION: (1)..(936)

<400> SEQUENCE: 3 acc ata gcc gca ctg gga tct tcg gat cgc gac aca gtg gtt gag ctc      48
Thr Ile Ala Ala Leu Gly Ser Ser Asp Arg Asp Thr Val Val Glu Leu
  1               5                  10                  15 tcc gag tgg gga att ccc tgc gcc act tgt atc ctg gac agg cgg cct      96
Ser Glu Trp Gly Ile Pro Cys Ala Thr Cys Ile Leu Asp Arg Arg Pro
             20                  25                  30 gcc tcg tgt ggc acc tgt gtg agg gac tgc tgg ccc gag acc ggg tcg     144
Ala Ser Cys Gly Thr Cys Val Arg Asp Cys Trp Pro Glu Thr Gly Ser
         35                  40                  45 gta cgt ttc cca ttc cac agg tgt ggc gcg gga ccg agg ctg acc aga     192
Val Arg Phe Pro Phe His Arg Cys Gly Ala Gly Pro Arg Leu Thr Arg
     50                  55                  60 gac ctt gag gct gtg ccc ttc gtc aat agg aca act ccc ttc acc ata     240
Asp Leu Glu Ala Val Pro Phe Val Asn Arg Thr Thr Pro Phe Thr Ile
 65                  70                  75                  80 agg ggg ccc ctg ggc aac cag ggg cga ggc aac ccg gtg cgg tcg ccc     288
Arg Gly Pro Leu Gly Asn Gln Gly Arg Gly Asn Pro Val Arg Ser Pro
                 85                  90                  95 ttg ggt ttt ggg tcc tac acc atg acc aag atc cga gac tcc tta cac     336
Leu Gly Phe Gly Ser Tyr Thr Met Thr Lys Ile Arg Asp Ser Leu His
            100                 105                 110 ttg gtg aaa tgt ccc acc cca gcc att gag cct ccc acc gga acg ttt     384
Leu Val Lys Cys Pro Thr Pro Ala Ile Glu Pro Pro Thr Gly Thr Phe
        115                 120                 125 ggg ttc ttc cca gga gtc ccc ccc ctt aac aac tgc atg ctt ctc ggc     432
Gly Phe Phe Pro Gly Val Pro Pro Leu Asn Asn Cys Met Leu Leu Gly
    130                 135                 140 act gag gtg tca gag gta ttg ggt ggg gcg ggc ctc act ggg ggg ttt     480
Thr Glu Val Ser Glu Val Leu Gly Gly Ala Gly Leu Thr Gly Gly Phe
145                 150                 155                 160 tac gaa cct ctg gtg cgg cgg tgt tca gag ctg atg ggt cgg cgg aat     528
Tyr Glu Pro Leu Val Arg Arg Cys Ser Glu Leu Met Gly Arg Arg Asn
                165                 170                 175 ccg gtc tgc ccg ggg ttt gca tgg ctc tct tcg gga cgg cct gat ggg     576
Pro Val Cys Pro Gly Phe Ala Trp Leu Ser Ser Gly Arg Pro Asp Gly
            180                 185                 190 ttc ata cat gtt cag ggc cac ttg cag gag gtg gat gcg ggc aac ttc     624
Phe Ile His Val Gln Gly His Leu Gln Glu Val Asp Ala Gly Asn Phe
        195                 200                 205 att ccg ccc cca cgc tgg ttg ctc ttg gac ttt gta ttt gtc ctg tta     672
Ile Pro Pro Pro Arg Trp Leu Leu Leu Asp Phe Val Phe Val Leu Leu
    210                 215                 220 tac ctg atg aag ctg gca gag gca cgg ttg gtc ccg ctg atc ctc ctc     720
Tyr Leu Met Lys Leu Ala Glu Ala Arg Leu Val Pro Leu Ile Leu Leu
225                 230                 235                 240
```

-continued

| | | | | | | | | | | | | | | | | |
|---|---|---|---|---|---|---|---|---|---|---|---|---|---|---|---|---|
| ctg | cta | tgg | tgg | tgg | gtg | aac | cag | ttg | gcg | gtc | ctt | gkt | gtg | scg | gct | 768 |
| Leu | Leu | Trp | Trp | Trp | Val | Asn | Gln | Leu | Ala | Val | Leu | Xaa | Val | Xaa | Ala | |
| | | | 245 | | | | | 250 | | | | | 255 | | | |
| gck | crc | gcc | gcc | gtg | gct | gga | gag | gtt | ttt | gcg | ggc | cct | gcc | ttg | tcc | 816 |
| Xaa | Xaa | Ala | Ala | Val | Ala | Gly | Glu | Val | Phe | Ala | Gly | Pro | Ala | Leu | Ser | |
| | | | 260 | | | | | 265 | | | | | 270 | | | |
| tgg | tgt | ctg | ggc | cta | ccc | ttc | gtg | agt | atg | atc | ctg | ggg | cta | gca | aac | 864 |
| Trp | Cys | Leu | Gly | Leu | Pro | Phe | Val | Ser | Met | Ile | Leu | Gly | Leu | Ala | Asn | |
| | | | 275 | | | | | 280 | | | | | 285 | | | |
| ctg | gtg | ttg | tac | ttc | cgc | tgg | atg | ggt | cct | caa | cgc | ctg | atg | ttc | ctc | 912 |
| Leu | Val | Leu | Tyr | Phe | Arg | Trp | Met | Gly | Pro | Gln | Arg | Leu | Met | Phe | Leu | |
| | | | 290 | | | | | 295 | | | | | 300 | | | |
| gtg | ttg | tgg | aag | ctc | gct | cgg | ggg | | | | | | | | | 936 |
| Val | Leu | Trp | Lys | Leu | Ala | Arg | Gly | | | | | | | | | |
| 305 | | | | 310 | | | | | | | | | | | | |

<210> SEQ ID NO 4
<211> LENGTH: 312
<212> TYPE: PRT
<213> ORGANISM: Hepatitis GB virus C
<220> FEATURE:
<221> NAME/KEY: MOD_RES
<222> LOCATION: (253)..(258)
<223> OTHER INFORMATION: X = anything

<400> SEQUENCE: 4

Thr Ile Ala Ala Leu Gly Ser Ser Asp Arg Asp Thr Val Val Glu Leu
 1               5                  10                  15

Ser Glu Trp Gly Ile Pro Cys Ala Thr Cys Ile Leu Asp Arg Arg Pro
             20                  25                  30

Ala Ser Cys Gly Thr Cys Val Arg Asp Cys Trp Pro Glu Thr Gly Ser
         35                  40                  45

Val Arg Phe Pro Phe His Arg Cys Gly Ala Gly Pro Arg Leu Thr Arg
     50                  55                  60

Asp Leu Glu Ala Val Pro Phe Val Asn Arg Thr Thr Pro Phe Thr Ile
 65                  70                  75                  80

Arg Gly Pro Leu Gly Asn Gln Gly Arg Gly Asn Pro Val Arg Ser Pro
                 85                  90                  95

Leu Gly Phe Gly Ser Tyr Thr Met Thr Lys Ile Arg Asp Ser Leu His
            100                 105                 110

Leu Val Lys Cys Pro Thr Pro Ala Ile Glu Pro Pro Thr Gly Thr Phe
        115                 120                 125

Gly Phe Phe Pro Gly Val Pro Pro Leu Asn Asn Cys Met Leu Leu Gly
130                 135                 140

Thr Glu Val Ser Glu Val Leu Gly Gly Ala Gly Leu Thr Gly Gly Phe
145                 150                 155                 160

Tyr Glu Pro Leu Val Arg Arg Cys Ser Glu Leu Met Gly Arg Arg Asn
                165                 170                 175

Pro Val Cys Pro Gly Phe Ala Trp Leu Ser Ser Gly Arg Pro Asp Gly
            180                 185                 190

Phe Ile His Val Gln Gly His Leu Gln Glu Val Asp Ala Gly Asn Phe
        195                 200                 205

Ile Pro Pro Pro Arg Trp Leu Leu Leu Asp Phe Val Phe Val Leu Leu
    210                 215                 220

Tyr Leu Met Lys Leu Ala Glu Ala Arg Leu Val Pro Leu Ile Leu Leu
225                 230                 235                 240

Leu Leu Trp Trp Trp Val Asn Gln Leu Ala Val Leu Xaa Val Xaa Ala
                245                 250                 255

```
Xaa Xaa Ala Ala Val Ala Gly Glu Val Phe Ala Gly Pro Ala Leu Ser
        260                 265                 270

Trp Cys Leu Gly Leu Pro Phe Val Ser Met Ile Leu Gly Leu Ala Asn
        275                 280                 285

Leu Val Leu Tyr Phe Arg Trp Met Gly Pro Gln Arg Leu Met Phe Leu
    290                 295                 300

Val Leu Trp Lys Leu Ala Arg Gly
305                 310

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 5

Leu Thr Gly Gly Phe Tyr Glu Pro Leu
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 6

Gly Gly Ala Gly Leu Thr Gly Gly Phe Tyr Glu Pro Leu Val Arg Arg
1               5                   10                  15

Cys

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 7

Leu Thr Gly Gly Phe Tyr Glu Pro Leu Val Arg Arg Cys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 8

Phe Tyr Glu Pro Leu Val Arg Arg Cys
1               5

<210> SEQ ID NO 9
<211> LENGTH: 415
<212> TYPE: PRT
<213> ORGANISM: Hepatitis GB virus C

<400> SEQUENCE: 9

Val Gly Tyr Val Trp Asp Leu Trp Glu Trp Ile Met Arg Gln Val Arg
```

-continued

```
  1               5              10              15
Met Val Met Ala Arg Leu Arg Ala Leu Cys Pro Val Val Ser Leu Pro
             20              25              30
Leu Trp His Cys Gly Glu Gly Trp Ser Gly Glu Trp Leu Leu Asp Gly
             35              40              45
His Val Glu Ser Arg Cys Leu Cys Gly Cys Val Ile Thr Gly Asp Val
             50              55              60
Leu Asn Gly Gln Leu Lys Glu Pro Val Tyr Ser Thr Lys Leu Cys Arg
 65              70              75              80
His Tyr Trp Met Gly Thr Val Pro Val Asn Met Leu Gly Tyr Gly Glu
             85              90              95
Thr Ser Pro Leu Leu Ala Ser Asp Thr Pro Lys Val Val Pro Phe Gly
            100             105             110
Thr Ser Gly Trp Ala Glu Val Val Thr Pro Thr His Val Val Ile
            115             120             125
Arg Arg Thr Ser Ala Tyr Lys Leu Leu Arg Gln Gln Ile Leu Ser Ala
            130             135             140
Ala Val Ala Glu Pro Tyr Tyr Val Asp Gly Ile Pro Val Ser Trp Asp
145             150             155             160
Ala Asp Ala Arg Ala Pro Ala Met Val Tyr Gly Pro Gly Gln Ser Val
            165             170             175
Thr Ile Asp Gly Glu Arg Tyr Thr Leu Pro His Gln Leu Arg Leu Arg
            180             185             190
Asn Val Ala Pro Ser Glu Val Ser Glu Val Ser Ile Asp Ile Gly
            195             200             205
Thr Glu Thr Glu Asp Ser Glu Leu Thr Glu Ala Asp Leu Pro Pro Ala
            210             215             220
Ala Ala Ala Leu Gln Ala Ile Glu Asn Ala Ala Arg Ile Leu Glu Pro
225             230             235             240
His Ile Asp Val Ile Met Glu Asp Cys Ser Thr Pro Ser Leu Cys Gly
            245             250             255
Ser Ser Arg Glu Met Pro Val Trp Gly Glu Asp Ile Pro Arg Thr Pro
            260             265             270
Ser Ser Pro Ala Leu Ile Ser Val Thr Glu Ser Pro Ser Asp Glu Lys
            275             280             285
Thr Pro Ser Val Ser Ser Gln Glu Asp Thr Pro Ser Ser Asp Ser
            290             295             300
Phe Glu Val Ile Gln Glu Ser Glu Thr Ala Glu Gly Glu Glu Ser Val
305             310             315             320
Phe Asn Val Ala Leu Ser Val Leu Lys Ala Leu Phe Pro Gln Ser Asp
            325             330             335
Ala Thr Arg Lys Leu Thr Val Lys Met Ser Cys Cys Val Glu Lys Ser
            340             345             350
Val Thr Arg Phe Phe Ser Leu Gly Leu Thr Val Ala Asp Val Ala Ser
            355             360             365
Leu Cys Glu Met Glu Ile Gln Asn His Thr Ala Tyr Cys Asp Lys Val
            370             375             380
Arg Thr Pro Leu Glu Leu Gln Val Gly Cys Leu Val Gly Asn Glu Leu
385             390             395             400
Thr Phe Glu Cys His Asn Cys Glu Ala Arg Gln Glu Thr Leu Ala
            405             410             415
```

FLAVIVIRUS NS5A PROTEINS FOR THE TREATMENT OF HIV

BACKGROUND OF THE INVENTION

The present application claims benefit of priority to U.S. Provisional Application Ser. No. 60/653,823, filed Feb. 17, 2005, the entire contents of which are hereby incorporated by reference.

The U.S. Government own rights in this invention pursuant to grant number AI58740 from NIH and merit grants awarded to Jack Stapleton and Jinhua Xiang from the Veterans Administration.

I. Field of the Invention

The present invention relates generally to the fields of molecular biology and virology. More particularly, it concerns methods and compositions to treat, inhibit or prevent HIV infection.

II. Description of Related Art

A. GB Virus Type C

GB virus type C (GBV-C), also known as hepatitis G virus (HGV), is a virus whose genomic organization and nucleotide sequence places it in the Flavivirus family (Robertson et al., 1998). It is the most closely related human virus to hepatitis C virus (HCV) (Leary et al., 1996; Linnen et al., 1996; Simons et al., 1995). It has been suggested that these viruses should be classified together with non-human GB-hepatitis agents as the hepacivirus genus. Although GBV-C was originally associated with post-transfusion hepatitis in humans (Linnen et al., 1996), subsequent epidemiological studies indicated that it does not cause acute or chronic hepatitis (Alter et al., 1997a; Alter et al., 1997b). In addition, experimental GBV-C infection of chimpanzees was not associated with acute hepatitis (Bukh et al., 1998).

Persistent GBV-C viremia (as detected by RT-PCR) is common, with 0.9% to 3% of healthy U.S. blood donors and approximately 20%-30% of patients with HCV infection persistently infected with GBV-C (Dawson et al., 1996; Feucht et al., 1997; Simons et al., 1995a; Simons et al., 1995b; Tacke et al., 1997). Following infection, about 80% of people clear their viremia, concomitantly developing antibody to the GBV-C E2 protein (Feucht et al., 1997; Thomas et al., 1998). Thus, it is estimated that approximately 20% of infected people remain viremic for long periods of time. GBV-C appears to be transmitted primarily by parenteral exposure (Simons et al., 1995), although there are data suggesting that sexual and/or household transmission of GBV-C infection may occur (Akiyoshi et al., 1999; de Martino et al., 1998; Nerurkar et al., 1998; Tanaka et al., 1997; Wu et al., 1997).

B. GBV-C and HIV

During progressive human immunodeficiency virus type 1 (HIV-1) infection, the virus-specific immune responses of an infected subject gradually deteriorate, leading to the development of acquired immunodeficiency syndrome (AIDS). Most infected patients do not exhibit overt clinical manifestations of the disease for six to ten years following initial infection, however, most individuals infected with HIV eventually die from conditions or infections; that the individual's immune system is no longer equipped to fight. While treatment for AIDS has been forthcoming, no effective cure has been reported. Thus, preventative and treatment options against HIV infection and the development of AIDS remain highly desirable.

GBV-C has been investigated in the context of HIV infection. The course of HIV-1 infection is extremely variable among infected individuals, although the reasons for this observation are not fully understood. Individuals whose HIV disease progresses slowly are often called long-term non-progressors (LTNPs). The prevalence of LTNPs varies from 1% to 25% of infected people, depending upon the definition used (reviewed in Easterbrook, 1999). There are no specific clinical criteria for LTNP. However, non-progression generally implies the absence of HIV-related clinical disease 10 or more years following infection and an absolute CD4 count of $\geq 500$ cells/mm$^3$ (Easterbrook, 1999). Evaluation of LTNP's has identified HIV isolates with deletions in key replicative genes (Deacon et al., 1995) and host genetic factors, including specific HLA haplotypes (reviewed in reference Rowland-Jones, 1999). In some individuals, polymorphisms that result in absent or reduced expression of HIV co-receptors have been identified (Huang et al., 1996). However, these findings are uncommon and thought to account for no more than one-third of LTNP's (Rowland-Jones, 1999).

Persistent GBV-C infection is common in humans, with infection rates of approximately 0.9% to 3% in healthy blood donors, 20-30% in HCV-positive people (Dawson et al., 1996), and 35%-40% in HIV-positive individuals. GBV-C infection can persist for decades in the absence of any clinical morbidity or mortality. Among immune-competent individuals, it is estimated that 60% to 75% of GBV-C-infected people clear the infection, concomitantly developing antibodies to the envelope glycoprotein E2 (Thomas et al., 1998). It is also known that GBV-C can be propagated in cultures of peripheral blood mononuclear cells (PBMC's) (Fogeda et al., 1999).

In 1998, Toyoda et al. found that hemophiliacs co-infected with HIV and GBV-C had a lower plasma HIV RNA concentration and a lower incidence of AIDS diagnoses compared to those infected with HIV alone (Toyoda et al., 1998), although the differences were not statistically significant. In contrast, Sabin and colleagues found an increased rate of AIDS and death in hemophiliacs "exposed" to GBV-C (Sabin et al., 1998) compared to non-exposed individuals. This study included HIV-positive subjects who were either GBV-C viremic as determined by detection of GBV-C RNA in plasma, or HIV-infected people who were not viremic but were anti-GBV-C E2 antibody-positive. Although the mortality rate was higher among the GBV-C "exposed" individuals, the results were not statistically significant. Looking at HIV-infected persons, Lefrere and colleagues reported a significant delay in the rate of CD4+ T cell decline, development of AIDS, and death in 23 HIV-positive individuals with GBV-C viremia compared to 72 HIV-infected people without GBV-C viremia (Lefrère et al., 1999). In that study, HIV-infected individuals who were also GBV-C-positive were compared to HIV-infected individuals who were GBV-C-negative. When these subjects were matched by age, sex, baseline HIV RNA load, and baseline CD4 T cell count, HIV disease progression appeared to be worse in GBV-C-negative subjects.

The interrelationship between HIV and GBV-C continues to be explored, with possible therapeutic aspects of GBV-C infection being examined.

SUMMARY OF THE INVENTION

A pharmaceutical composition comprising an isolated flavivirus NS5A peptide or polypeptide, or multiple flavivirus NS5A peptides from the same or different NS5A polypeptide. The NS5A polypeptide may be a full length NS5A polypeptide, a fusion polypeptide. The fusion may comprise a targeting signal, such as a nuclear targeting signal or a cell surface receptor (e.g., a CD4 receptor). The NS5A peptide or polypeptide may be formulated in a lipid vehicle, such a liposome. The NS5A peptide or polypeptide may be formulated with an amphipathic peptide, an insect peptide, or pyrrhocoricin. The flavivirus may be selected from the group consisting of DEN4, YFV, TBEV, WNV, CSFV, BVDV, GBV-A, GBV-B, GBV-C, HGV, HCV2a, HCV3a, HCV2b, HCV1a and HCV1b. The flavivirus NS5A peptide or polypeptide may residues 152-237 of GBV-C NS5A, or the corresponding sequences thereto from other flavivirus NS5A proteins, or may comprise domain II of HCV NS5A, or the corresponding sequences thereto from other flavivirus NS5A proteins. The NS5A peptide or polypeptide may be from a IFN-sensitive flavivirus, or a IFN-resistant flavivirus. The IFN-sensitive flavivirus or IFN-resistant flavivirus may be a GBV-C virus.

In yet another embodiment, there is provided a method for preventing or treating HIV infection comprising administering to a subject a composition comprising a flavivirus NS5A peptide or polypeptide. The flavivirus NS5A peptide or polypeptide comprises multiple flavivirus NS5A peptides, from the same or different NS5A polypeptides. The NS5A polypeptide may be a full length NS5A polypeptide, and may be a fusion polypeptide, for example, comprising a targeting signal, such as a nuclear targeting signal or a targeting signal that targets a cell surface receptor (e.g., the CD4 receptor). The NS5A peptide or polypeptide may be formulated in a lipid vehicle, such a liposome. The NS5A peptide or polypeptide may be formulated with an amphipathic peptide, an insect peptide, or pyrrhocoricin. The flavivirus may be selected from the group consisting of DEN4, YFV, TBEV, WNV, CSFV, BVDV, GBV-A, GBV-B, GBV-C, HGV, HCV2a, HCV3a, HCV2b, HCV1a and HCV1b. The flavivirus NS5A peptide or polypeptide may residues 152-237 of GBV-C NS5A, or the corresponding sequences thereto from other flavivirus NS5A proteins, or may comprise domain II of HCV NS5A, or the corresponding sequences thereto from other flavivirus NS5A proteins. The NS5A peptide or polypeptide may be from a IFN-sensitive flavivirus, or a IFN-resistant flavivirus. The IFN-sensitive flavivirus or IFN-resistant flavivirus may be a GBV-C virus. The method may further comprise administration of at least a second anti-HIV therapy, before or after said flavivirus NS5A peptide or polypeptide. The second anti-HIV therapy may be HAART therapy, or AZT therapy. The method may comprise multiple administrations of the composition.

In yet another embodiment, there is provided a method of reducing HIV replication in an HIV-infected cell comprising contacting said cell with a composition comprising a flavivirus NS5A peptide or polypeptide. The cell may be a T lymphocyte. In still yet another embodiment, there is provided a method of inhibiting HIV infection of a cell comprising contacting said cell with a composition comprising a flavivirus NS5A peptide or polypeptide. The cell may be a T lymphocyte.

In still a further embodiment, there is provided a method for preventing or treating HIV infection comprising administering to a subject a composition comprising an expression construct encoding a flavivirus NS5A peptide or polypeptide. The expression construct may be a viral expression construct, such as an adenovirus, a retrovirus, a lentivirus, an adeno-associated virus, a polyoma virus, a herpesvirus, or a pox virus. The expression construct may be a non-viral expression construct, for example, dispersed in a lipid vehicle. The expression construct may encode an NS5A polypeptide or an NS5A peptide, a a full length NS5A polypeptide, a fusion polypeptide, for example, comprising a nuclear targeting signal or a signal that targets a cell surface receptor, e.g., the CD4 receptor. The flavivirus NS5A peptide or polypeptide may comprise residues 152-237 of GBV-C NS5A, or the corresponding sequences thereto from other flavivirus NS5A proteins, or domain II of HCV NS5A, or the corresponding sequences thereto from other flavivirus NS5A proteins. The flavivirus may be selected from the group consisting of DEN4, YFV, TBEV, WNV, CSFV, BVDV, GBV-A, GBV-B, GBV-C, HGV, HCV2a, HCV3a, HCV2b, HCV1a and HCV1b.

The use of the word "a" or "an" when used in conjunction with the term "comprising" in the claims and/or the specification may mean "one," but it is also consistent with the meaning of "one or more," "at least one," and "one or more than one." Furthermore, where multiple steps of a method of process are cited, it is understood that the steps are not required to be performed in the particular order recited unless one of skill in the art is not be able to practice the method in a different order.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-C—HIV replication in Jurkat cells with and without NS5A expression. The amount of HIV p24 antigen released into culture supernatants from two cloned Jurkat cell lines expressing GBV-C NS5A (A11a and A11b) or vector control cell line (VC) 2 to 6 days following infection using an X-4 virus isolate (MOI of 0.1 (FIG. 2A) or 0.5 (FIG. 2B)). Cells were grown without doxycycline, and data represent the mean of 3 replicate samples. NS5A expression is shown (immunoblot of cell lysates in triplicate) of A11a, A11b. VC=vector control cell lysate. Note that A11a has greater levels of NS5A expressed and HIV replication in these cells is lower than in A11b (on day 6). Compared to vector control cells, HIV inhibition was significantly lower on day 6 (p=0.02).

Figure 6:
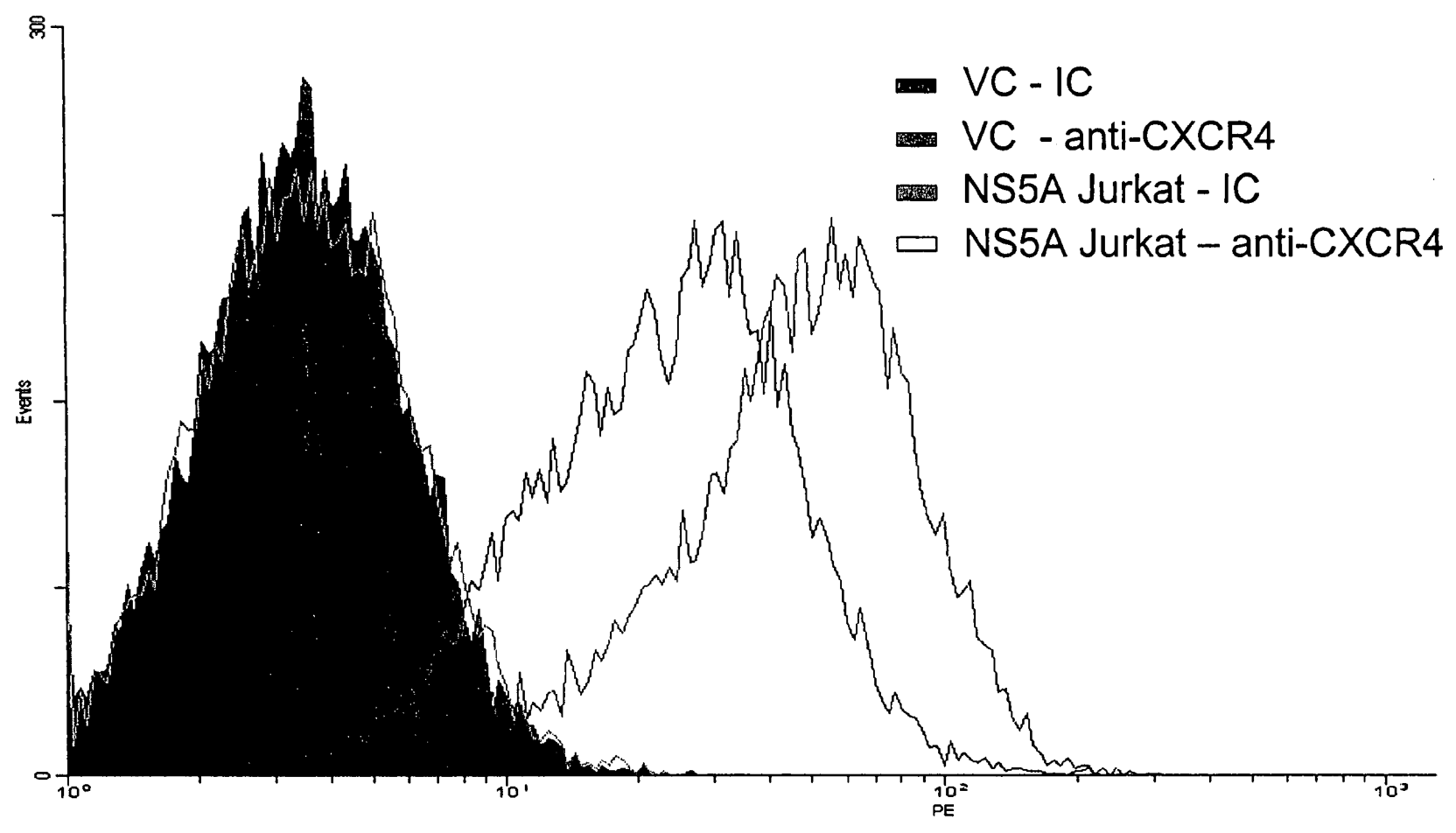

FIG. 6—Jurkat cells expressing GBV-C NS5A have lower surface density of CXCR4 compared to Jurkat cells with a vector control. Jurkat cells that express NS5A or the vector control were grown without doxycycline, and analyzed by flow cytometry for surface expression of CXCR4 (shown above). Reproducibly, cells with NS5A demonstrated a 49.6% reduction in CXCR4 mean fluorescence (p=0.003). No difference in CCR5 or CD4 was observed (data not shown). Preliminary microarray data demonstrated decreased levels of CXCR4 25 mRNA in NS5A expressing cells.

FIGS. 11A-C—NS5A Inhibits Multiple Distinct HIV Strains. HIV replication is measured by p24 antigen levels on days 2-6 (D2-D6). VC-GFP=vector control expression GFP; IFN-R=interferon resistant NS5A; IFN-R-GFP=interferon resistant NS5A linked to GFP; IFN-S-GFP=interferon sensitive NS5A linked to GFP.

FIG. 13—Fragments of NS5A That Inhibit HIV Replication. Shaded bars inhibit HIV; open bars do not inhibit HIV.

FIG. 17—R 152-237 NS5A inhibits HIV when expressed in Jurkat cells. By deduction, it appears that 152-182 is the minimal sequence required for HIV inhibition. Note that the latter sequence is conserved (IFN-R and IFN-S) GBV-C NS5A, and that there are multiple potential phosphorylation sites (SEQ ID NOS:10-13).

DESCRIPTION OF ILLUSTRATIVE EMBODIMENTS

Figure 1:
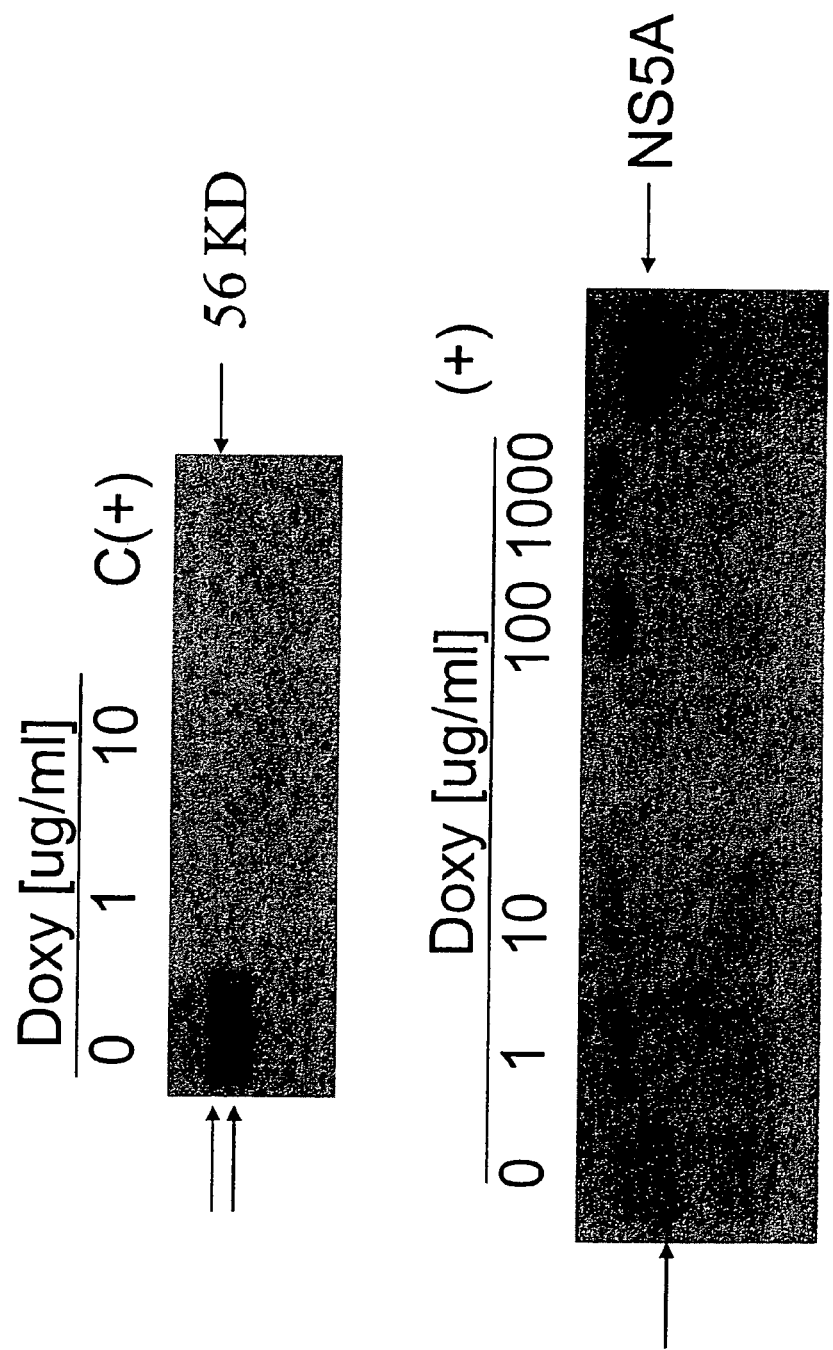
FIG. 1—NS5A expression in Jurkat cells. Jurkat cells containing GBV-C NS5A (A11a clone) expressed two immunoreactive proteins when incubated without doxycycline (Doxy). Rabbit anti-NS5A antisera was raised against NS5A expressed in E. Coli. This antigen is shown as the positive control on lower panel (+), whereas the positive control [C(+)] top panel represents NS5A expressed in CHO cells; JICR In Press). Growth of cells in low levels of doxycycline for 48 hrs reduced NS5A protein levels to non-detectable levels. Doxy concentration in mg/ml.
Figure 3A:
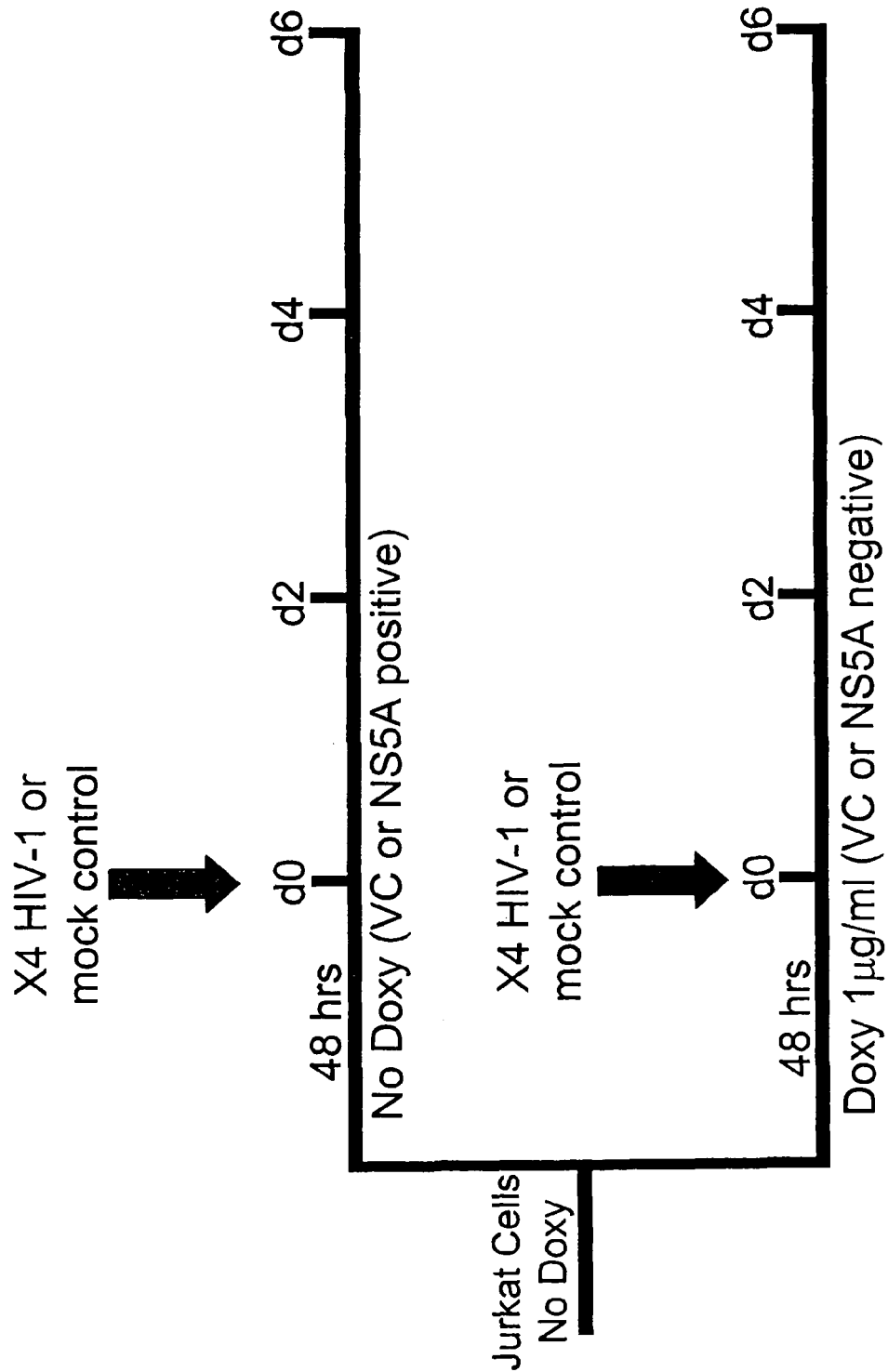
FIG. 3A—Experimental Design. Jurkat cells with either vector control (VC) or NS5A were grown without doxycycline. Cells were divided, and half were maintained without doxycycline (NS5A was expressed) or with various doses of doxycycline (NS5A expression was differentially suppressed). Cells (VC and NS5A containing) were infected with X4 HIV-1 (clinical isolate) 48 hrs after dividing cells, and cell culture supernatants monitored 2, 4, and 6 days later for HIV p24 antigen.
Figure 3B:
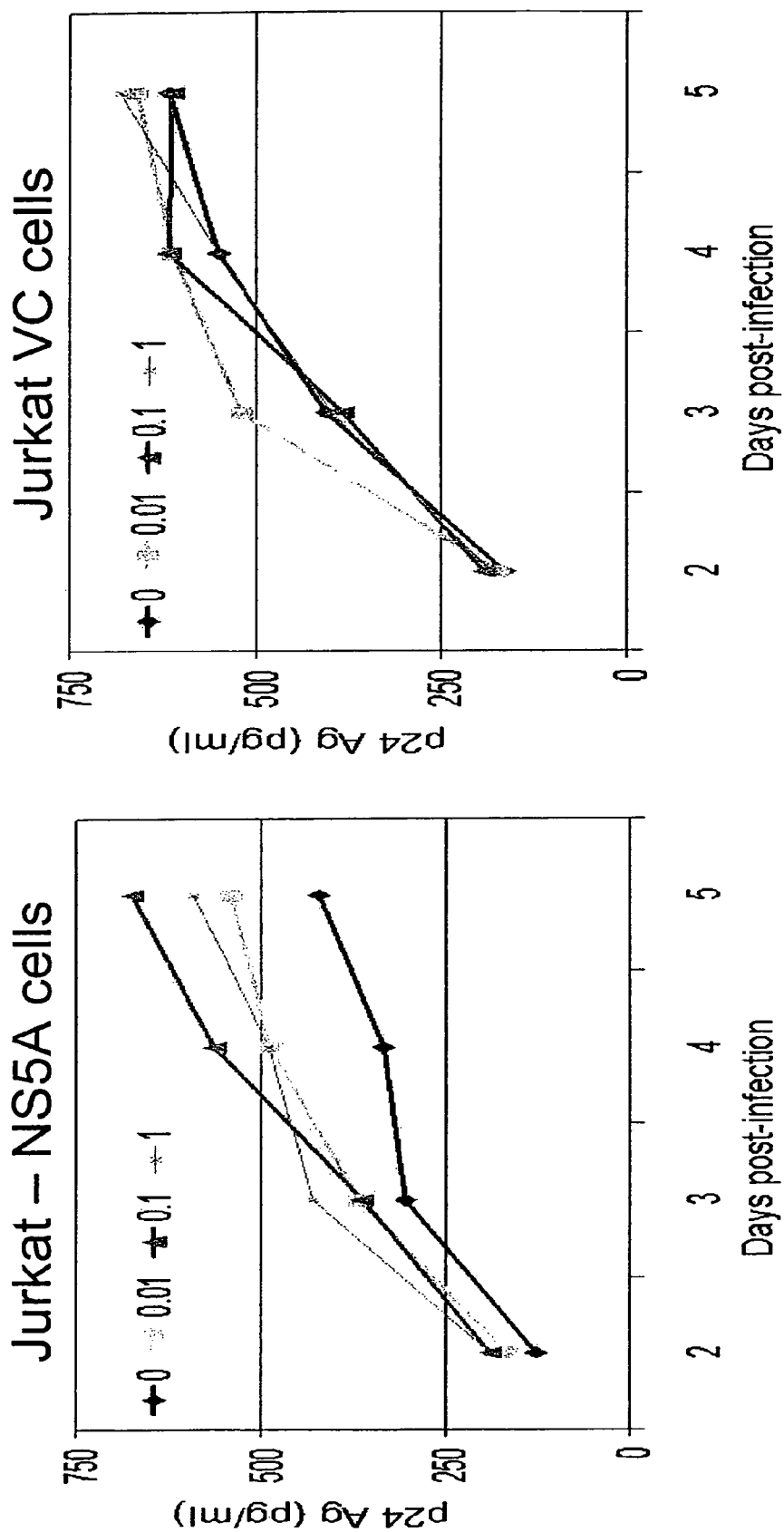
FIG. 3B—Dose-dependent inhibition of HIV by NS5A. Experimental design described above. NS5A expression was suppressed by cell growth in various concentrations of doxycycline (0.01, 0.1 and 1 mg/ml as indicated) for 2 days prior to infection with HIV-1. HIV replication was monitored by measuring p24 antigen in culture supernatants. The amount of NS5A expression was directly correlated with inhibition of HIV expression in Jurkat-NS5A cells (left panel), and doxycycline had no effect in Jurkat-vector control cells (VC; right panel).
Figure 4A:
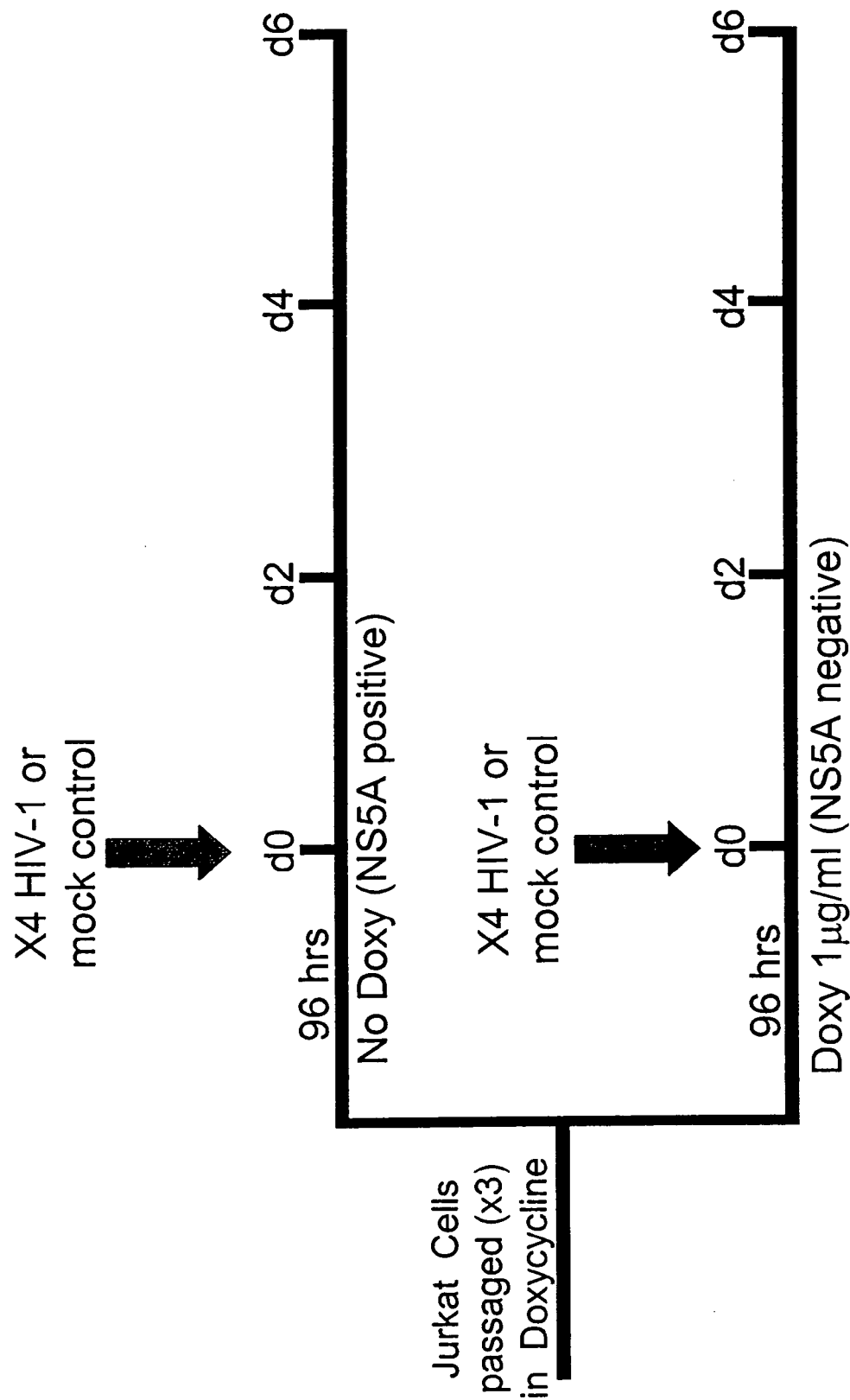
FIG. 4A—Experimental Design. Jurkat cells with NS5A were passaged with doxycycline to suppress NS5A expression. Cells were divided, and half were maintained without doxycycline (NS5A was expressed) or with 1 mg/ml doxycycline (NS5A was not expressed). NS5A containing cells were infected with X4 HIV-1 (clinical isolate) 96 hrs after cells were divided, and cell culture supernatants monitored 2, 4, and 6 days later for HIV p24 antigen.
Figure 4B:
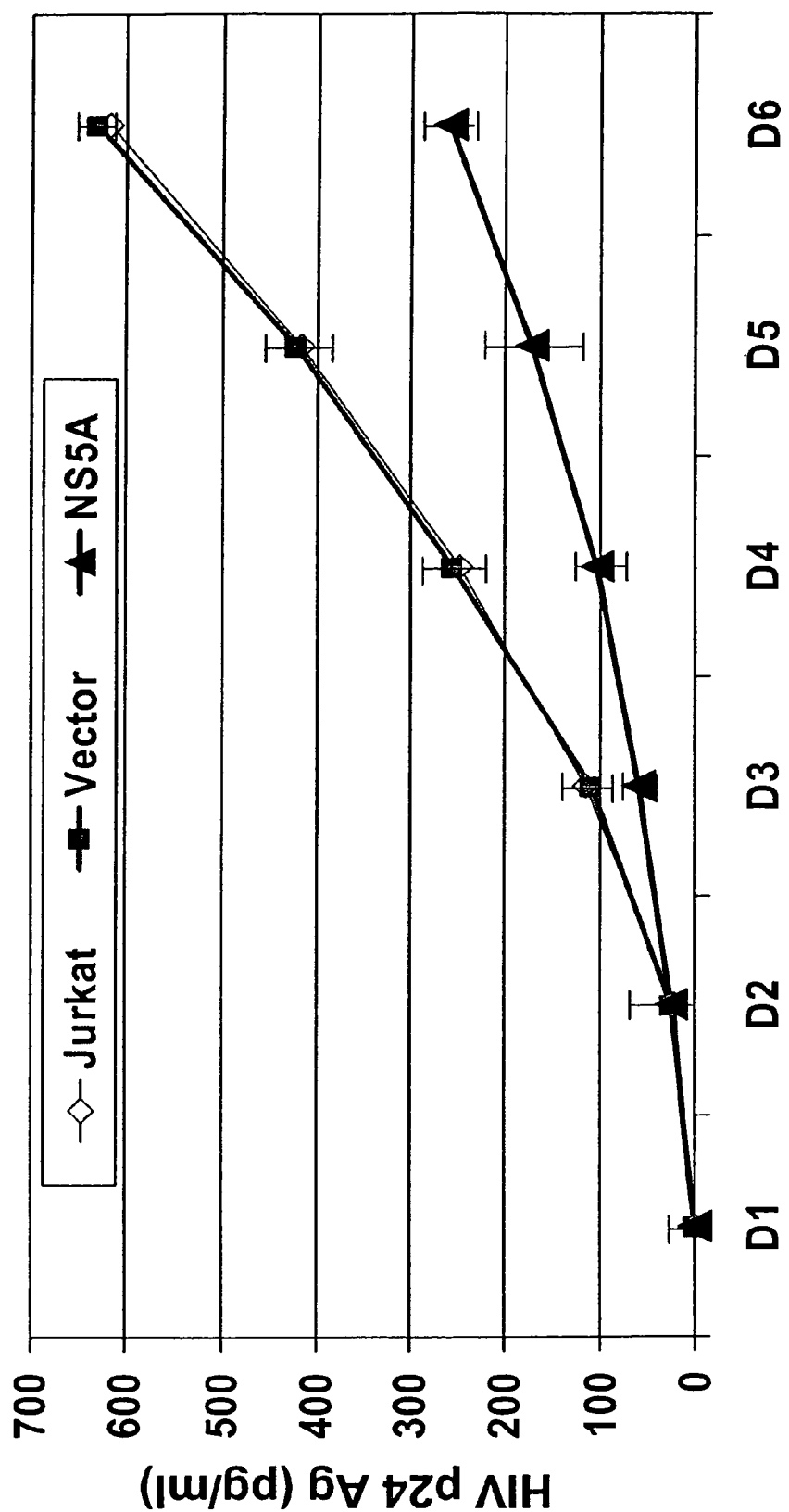
FIG. 4B—GBV-C NS5A inhibits HIV replication. Data represent HIV replication (p24 antigen in supernatants). HIV replication was not different on days 1 and 2; however, by day 3, Jurkat-NS5A cells had 45% reduction in HIV p24 Ag 3 days post-infection (T-test, P=0.03), and by 56%-60% on days 4, 5, and 6 (p<0.001 for each day). Infections were performed in triplicate, NS5A and vector control error bars shown. Results were similar for Jurkat cells without any plasmid DNA as well.
Figure 5:
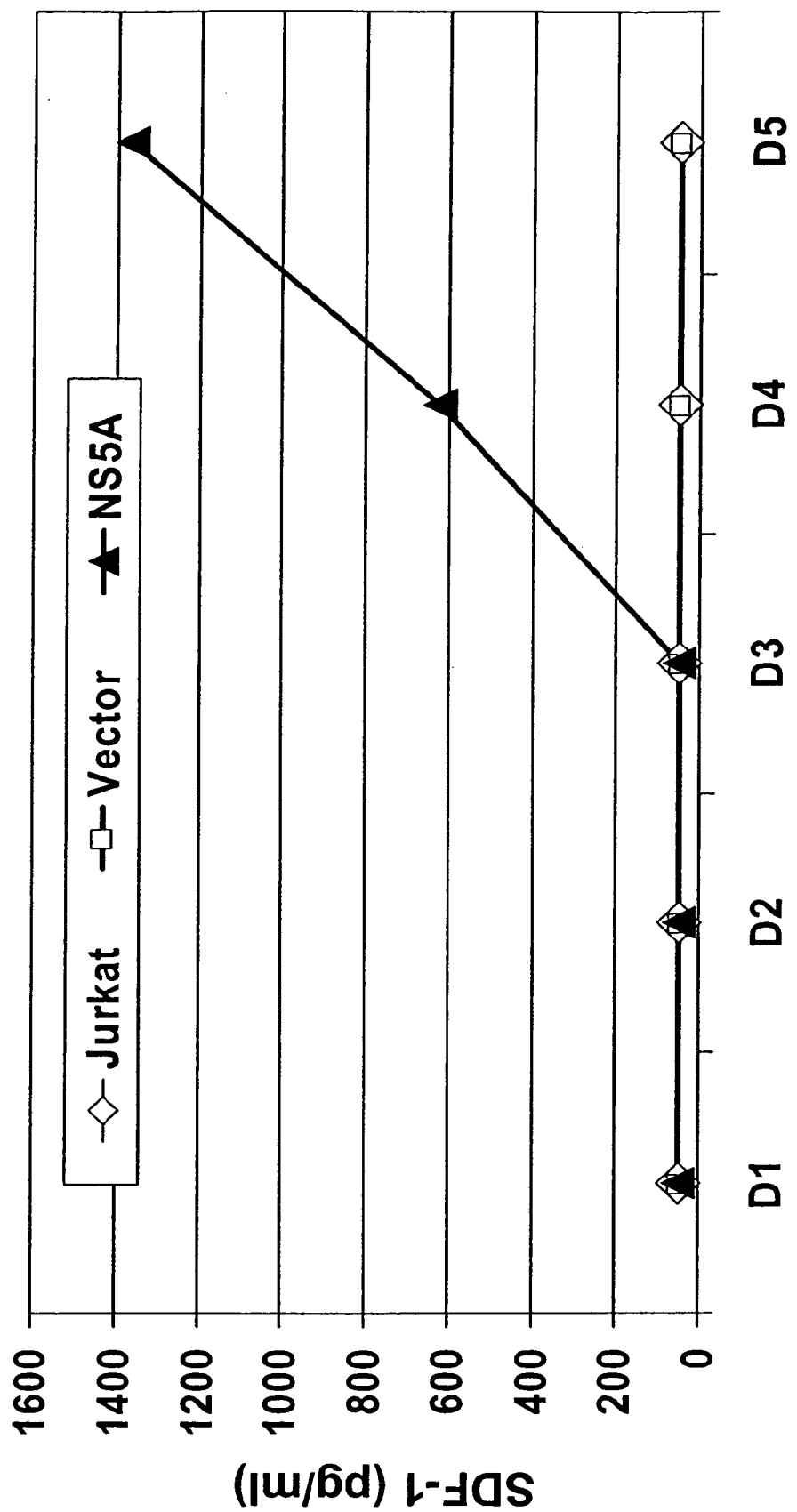
FIG. 5—Release of SDF-1 into culture supernatants by Jurkat cells with or without GBV-C NS5A. SDF-1 in supernatants was measured by ELISA in triplicate at time points shown. There were no differences between Jurkat and vector control Jurkat cells; however, SDF-1 increased in NS5A expressing cells on days 5 and 6 (T test, P<0.001 for both days).
Figure 7:
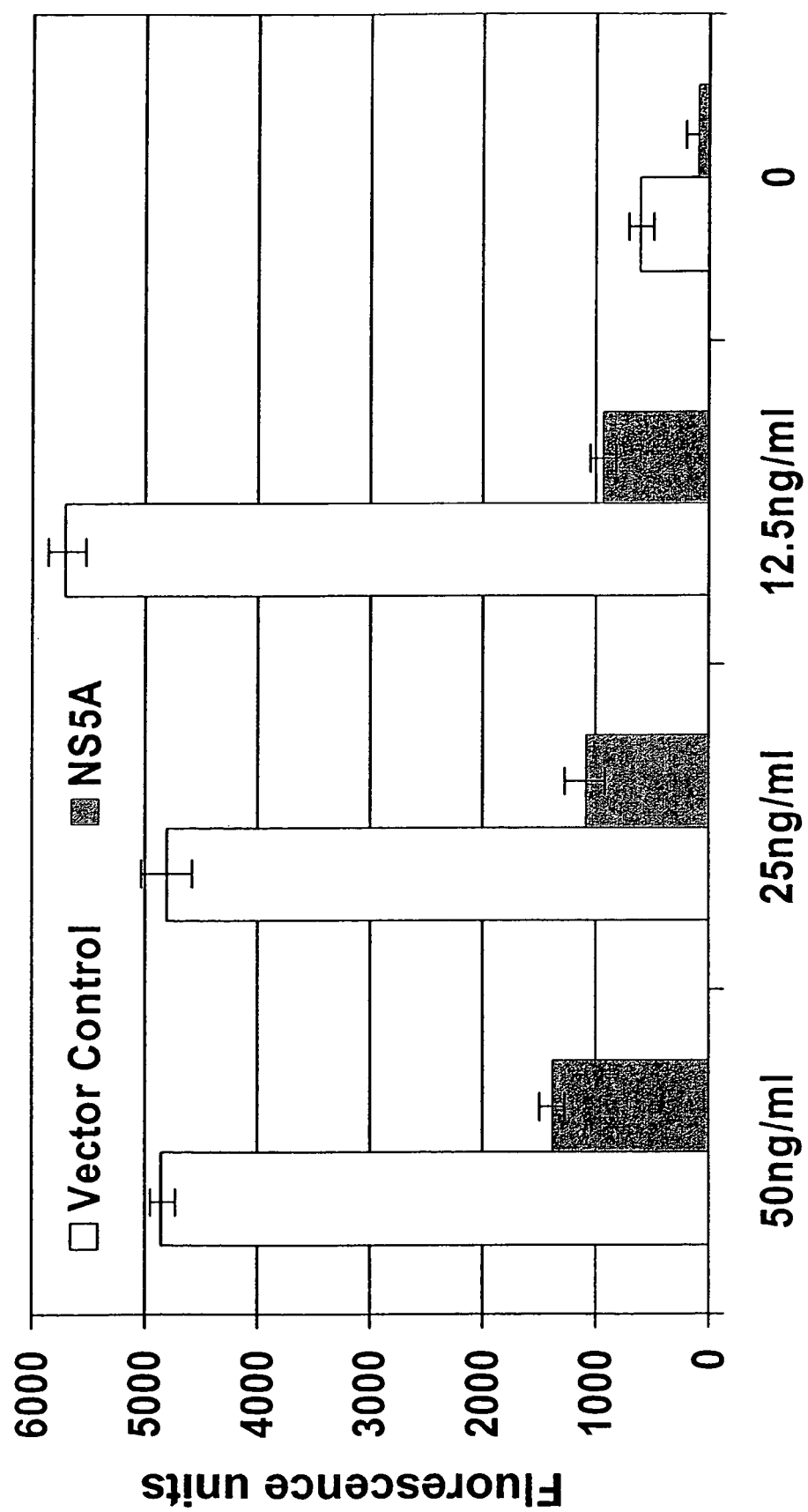
FIG. 7—Release of caspase 3/7 into culture supernants following incubation with anti-Fas antibody (CH11). Jurkat cells with NS5A were relatively resistant to induction of apoptosis by CH11 when compared to Jurkat cells with the vector control. Similarly, spontaneous apoptosis was greater in Jurkat NS5A cells compared to vector control. Preliminary microarray data demonstrated NS5A-related increases in mRNA levels for TGFB1-induced anti-apoptotic factor 1 and chemokine ligand 25 mRNA. Both of these genes enhance resistance to apoptosis, and CC ligand 25 does so in CD4+ T cells.
Figure 8:
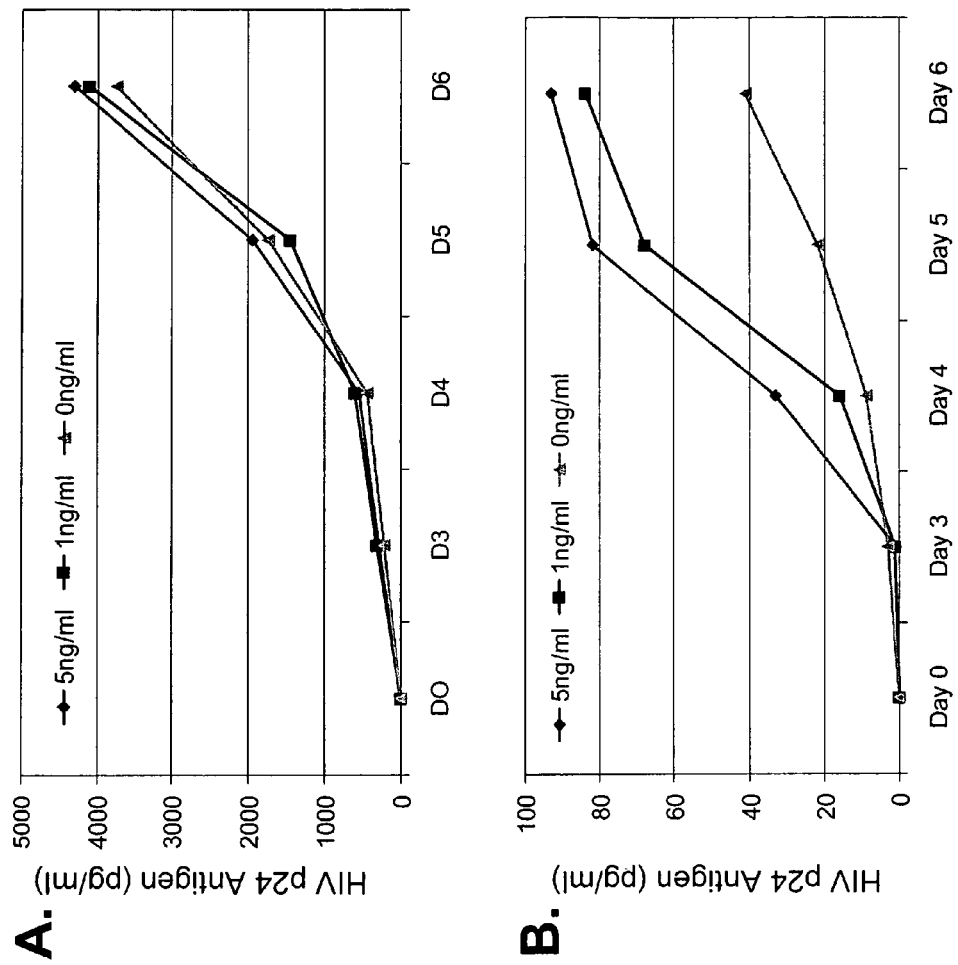
FIG. 8—Dose-Dependent HIV Inhibition by the NS5A Protein. Left panel—NS5A-expressing Jurkat cells; right panel—vector control Jurkat cells. HIV replication is measured by p24 antigen levels on days 2-6 (D2-D6). Amounts of doxycycline, which inversely relate to NS5A production, are shown in μg/ml.
Figure 9:
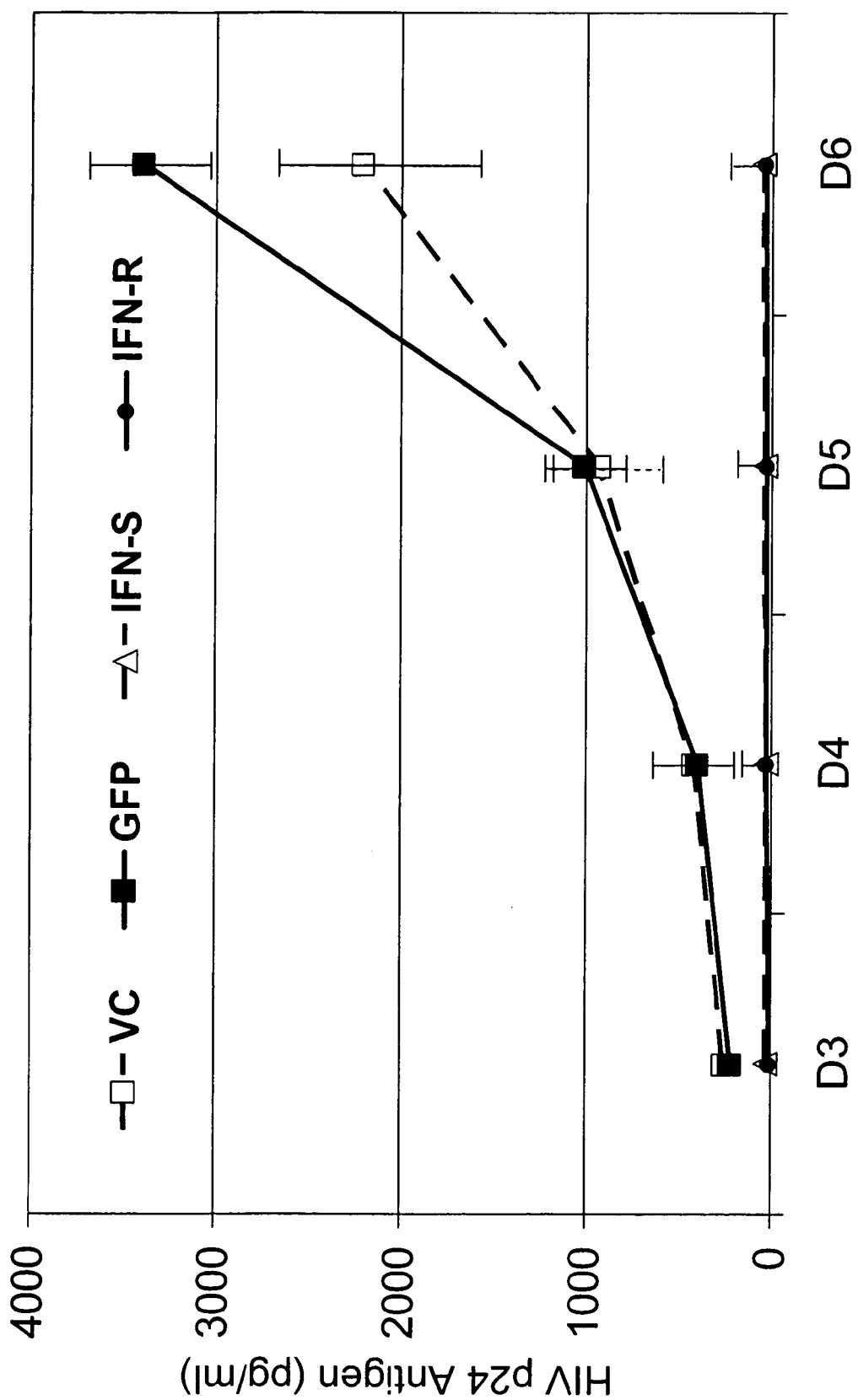
FIG. 9—Both IFN-R and IFN-S GBV-C NS5A Inhibit HIV Replication. HIV replication is measured by p24 antigen levels on days 2-6 (D2-D6). VC=vector control; GFP—vector expression GFP only; IFN-S=interferon sensitive NS5A; IFN-R=interferon resistant NS5A.
Figure 10:
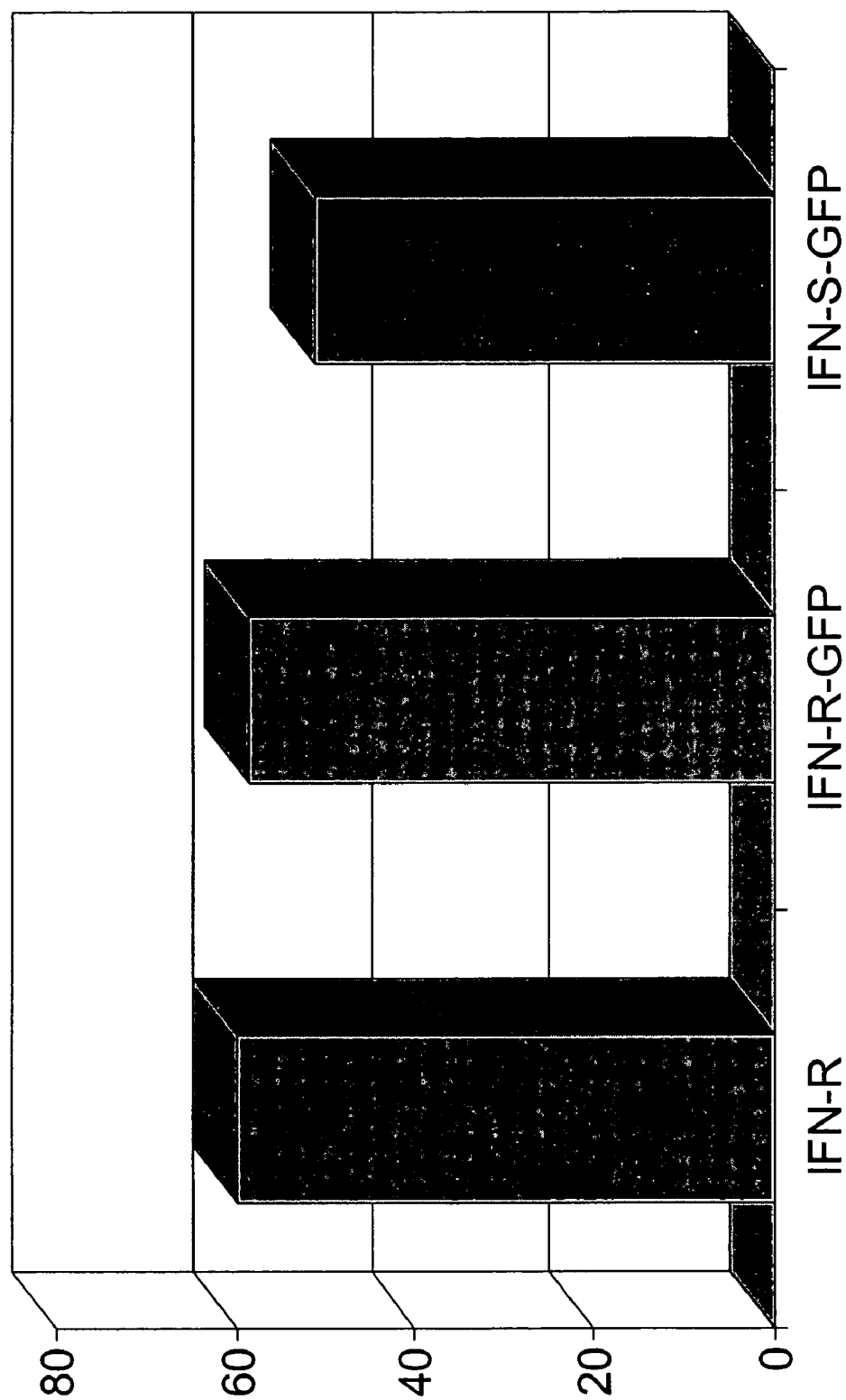
FIG. 10—Anti-SDF-1 Blocks NSF5A-Mediated Inhibition of HIV Replication. Results reported as percent increase in HIV replication when cultures are incubated with anti-SDF-1 neutralizing antibody as compared to isotype control antibody. IFN-R=interferon resistant NS5A; IFN-R-GFP=interferon resistant NS5A linked to GFP; IFN-S-GFP=interferon sensitive NS5A linked to GFP.
Figure 11B:
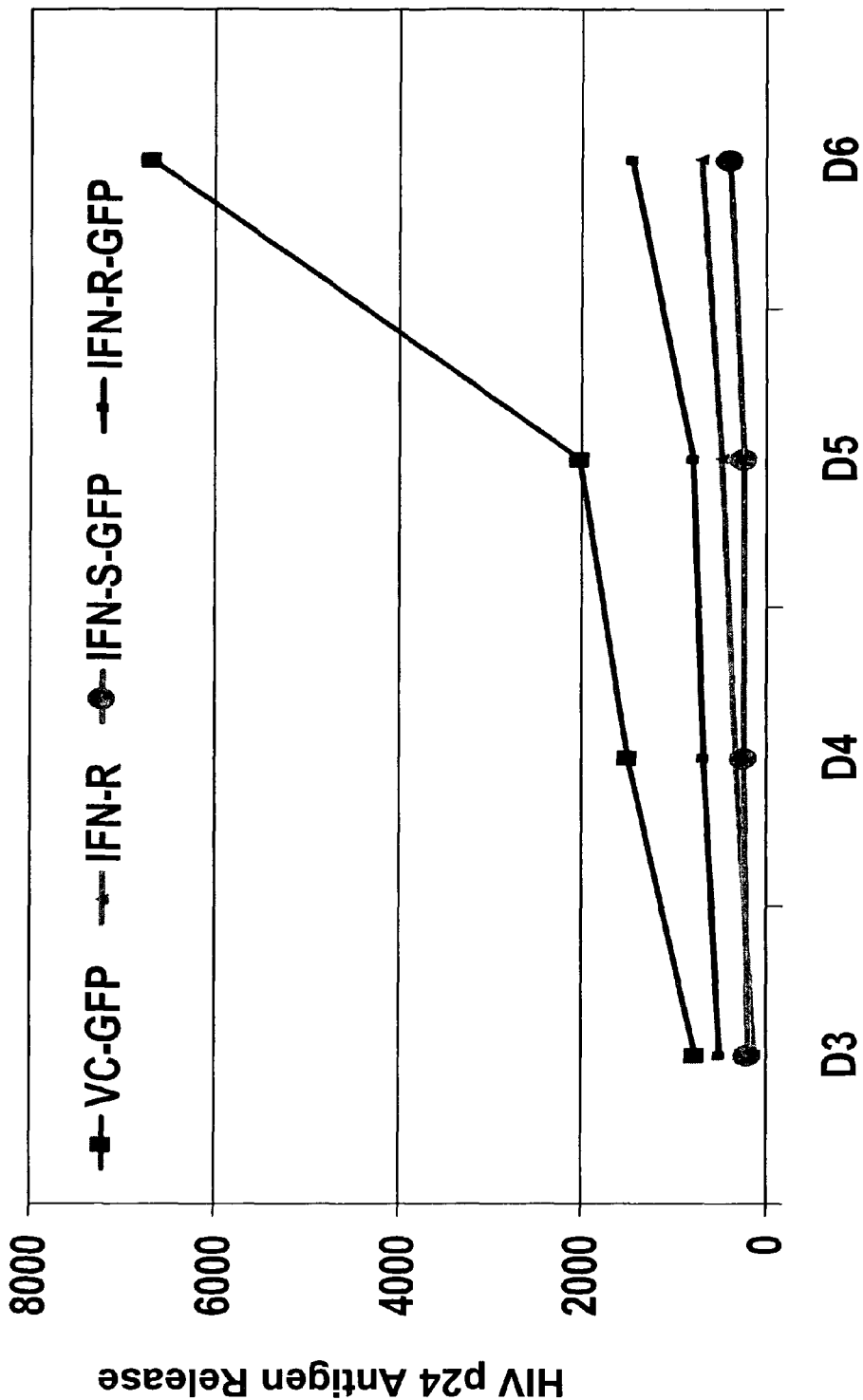
Figure 11C:
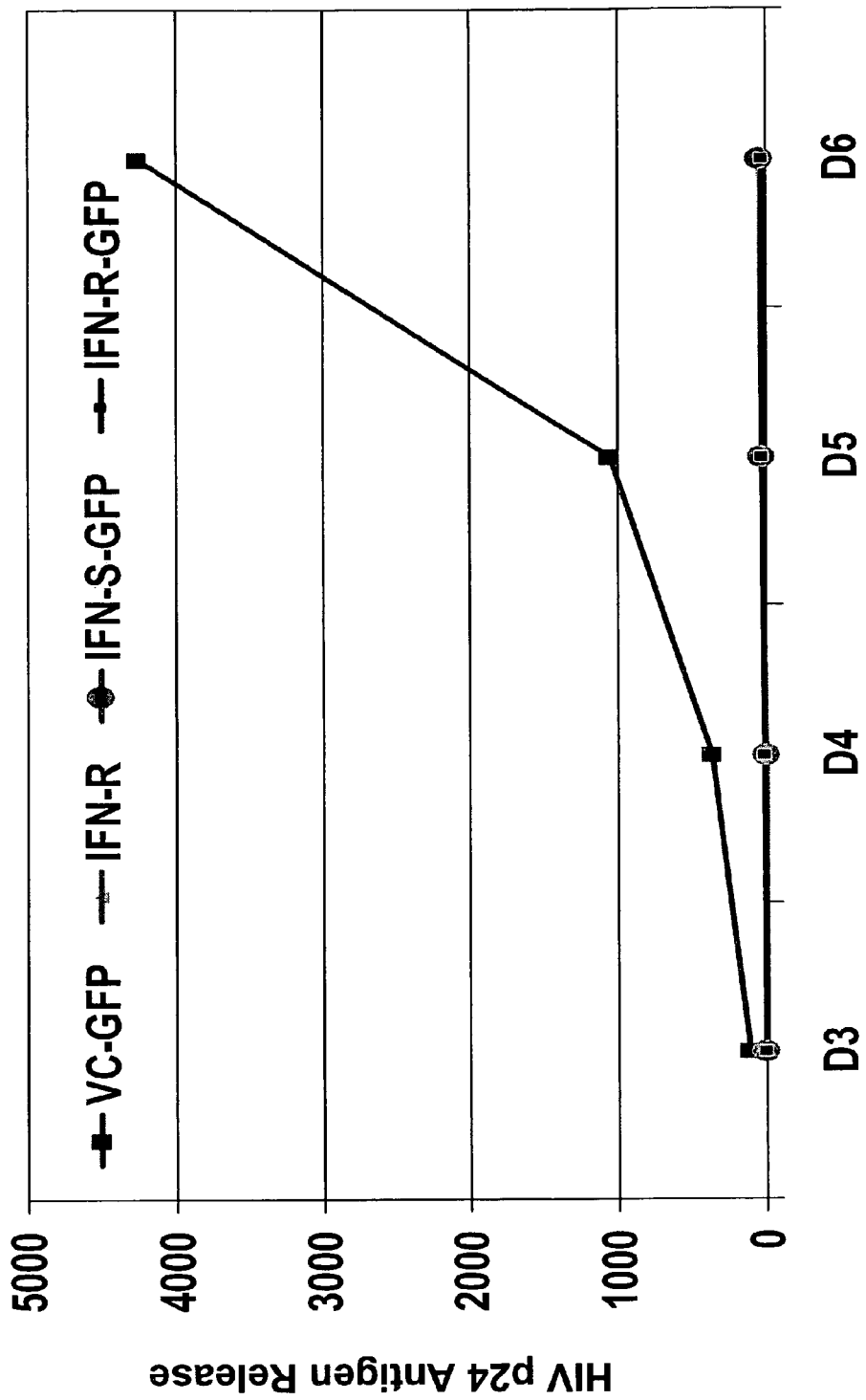

Anti-retroviral medications suppress viral replication in HIV disease, yet they have failed to eradicate the virus from the body due to the multi-faceted nature of HIV infection, as well as the complexities of the immune system. Methods are being developed that both prevent infection and boost the immune system to keep it functioning at a level where it can assist in fighting HIV infection.

The present inventors have previously reported on methods and compositions for therapeutic and/or prophylatic treatment of HIV infection, including GBV-C envelope proteins, in particular GBV-C envelope protein E2 (E2). More specifically, the inventors have shown that HIV-infected subjects that are co-infected with GB virus C (GBV-C) typically have reduced mortality and slower progression to AIDS as compared to HIV-infected subjects without GBV-C co-infection (PCT/US2004/017706). Infection of peripheral blood mononuclear cells (PBMCs) with GBV-C and HIV results in inhibition of HIV-1 replication. GBV-C infection typically inhibits HIV by inducing β-chemokines and reducing expression of the HIV co-receptor CCR5, explaining part of the beneficial clinical findings of GBV-C on HIV disease progression. The inventors also described a therapeutic use for antibodies and/or binding agents that bind GBV-C proteins (e.g., envelope proteins), in particular, the E2 protein, and similar antigens used for producing these antibodies or binding agents (PCT/US03/33925).

The inventors now demonstrate a unique role for the NS5A protein of GBV-C, as well as NS5A's from other flaviviruses, in the inhibition of HIV replication. Various aspects of the invention are described below.

III. Flaviviruses

A. Family

With a total of 69 pathogens in its ranks, Flaviviridae contains a myriad of viruses that cause disease in humans. Foremost among these is Yellow Fever Virus, the type virus of the Flaviviridae, from which the family begets its name (/1avus in Latin means "yellow"). Flaviviruses have been subdivided by the ICTV into three genera: *Flavivirus, Pestivirus* and *Hepacivirus*.

The *Flavivirus* genus contains several dangerous viruses including yellow fever virus, dengue fever virus, and Japanese encaphilitis (JE) virus. The *Pestivirus* genus is home to the three serotypes of bovine viral diarrhea, but no known human pathogens. The genus *Hepacivirus* consists of hepatitis C virus and its relatives.

*Flavivirus* genomes consist of a monopartite (i.e., one piece of) linear, single-stranded, positive sense RNA. Because the RNA is positive sense, the nucleic acid itself is capable of instigating an infection in the appropriate host cells. The total genome can range from 10 to 11 kilobase pairs. The genome 3' terminus is not polyadenylated. The 5' end has a methylated nucleotide cap (allows for translation) or a genome-linked protein (VPg). *Pestivirus* genomes are reported to be 12.5 kb in length. Like the *Flavivirus* genus, no poly-A tail exists on the 3' end of the RNA, however, *Pestivirus* genus members lack a 5' cap. In both genera, structural genes are found towards the 5' end of the RNA. Both the *Pestivirus* and *Hepacivirus* genera contain internal ribosomal entry sites (IRES) that provide a site of translation initiation for host ribosomes. This is in contrast to the *Flavivirus* genus that uses the technique of ribosomal scanning to commence protein synthesis.

Under the EM, virions appear roughly as spheres (some experts say they're "pleomorphic"), 40-65 nm in diameter. What can be seen under the microscope is the virus's lipid envelope, which it obtains from host cells during egress (leaving the cell). Underneath the envelope can be found an icosahedral capsid coat approximately 25-30 nm in diameter.

All members of the *Flavivirus* genus are transmitted by arthropods (i.e., mosquitoes and ticks) while Hepatitis C is spread parenterally (i.e., through contaminated bodily fluids). A key feature for viral transmission in Flaviviruses is that they are capable of reproducing in their vector. Without the ability to replicate in the vector, they would not remain viable to be passed from one host to the next.

B. GBV-C

Like other members of the *Flaviviridae*, GBV-C is a positive-strand RNA virus that encodes a single long open reading frame (Leary et al., 1996). GBV-C does not cause acute or chronic hepatitis, yet it is the family member most closely related to HCV, the cause of hepatitis C. Sequences of GBV-C have been previously reported, for example in U.S. Pat. No. 5,874,563, which is specifically incorporated by reference. In particular, an infectious GBV-C clone has been described in the PCT application WO 01/77157, which is incorporated herein by reference.

The GBV-C polyprotein is predicted to be cleaved into two envelope proteins (E1 and E2, referred to collectively as GBV-C envelope protein), an RNA helicase, a trypsin-like serine protease, and an RNA-dependent RNA polymerase. A major difference between GBV-C and HCV is in the amino terminus of the polyprotein. In many isolates, this region is truncated, and no core (or nucleocapsid) protein is present (Simons et al., 1995; Xiang et al., 1999). In vitro translation experiments suggest that the AUG immediately upstream of the putative E1 protein is preferentially used to initiate translation, although there may be as many as four AUG's in frame with the polyprotein upstream of this AUG (Simons et al., 1996).

The site of GBV-C replication has not been clearly identified, but it appears that replication in the hepatocyte, if it occurs, is not the primary source of virus in infected individuals (Laskus et al., 1998; Pessoa et al., 1998; Seipp et al., 1999). Recently, there were reports that human peripheral blood mononuclear cells (PBMC's) and interferon-resistant Daudi cells are permissive for GBV-C replication (Fogeda et al., 1999; Shimizu, 1999). In addition, transient replication of GBV-C was described in MT-2 cells (a human T-cell line), and PH5CH (a human hepatocyte line immortalized with simian virus 40 large T antigen) (Seipp et al., 1999).

C. Other Flavivirus NS5A's

Other Flaviviruses contain NS5A's that can be used in accordance with the present invention. These viruses include DEN1-4, YFV, TBEV, WNV, CSFV, BVDV, GBV-A, GBV-B, HGV, HCV2a, HCV3a, HCV2b, HCV1a, HCV1c and HCV1b.

IV. GBV-C Polypeptides

In certain aspects, the invention is directed to the the NS5A polypeptide of GBV-C virus, or a peptide or polypeptide derived there from SEQ ID NO:2 shows the NS5A translated product of SEQ ID NO:1 (cDNA). It is contemplated that the compositions and methods disclosed herein may be utilized to express all or part of SEQ ID NO:2 and derivatives thereof. In certain embodiments, compositions of the invention may include the nucleic acids encoding the peptides as set forth in SEQ ID NO:1 or 3. Determination of which protein or DNA molecules inhibit HIV may be achieved using functional assays measuring HIV replication and infectivity, which are familiar to those of skill in the art. The structure of the various polypeptides or peptides can be modeled or resolved by computer modeling, NMR, or x-ray crystallography. Such structures may be used to engineer derivatives of the various NS5A protein.

Exemplary accession nos. (incorporated by reference) for other NS5A's are as follows:

| Virus | Accession No. | Virus | Accession No. |
|---|---|---|---|
| West Nile | DQ318019 | Dengue 1-4 | AY66269 |
| Yellow fever | NC002031 | HCV 1a | AF011753 |
|  | AY603338 | 1b | AF333324 |
| BVDV | AF502399 | 1c | D14853 |
| Dengue 1-4 | M878512 | 2a | D00944 |
|  | M14931 | 2b | D10988 |
|  | M20558 | 3a | AF046866 |

A. Variants of GBV-C NS5A Polypeptides

Embodiments of the invention include various GBV-C NS5A polypeptides, peptides, and derivatives thereof. Amino acid sequence variants of a polypeptide can be substitutional, insertional or deletion variants. Deletion variants lack one or more residues of the native protein that are not essential for function or immunogenic activity. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties.

Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of GBV-C NS5A polypeptides, for example SEQ ID NO:2, provided the biological activity of the protein or peptide is maintained.

The term "functionally equivalent codon" is used herein to refer to codons that encode the same amino acid, such as the six codons for arginine or serine, and also refers to codons that encode biologically equivalent amino acids (see Table 1, below).

Certain embodiments of the invention include various peptides or polypeptides of the NS5A protein. For example, all or part of a GBV-C NS5A protein as set forth in SEQ ID NO:2 may be used in various embodiments of the invention. In certain embodiments, a fragment of the NS5A protein may comprise, but is not limited to about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 415, and any range derivable therein.

It also will be understood that amino acid and nucleic acid sequences may include additional residues, such as additional N— or C-terminal amino acids or 5' or 3' sequences, and yet still be essentially as set forth in one of the sequences disclosed herein, so long as the sequence meets the criteria set forth above, including the maintenance of biological activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of an NS5A polypeptide or peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA or RNA coding sequence, and nevertheless produce a protein with like properties. It is thus contemplated by the inventors that various changes may be made in the DNA or RNA sequences of genes or coding regions without appreciable loss of their biological utility or activity, as discussed herein. Table 1 shows the codons that encode particular amino acids.

TABLE 1

CODON TABLE

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

It is understood that an amino acid substituted for another having a similar hydrophilicity value still produces a biologically equivalent and immunologically equivalent protein.

In certain embodiments, an NS5A polypeptide may be a fusion protein. Fusion proteins may alter the characteristics of a given polypeptide, such antigenicity or purification characteristics. A fusion protein is a specialized type of insertional variant. This molecule generally has all or a substantial portion of the native molecule, linked at the N— or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals, or transmembrane regions.

B. In vitro Production of NS5A Polypeptides or Peptides

Various types of expression vectors are known in the art that can be used for the production of protein products. Following transfection with a expression vector, a cell in culture, e.g., a primary mammalian cell, a recombinant product may be prepared in various ways. A host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented (for exemplary methods see Freshney, 1992).

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large-scale production of cells and cell products. However, suspension cultured cells have limitations, such as tumorigenic potential and lower protein production than adherent cells.

In further aspects of the invention, other protein production methods known in the art may be used, including but not limited to prokaryotic, yeast, and other eukaryotic hosts such as insect cells and the like.

Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides.

C. Protein Purification

It may be desirable to purify NS5A polypeptides and peptides, or variants and derivatives thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, hydrophobic interaction chromatography, exclusion chromatography; polyacrylamide gel electrophoresis; isoelectric focusing. A particularly efficient method of purifying peptides is fast protein liquid chromatography (FPLC).

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme.

V. Flavivirus Polynucleotides

Certain embodiments of the invention include Flavivirus NS5A polynucleotides or nucleic acid molecules and fragments thereof. The polynucleotides of the invention may be isolated and purified from Flavivirus or cells infected or transfected with Flavivirus polynucleotides. The term isolated indicating they are free or substantially free from total viral or cellular genomic RNA or DNA, and proteins. It is contemplated that an isolated and purified Flavivirus nucleic acid molecule may take the form of RNA or DNA. A Flavivirus nucleic acid molecule refers to an RNA or DNA molecule that is capable of yielding all or part of a Flavivirus NS5A from a transfected cell.

When the present application refers to the function or activity of an infectious Flavivirus that is encoded by a Flavivirus polynucleotide, it is meant that the polynucleotide encodes a molecule that has the ability to propagate an infectious Flavivirus virus particle from a cell. It is contemplated that a Flavivirus polynucleotide may refer to a Flavivirus RNA transcript that is able to propagate an infectious Flavivirus virus particle after introduction to a cell or to a Flavivirus expression construct, clone, or vector composed of double-stranded DNA or DNA/RNA hybrid that is similarly capable, or a doublestranded DNA that is similiarly capable following in vitro transcription.

The term "cDNA" is intended to refer to DNA prepared using RNA as a template. The advantage of using a cDNA, as opposed to genomic RNA or an RNA transcript is stability and the ability to manipulate the sequence using recombinant DNA technology (See Maniatis, 1990; Ausubel, 1996). There may be times when the full or partial genomic sequence is preferred.

It also is contemplated that a given Flavivirus may be represented by natural variants or strains that have slightly different nucleic acid sequences but, nonetheless, encode the same viral polypeptides (see Table 1 above). Consequently, the present invention also encompasses derivatives of Flavivirus with minimal amino acid changes in its viral proteins, but that possesses the same activities.

The term "gene" is used for simplicity to refer to the nucleic acid giving rise to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding Flavivirus may contain a contiguous nucleic acid sequence encoding one or more Flavivirus genes and regulatory regions and be of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 10,000 or more nucleotides, nucleosides, or base pairs. Such sequences may be identical or complementary to all or part of SEQ ID NO:1.

In particular embodiments, the invention concerns isolated nucleic acid segments and recombinant vectors incorporating DNA sequences that encode Flavivirus NS5A polypeptides or peptides. Such vectors used in the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

In a non-limiting example, one or more nucleic acid constructs may be prepared that include a contiguous stretch of nucleotides identical to or complementary to a Flavivirus genome. A nucleic acid construct may be about 50, 60, 70, 80, 90, 100, 200, 300, 400, 500, 600, 700, 800, 900, 1,000, 2,000, 3,000, 4,000, 5,000, 6,000, 7,000, 8,000, 9,000, and 9,400, nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.

The nucleic acid segments used in the present invention encompass biologically functional and/or immunogenically equivalent Flavivirus NS5A proteins and peptides. Such sequences may arise as a consequence of codon redundancy and functional equivalency that are known to occur naturally within nucleic acid sequences and the proteins thus encoded. Alternatively, functionally and immunologically equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein.

A. Vectors Encoding Flavivirus

The present invention encompasses the use of vectors to encode for all or part of one or more Flavivirus NS5A polypeptides, including an infectious Flavivirus. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). In particular embodiments, gene therapy or immunization vectors are contemplated. One of skill in the art would be well equipped to construct a vector through standard recombinant techniques, which are described in Maniatis et al., 1990 and Ausubel et al., 1996, both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra. It is contemplated that an infectious Flavivirus particle of the present invention may arise from a vector containing Flavivirus sequence or RNA encoding Flavivirus sequence into a cell. Either of these, or any other nucleic acid molecules of the present invention may be constructed with any of the following nucleic acid control sequences. Thus, the full-length RNA transcript may contain the benefit of recombinant DNA technology such that it contains exogenous control sequences or genes.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" means that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or exogenous, i.e., from a different source than Flavivirus sequence. In some examples, a prokaryotic promoter is employed for use with in vitro transcription of a desired sequence. Prokaryotic promoters for use with many commercially available systems include T7, T3, and Sp6.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |

TABLE 2-continued

Promoter and/or Enhancer

| Promoter/Enhancer | References |
| --- | --- |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al, 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| $\beta$-Interferon | poly(rI) x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| $\alpha$-2-Macroglobulin | IL-6 | Kunz et al., 1989 |
| Vimentin | Serum | Rittling et al., 1989 |
| MHC Class I Gene H-2κb | Interferon | Blanar et al., 1989 |

TABLE 3-continued

Inducible Elements

| Element | Inducer | References |
| --- | --- | --- |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), human platelet endothelial cell adhesion molecule-I (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this 15 and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome-scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

5. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

7. Selectable and Screenable Markers

In certain embodiments of the invention, the cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either an eukaryotic or prokaryotic host cell, particularly one that is permissive for replication or expression of the vector.

C. Expression Systems

Numerous expression systems exist that comprise at least all or part of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK® BACULOVIRUS EXPRESSION SYSTEM from CLONTECH®.

Other examples of expression systems include STRATAGENE®'s COMPLETE CONTROL® Inducible Mammalian Expression System, which involves a synthetic ecdysone-inducible receptor, or its pET Expression System, an E. coli expression system. Another example of an inducible expression system is available from INVITROGEN®, which carries the T-REX® (tetracycline-regulated expression) System, an inducible mammalian expression system that uses the full-length CMV promoter. The Tet-On™ and Tet-Off™ systems from CLONTECH® can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

D. Introduction of Nucleic Acids into Cells

In certain embodiments, a nucleic acid may be introduce into a cell in vitro for production of polypeptides or in vivo for immunization purposes. There are a number of ways in which nucleic acid molecules such as expression vectors may be introduced into cells. In certain embodiments of the invention, the expression vector comprises a Flavivirus infectious particle or engineered vector derived from a Flavivirus genome. In other embodiments, an expression vector known to one of skill in the art may be used to express a segment of a Flavivirus nucleic, which may be translated into a Flavivirus polypeptide or peptide. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

"Viral expression vector" is meant to include those vectors containing sequences of that virus sufficient to (a) support packaging of the vector and (b) to express a polynucleotide that has been cloned therein. In this context, expression may require that the gene product be synthesized. A number of such viral vectors have already been thoroughly researched, including adenovirus, adeno-associated viruses, retroviruses, herpesviruses, and vaccinia viruses.

Delivery may be accomplished in vitro, as in laboratory procedures for transforming cells lines, or in vivo or ex vivo, as in the treatment of certain disease states. One mechanism for delivery is via viral infection where the expression vector is encapsidated in an infectious viral particle. Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), liposome (Ghosh and Bachhawat, 1991; Kaneda et al., 1989) and receptor-mediated transfection (Wu and Wu, 1987; Wu and Wu, 1988). Some of these techniques may be successfully adapted for in vivo or ex vivo use.

In certain embodiments, the nucleic acid encoding a gene or genes may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression vector is delivered to a cell and where in the cell the nucleic acid remains is dependent on the type of expression vector employed.

Transfer of a nucleic acid molecule may be performed by any of the methods mentioned above which physically or chemically permeabilize the cell membrane. This is particularly applicable for transfer in vitro, but it may be applied to in vivo use as well.

VI. Anti-HIV Therapies

In certain embodiments, therapeutic methods will include administering to a patient or subject a composition comprising an antigen or an antibody derived from a Flavivirus NS5A peptide or polypeptide, such as human or humanized animal derived antibodies. In various embodiments, the treatment methods of the invention may be used in combination with other anti-HIV treatments, such as Flavivirus infection as a therapeutic or preventative treatment for AIDS. For exemplary compositions and methods see PCT application WO 01/77157, which is incorporated herein by reference.

As a therapeutic measure, a Flavivirus NS5A agent can be used to reduce the severity or progression of AIDS, including the prevention of AIDS in HIV-infected individuals. A reduction in severity or progression of AIDS includes, but is not limited to, prevention of or a reduction in the severity, duration, or discomfort associated with the following conditions: prolonged and unexplained fatigue; swollen glands; prolonged fever; chills; excessive sweating; swollen gums and mouth lesions; sore throat; cough; shortness of breath; constipation; diarrhea; symptoms of well-known opportunistic infections; Kaposi sarcomas; skin rashes or lesions; loss of appetite or weight loss; malaise; headaches; speech impairment; muscle atrophy; memory loss; reduced cognitive functioning; swelling of the joints; joint stiffness or pain; cold intolerance; pain or tenderness in bones; energy level; anxiety, stress, and tension; groin lump; pruritus; genital sores; blurred or decreased vision; diplopia; light sensitivity; pain in chest, sides, back, muscle or stomach; and seizures.

As a preventative measure, a patient may be administered a pharmaceutically acceptable composition comprising a Flavivirus NS5A peptide or polypeptide. This agent may be used in conjunction with infection of CD4+ T cells with Flavivirus or a recombinant version of Flavivirus to inhibit infection of these cells by HIV. Alternatively, treatment with the Flavivirus NS5A compositions of the present invention may effect a combination of preventative and therapeutic treatments insofar as infection of other cells in an HIV-infected subject's body is prevented or attenuated.

Inhibition of AIDS progression may be demonstrated by reduction of detectable HIV in the HIV-infected subject; maintaining a CD4 count above 200 for a longer than average period of time; maintaining a normal T cell count; or maintaining normal p24 antigen. The term "therapeutic benefit" or "therapeutic effect" used throughout this application refers to anything that promotes or enhances the well-being of the subject with respect to the medical treatment of his/her condition, which includes treatment of HIV-infection (before the onset of AIDS), AIDS, as well as treatment of Hepatitis C. A list of nonexhaustive examples of this includes extension of the subject's life by any period of time; decrease or delay in the progression of AIDS (HIV, as described above) or Hepatitis C; decrease in viral load of HIV or HCV; decrease in HIV replication; clearance of HIV or HCV viremia reduced transmission of HCV or HIV; decrease in liver damage or complications; and a decrease in pain to the subject that can be attributed to the subject's condition.

VII. Combination Therapies

Of course it is understood that the method of the present invention, particularly administration of NS5A agents as treatment for an HIV-infected subject, may also be used in combination with the administration of traditional therapies. Alternatively, the compositions of the present invention may be given in combination with treatment or prevention of hepatitis C, such as a-interferon. Some such therapies are described below.

In many clinical situations, it is advisable to use a combination of distinct therapies. Thus, it is envisioned that, in addition to the therapies described herein, one would also wish to provide to the patient more "standard" pharmaceutical anti-retroviral therapies. Examples of standard therapies are provided below.

Combinations may be achieved by administering to a patient a single composition or pharmacological formulation that includes both agents, or by administering to a patient two distinct compositions or formulations, at the same time, wherein one composition may include a Flavivirus NS5A, or expression construct encoding such, and the other includes the standard anti-retroviral therapy. Alternatively, a Flavivirus-based therapeutic may precede or follow the other treatment by intervals ranging from minutes to weeks. In embodiments where the other agent and NS5A are adminstered separately to the patient, one would generally ensure that a significant period of time did not expire between the time of each delivery, such that the agent and NS5A would still be able to exert an advantageously combined effect on the patient. In such instances, it is contemplated that one would administer to the patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6, or 7) to several weeks (1, 2, 3, 4, 5, 6, 7, or 8) lapse between the respective administrations.

It also is conceivable that more than one administration of a NS5A-based therapeutic agent will be desired. Various combinations may be employed, where a NS5A is "A" and the other agent is "B," as exemplified below:

| A/B/A | B/A/B | B/B/A | A/A/B | B/A/A | A/B/B | B/B/B/A | B/B/A/B |
|-------|-------|-------|-------|-------|-------|---------|---------|
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated as well.

A. AZT

A well known, traditional therapy for the treatment of AIDS involves zovidovudine (AZT™ available from Burroughs Wellcome). This is one of a class of nucleoside analogues known as dideoxynucleosides which block HIV replication by inhibiting HIV reverse transcriptase. The anti-AIDS drug zidovudine (also known as AZT) may also be used in limited circumstances, mostly in combination with rifampin, as described by Burger et al. (1993).

The compositions and methods disclosed herein will be particularly effective in conjunction with other forms of therapy, such as AZT and/or protease inhibitors that are designed to inhibit viral replication, by maintaining desirable levels of white blood cells. This, in effect, buys the patient the time necessary for the anti-viral therapies to work.

B. HAART

New combination drug therapy has shown promising results in the treatment of HIV-infected patients. Treatment with potent anti-HIV drug combinations is referred to as "highly active anti-retroviral therapy" (HAART), and it has provided clinical improvement, longer survival, and improved quality of life for people infected with HIV during all four stages of HIV disease. Examples of HAART include a protease inhibitor (indinavir, nelfinavir, ritonavir, ritonavir/saquinavir, or saquinavir) combined with two nucleoside analogs (AZT/ddI, d4T/ddI, AZT/ddC, AZT/3TC, or d4T/3TC).

In many instances, it will be desirable to have multiple administrations of the inventive compositions and/or a vaccines, usually not exceeding six administrations or vaccinations, more usually not exceeding four vaccinations. In certain embodiments, one or more, usually at least about three administrations or vaccinations may be provided. The administrations or vaccinations will normally be at from two to twelve week intervals, more usually from three to five week intervals. Periodic boosters at intervals of 1-5 years, usually three years, will be desirable to maintain protective levels of the antibodies. The course of the immunization or treatment may be followed by standard antibody assays. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

The manner of application may be varied widely. Any of the conventional methods for administration of an antibody or vaccine are applicable. These are believed to include oral application on a solid physiologically acceptable base or in a physiologically acceptable dispersion, parenterally, by injection or the like. The dosage of the NS5A agent will depend on the route of administration and will vary according to the size of the host.

The NS5A agents and flavivirus nucleic acids of the invention may be formulated into a pharmaceutically acceptable composition, see below, or vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparation of flavivirus NS5A agents as active ingredients is generally well understood in the art by analogy, as exemplified by U.S. Pat. Nos. 6,479,243, 6,399,763, 5,714,153, 5,582,981, and 4,833,077, all incorporated herein by reference. The preparation of vaccines that contain flavivirus sequences as active ingredients is generally well understood in the art by analogy, as exemplified by U.S. Pat. Nos. 5,958,895, 6,004,799, and 5,620,896, all incorporated herein by reference.

VIII. Pharmaceutical Compositions and Routes of Administration

Pharmaceutical compositions including NS5A peptides and polypeptides will be formulated along the line of typical pharmaceutical drug and biological preparations. A discussion of formulations may be found in Remington's Pharmaceutical Sciences (1990). The percentage of active compound in any pharmaceutical preparation is dependent upon both the activity of the compound, in this case ability of NS5A agents to inhibit HIV replication. Typically, such compositions should contain at least 0.1% active compound. The percentage of the compositions and preparations may, of course, be varied and may conveniently be between about 2 to about 60% of the weight of the unit. The amount of active compounds in such therapeutically useful compositions is such that a suitable dosage will be obtained.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injection is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, phenylmecuric nitrate, m-cresol, and the like. In many cases, it will be preferable to use isotonic solutions, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active compounds in the required amount in the appropriate solvent with various of the other ingredients enumerated above, as required, followed by sterile filtration. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques that yield a powder of the active ingredient plus any additional desired ingredient from a previously sterile-filtered solution thereof.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

The active compounds of the present invention can be formulated for parenteral administration, e.g., formulated for injection via the intravenous, intramuscular, intrathoracic, sub-cutaneous, or even intraperitoneal routes. Administration by i.v. or i.m. are specifically contemplated. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In certain embodiments, it may be desirable to provide a continuous supply of therapeutic compositions to the patient. For intravenous or intraarterial routes, this is accomplished by drip system. For various approaches, delayed release formulations could be used that provided limited but constant amounts of the therapeutic agent over and extended period of time. For internal application, continuous perfusion may be preferred. This could be accomplished by catheterization followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Peptides or polypeptides may be administered in a dose that can vary from 0.01, 0.05, 0.1, 0.5, 1, 5, 10, 20, 30, 40, 50, 60, 70, 80, 90, 100 mg/kg of weight to 50, 60, 70, 80, 90, 100, 110, 120, 130, 140, 150, 160, 170, 180, 190, 200 mg/kg of weight in one or more daily, weekly, monthly, or yearly administrations during one or various days, weeks, months, or years. The antibodies can be administered by parenteral injection (intravenous, intraperitoneal, intramuscular, subcutaneous, intracavity or transdermic). For viral vectors, one generally will prepare a viral vector stock. Depending on the kind of virus and the titer attainable, one will deliver 1 to 100, 10 to 50, 100-1000, or up to $1\times10^4$, $1\times10^5$, $1\times10^6$, $1\times10^7$, $1\times10^8$, $1\times10^9$, $1\times10^{10}$, $1\times10^{11}$, or $1\times10^{12}$ infectious particles to the patient. Similar figures may be extrapolated for liposomal or other non-viral formulations by comparing relative uptake efficiencies. Formulation as a pharmaceutically acceptable composition is discussed below.

In many instances, it will be desirable to have multiple administrations of the NS5A agent. The compositions of the invention may be administered 1, 2, 3, 4, 5, 6, 7, 8, 9, 10, or more times. The administrations will normally be at from one to twelve week intervals, more usually from one to four week intervals. Periodic re-administration will be desirable with recurrent exposure to the pathogen (e.g., HIV). For example, an HIV positive mother would be re-inoculated prior to parturition from a second pregnancy.

Precise amounts and delivery regimen for the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

In a particular embodiment of the invention, the NS5A agent may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Current in vivo lipid delivery methods use subcutaneous, intradermal, intratumoral, or intracranial injection to avoid the toxicity and stability problems associated with cationic lipids in the circulation. The DOTAP:cholesterol lipid formulation is said to form a unique structure termed a "sandwich liposome." This formulation is reported to "sandwich" DNA between an invaginated bi-layer or 'vase' structure. Beneficial characteristics of these lipid structures include a positive ρ, colloidal stabilization by cholesterol, two dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990).

VIII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cells: Tet-Off Jurkat cells (Clontech) were transfected with pTRE 2 Hyg plasmids containing full-length GBV-C NS5A (from the full-length GBV-C infectious clone AF121950) or with the vector only (control) by electroporation. Transfectants were selected using hygromycin, and cell lines cloned twice. Cells were grown in RPMI 1640 with or without doxycycline as recommended.

NS5A expression: Cells were lysed in RIPA buffer containing protease and phosphatase inhibitors and examined by immunoblot using rabbit anti-NS5A antisera.

HIV infections: Clinical and laboratory CXCR4 tropic strains of HIV-1 were used to infect Jurkat cell lines expressing NS5A or the vector control. Cells were maintained in doxycycline at various concentrations to inhibit NS5A expression. HIV replication was measured using culture supernatant p24 antigen ELISA.

Results: Jurkat cell lines stably expressing GBV-C NS5A protein were established, and expression of NS5A was regulated by doxycycline. HIV infection of cells expressing NS5A was decreased, as measured by p24 antigen compared to control cells or NS5A-containing cells grown in the pesence of doxycycline. NS5A-expressing cells also had lower surface density of CXCR4 and released increased levels of the CXCR4 ligand SDF-1 into culture supernatants, which may account for observations. In addition, NS5A led to increased levels of two genes associated with resistance to apoptosis, and rendered cells resistant to Fas-mediated apoptosis. This latter observation may account for slower decline in CD4 cell counts observed in HIV-infected people.

Summary: Jurkat cell lines stably expressing GBV-C NS5A protein (regulated by doxycycline) were established (FIG. 1). HIV infection of Jurkat cells that expressed GBV-C NS5A resulted in decreased levels of HIV replication (measured by p24 antigen) compared to vector control cells or cells in which NS5A expression was reduced by growth in doxycycline (FIGS. 2A-C). NS5A expressing cells had lower levels of CXCR4 on the surface than vector control cells, and also had reduced release of SDF-1 into culture supernatants, suggesting that NS5A expression may interact with chemokine receptor pathways (FIGS. 3A-B). Although part of the HIV inhibitory effect of GBV-C is mediated by E2 protein interactions with cellular receptor(s), the NS5A protein appears to also contribute to an anti-HIV effect of GBV-C (FIGS. 4A-B). GBV-C NS5A, like HCV, appears to have two phosphorylation states. HCV NS5A hyperphosphorylation has been reported by some to require NS4 expression. These data show that NS4 is not required for hyperphosphorylation of GBV-C NS5A (FIG. 5). NS5A led to relative resistance to Fas-mediated apoptosis, which could slow CD4 cell decline. HCV NS5A has previously been shown to be anti-apoptotic (FIG. 6). GBV-C infected PBMCs did not show decreased CXCR4 expression, although CCR5 expression was reduced. Because active GBV-C replication is required to produce NS5A, and active replication occurs in a small percentage of PBMCs, downregulation of CXCR4 would be missed. In contrast, E2 (structural protein) is released into supernatant and will have more widespread effects leading to decreased CCR5 (FIG. 7).

Example 2

NS5A Inhibition of HIV Replication is Dose Dependent, Independent of PKR and May Involve SDF-1

Using Jurkat cells that are infected with HIV, doxycycline-repessable expression constructs encoding GBV-C NS5A were used to inhibit HIV replication. As shown in FIG. 8, the use of 0, 0.01, 0.1 and 1 μg of doxycycline produced decreasing amounts of HIV inhibition as measured by p24 antigen levels. No such effect was seen in control Jurkat cells.

The inventors previously showed that NS5A's from interferon resistant (IFN-R) GBV-C inhibited PKR-mediated phosphorylation of eIF2α, which is part of the inteferon cascade, whereas interferon sensitive (IFN-S) did not. The NS5A's from IFN-R and IFN-S strains were compared for their respective abilities to inhibit HIV replication. As shown in FIG. 9, both strains were equally effective at inhibiting HIV replication as measured by p24 antigen concentration. Thus, the effect is apparently not related to PKR-function.

Following treatment with of HIV-infected Jurkat cells with NS5A, SDF-1 is released into culture supernatants (data not shown). In an effort to determine whether there is any link between SDF-1 and HIV inhibition, anti-SDF-1 antibodies were added to the Jurkat cell cultures. As shown in FIG. 10, there was an increase in HIV replication ranging from 50% to almost 60% as compared to unreated controls, thereby suggesting that SDF-1 might play a role.

Example 3

NS5A Inhibits Distinct Strains of HIV

Three different strains of HIV—ELI (X4) Clade D, JF (X4) Clade B and MN (X4) Clade B—were tested for replication in the presence of NS5A. As shown in FIGS. 11A-C, all were sensitive to NS5A-mediated inhibition.

Example 4

GBV-C NS5A Fragments Inhibit HIV Replication

A variety of NS5A fragments were tested for their ability to inhibit HIV replication.

Figure 12:
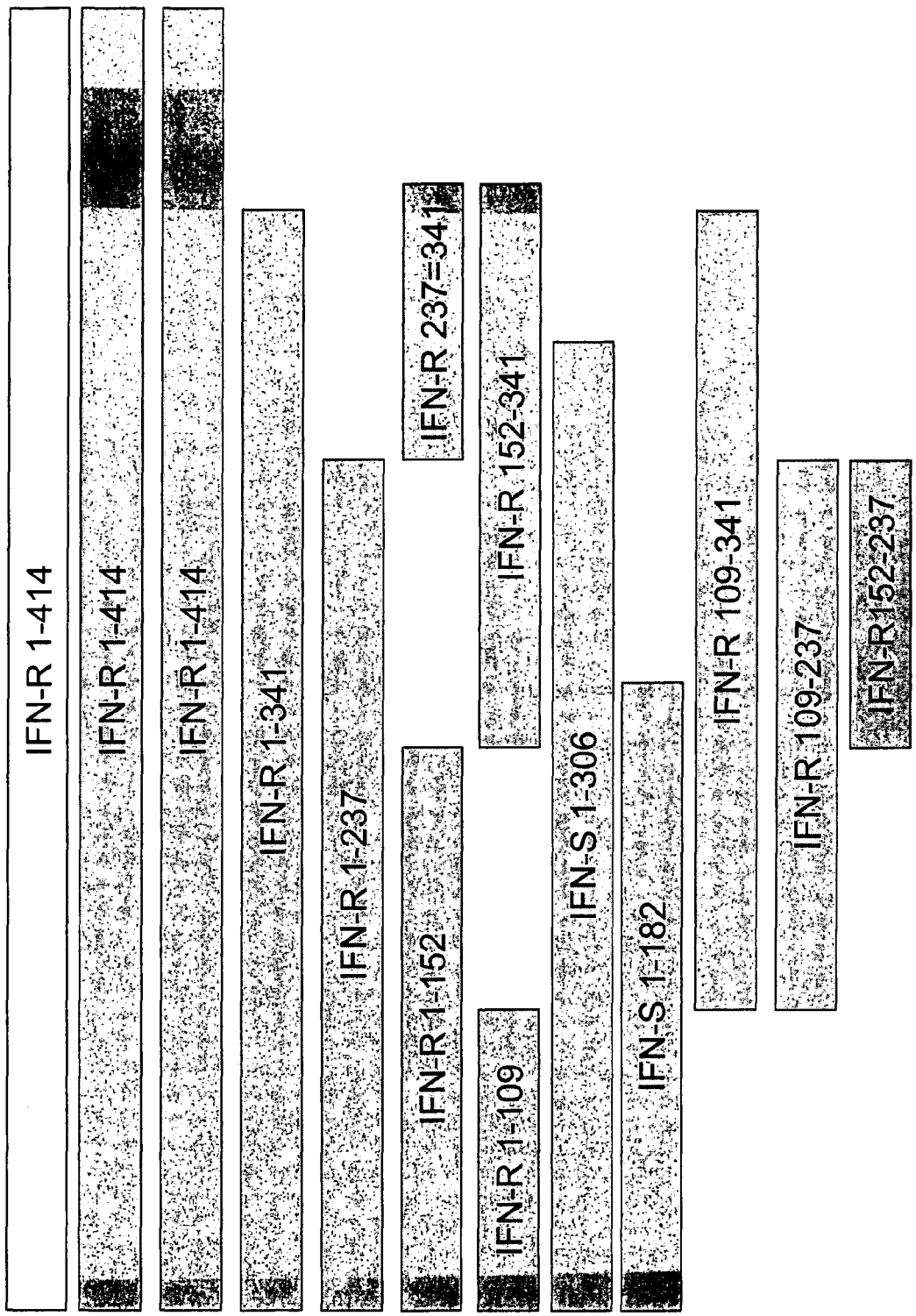
FIG. 12—Fragments of NS5A That Have Been Stably Expressed in Jurkat Cells. Shaded bars indicate fusions or fragments.

Methods. Stable Jurkat cell lines expressing PKR-inhibiting and non-inhibiting NS5A proteins were generated, as were a series of C-terminal deletion mutants (FIG. 12). These cell lines expressed NS5A proteins of 123, 161, 181, 250, 314, and 363 amino acids (aa). All constructs had stop codons after NS5A, followed by the EMC IRES and GFP. A control cell line expressing only GFP served as a negative control, and NS5A and GFP expression were regulated by tetracycline. HIV replication was measured by p24 antigen release into culture supernatant or by measuring infectivity.

Results. Jurkat cell lines demonstrated regulated expression of NS5A and deletion mutants as shown by western blot and GPF expression. The NS5A and GFP genes were shown to remain linked by RT-PCR of cellular DNA from recombinant cell lines. Expression of either PKR-inhibiting or non-inhibiting NS5A proteins resulted in HIV inhibition (>95% reduction in p24 antigen), thus the HIV- and PKR-inhibiting functions are independent. All deletion mutants of 250 aa or larger retained HIV-inhibiting effects, whereas those with 181 aa or smaller did not (FIG. 13).

Example 5

HCV and GBV-B Virus NS5A Proteins Inhibit HIV Replication in Jurkat Cells

Hepatitis C virus (HCV), like GBV-C, commonly infect humans. GBV-B is a primate virus that is closely related to both HCV and GBV-C. HCV and GBV-C NS5A proteins both inhibit PKR function. To further. characterize the inventors work showing inhibition of X4-tropic HIV replication, they expressed HCV and GBV-B NS5A's and a series of GBV-C NS5A deletions in Jurkat cells, and measured the effect of these proteins on HIV replication.

Methods. Jurkat cell lines stably expressing HCV, GBV-B, and GBV-C NS5A proteins were generated, as were a series of GBV-C NS5A deletion mutants. All constructs had stop codons after NS5A, followed by the EMC IRES and GFP. A control cell line expressing only GFP served as a negative control, and NS5A and GFP expression were regulated by tetracycline. Plasmids were transfected using the Amaxa nucleofection method, cells were selected for growth in hygromycin and for GFP expression. HIV replication was measured by p24 antigen release into culture supernatant or by measuring infectivity.

Figure 14:
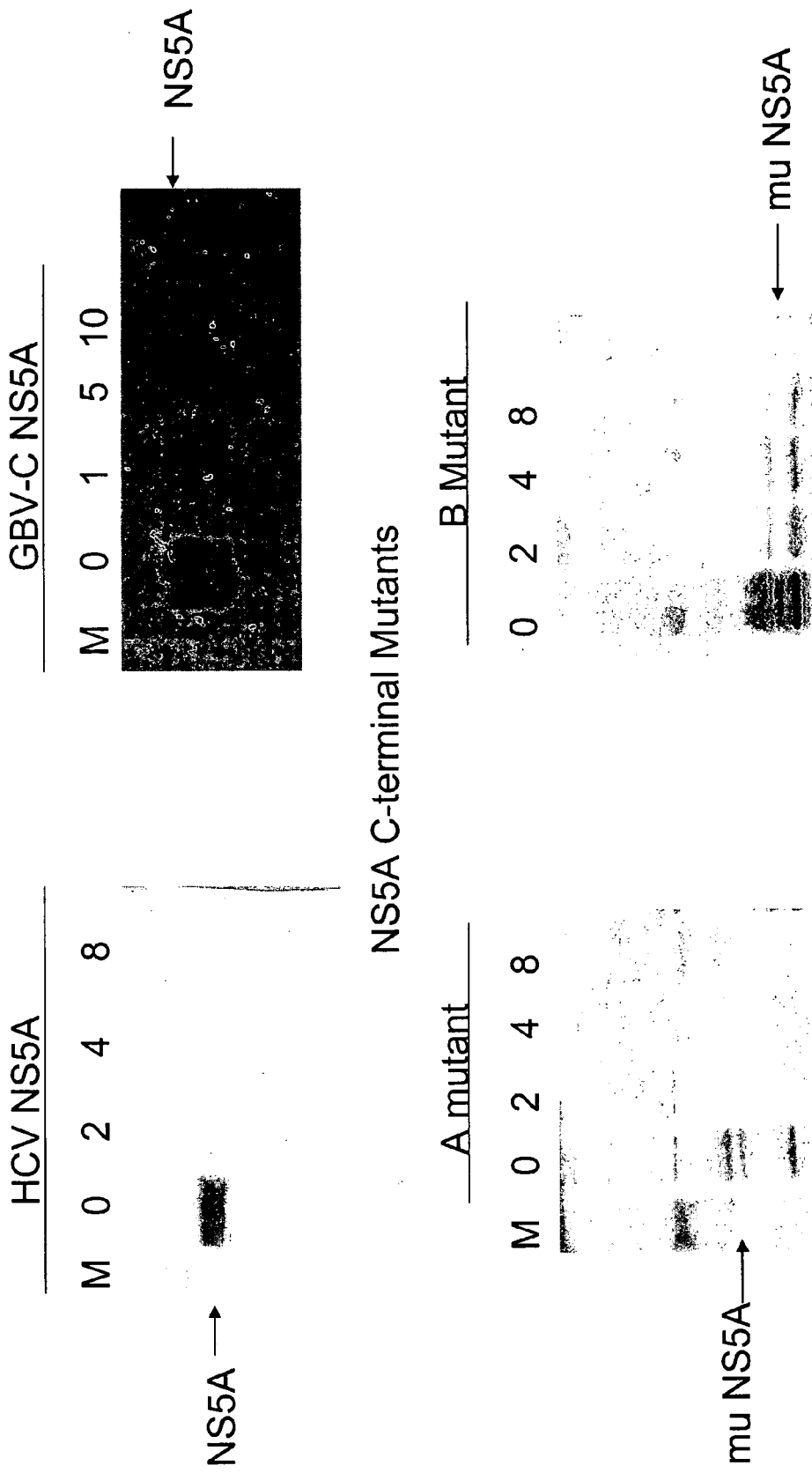
FIG. 14—Doxycycline-Repressed Expression of NS5A. Lanes are labeled with amounts of doxycycline (μg/ml); arrows indicate NS5A or mutants (mu NS5A).
Figure 15:
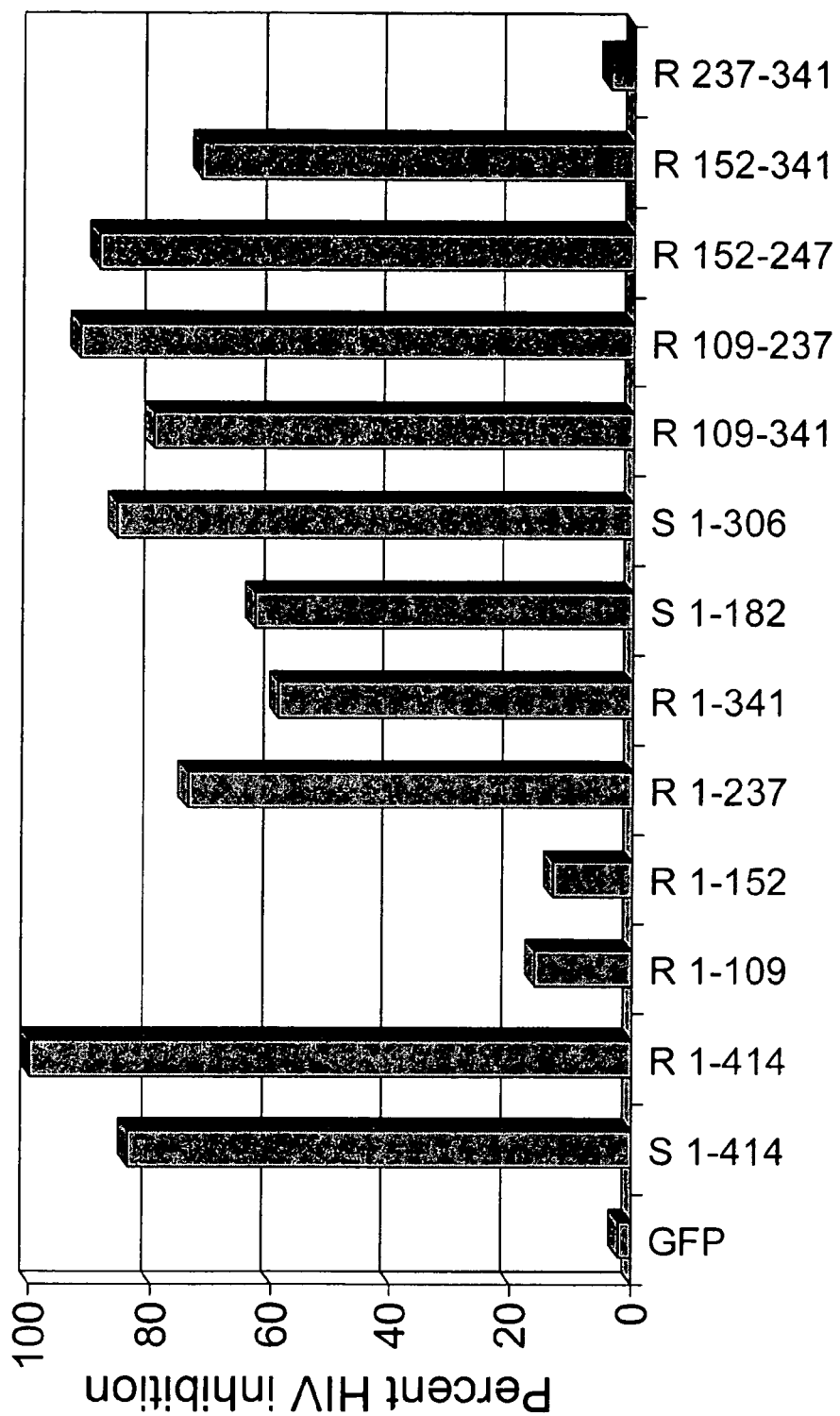
FIG. 15—Percent Inhibition of HIV Replication by NS5A Fragments. Various fragments identified by residues of NS5A remaining, and their ability to inhibit HIV replication (by p24 antigen levels) on day 6 after infection.
Figure 16:
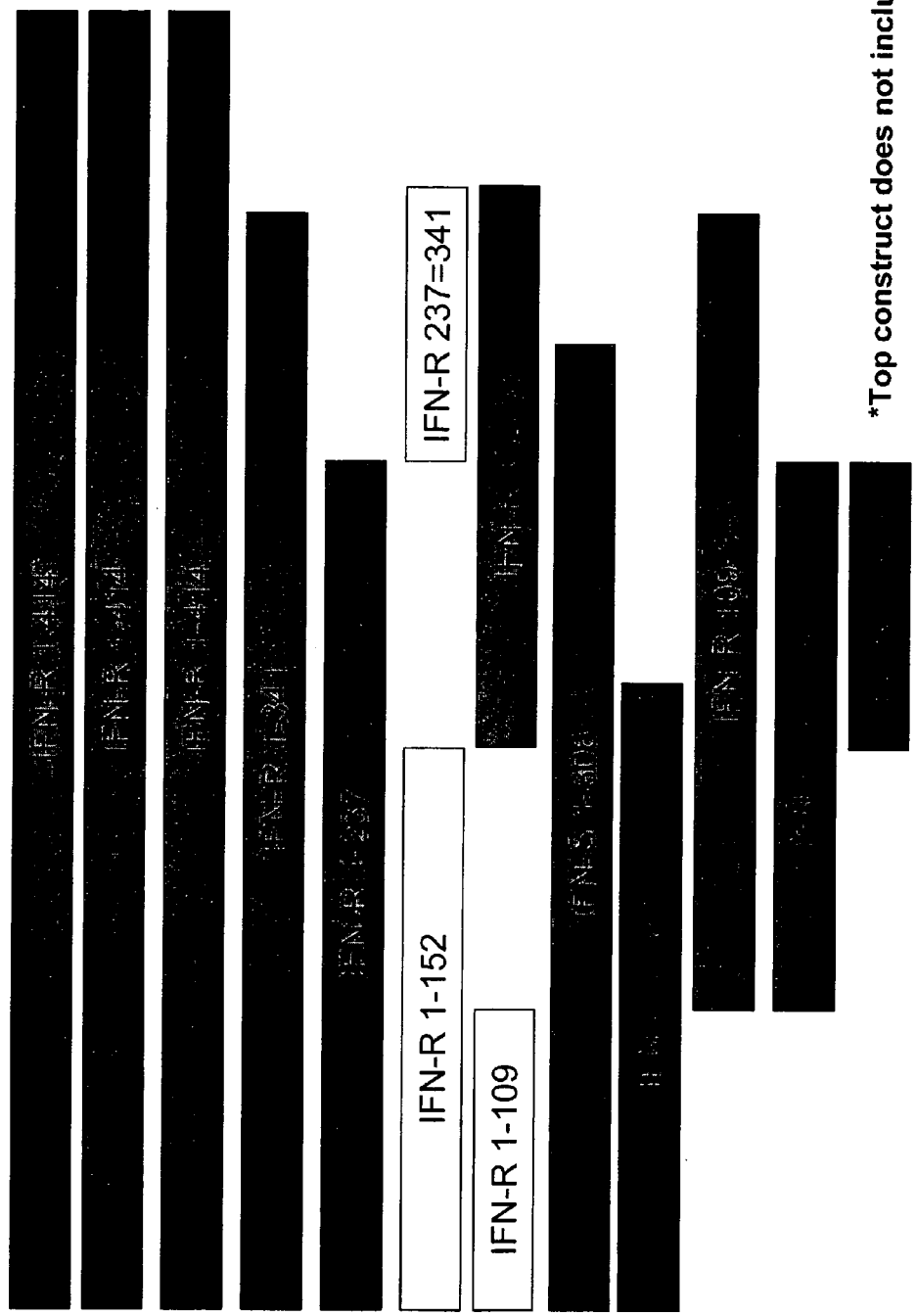
FIG. 16—Fragments of NS5A That Inhibit HIV Replication. Shaded bars inhibit HIV; open bars do not inhibit HIV; lined bars not yet tested.

Results. Jurkat cell lines demonstrated regulated expression of HCV, GBV-B GBV-C NS5A proteins and GBV-C deletion mutants as determined by GFP expression and when antibodies were available, by immunoblot (FIG. 14). For constructs in which antibodies were not available, the NS5A and GFP coding sequences were linked (detected by PCR of cellular DNA). Expression of HCV, GBV-B and GBV-C NS5A proteins resulted in HIV inhibition (>95% reduction in p24 antigen), thus the inhibitory effect appears conserved between these three flaviviruses (FIG. 15). All deletion mutants containing GBV-C NS5A amino acids (aa) between number 152 and 237 retained HIV-inhibiting effects, whereas those with C-terminal deletions containing ≦152 NS5A aa's did not inhibit HIV replication (FIG. 16). The effect was reduced in NS5A containing cells grown in doxycycline (NS5A expression turned off), but not in control cells grown in doxycycline. Thus, expression of GBV-C, GBV-B, and HCV NS5A proteins resulted in inhibition of CXCR4-tropic HIV replication in Jurkat cells, and the inhibitory effect requires GBV-C aa's 152-237, coinciding with domain II of the HCV NS5A protein. The region may possibly narrowed to 152-182 (FIG. 17).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,554,101
U.S. Pat. No. 4,683,202
U.S. Pat. No. 4,833,077
U.S. Pat. No. 4,879,236
U.S. Pat. No. 5,582,981
U.S. Pat. No. 5,620,896
U.S. Pat. No. 5,650,298
U.S. Pat. No. 5,714,153
U.S. Pat. No. 5,871,986
U.S. Pat. No. 5,874,563
U.S. Pat. No. 5,925,565
U.S. Pat. No. 5,928,906
U.S. Pat. No. 5,935,819
U.S. Pat. No. 5,958,895
U.S. Pat. No. 6,004,799
U.S. Pat. No. 6,399,763
U.S. Pat. No. 6,479,243
PCT Appln. WO 01/77157
PCT Appln. PCT/US03/33925
PCT Appln. PCT/US2004/017706
Akiyoshi et al., *Am. J. Gastroenterol.*, 94:1627-1631, 1999.
Almendro, et al.,*J Immunol.*, 157(12):5411-21, 1996.
Alter et al., *N. Engl. J Med.*, 336:741-746, 1997a.
Alter et al., *N. Engl. J. Med.*, 336:747-754, 1997b.
Angel et al., *Mol. Cell. Biol.*, 7:2256, 1987a.
Angel et al., *Cell*, 49:729, 1987b.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Baichwal and Sugden, In: *Gene Transfer*, Kucherlapati (Ed.), NY, Plenum Press, 117-148, 1986.
Banerji et al., *Cell*, 27(2 Pt 1):299-308, 1981.
Banerji et al., *Cell*, 33(3):729-740, 1983.

Barany and Merrifield, In: *The Peptides*, Gross and Meienhofer (Eds.), Academic Press, NY, 1-284, 1979.
Berkhout et al., *Cell*, 59:273-282, 1989.
Blanar et al., *EMBO J*, 8:1139, 1989.
Bodine and Ley, *EMBO J.*, 6:2997, 1987.
Boshart et al., *Cell*, 41:521, 1985.
Bosze et al., *EMBO J*, 5(7):1615-1623, 1986.
Braddock et al., *Cell*, 58:269, 1989.
Bukh et al., *J. Inf. Dis.*, 177:855-862, 1998.
Bulla and Siddiqui, *J. Virol.*, 62:1437, 1986.
Burger et al., *Antimicrob Agents Chemother.*, 37(7):1426-31, 1993.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonell et al., *FEMS Microbiol. Lett.*, 177(1):75-82, 1999.
Celander and Haseltine, *J. Virology*, 61:269, 1987.
Celander et al., *J. Virology*, 62:1314, 1988.
Chandler et al., *Cell*, 33:489, 1983.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7:2745-2752, 1987.
Choi et al., *Cell*, 53:519, 1988.
Cocea, *Biotechniques*, 23(5):814-6, 1997.
Cohen et al., *J. Cell. Physiol.*, 5:75, 1987.
Costa et al., *Mol. Cell. Biol.*, 8:81, 1988.
Cripe et al., *EMBO J*, 6:3745, 1987.
Culotta and Hamer, *Mol. Cell. Biol.*, 9:1376, 1989.
Dandolo et al., *J. Virology*, 47:55-64, 1983.
Dawson et al., *J. Med. Virol.* 50:97-103, 1996.
de Martino et al., *J. Infect. Dis.*, 178:862-865, 1998.
De Villiers et al., *Nature*, 312(5991):242-246, 1984.
Deacon et al., *Science* 270:988-991, 1995.
Deschamps et al., *Science*, 230:1174-1177, 1985.
Edbrooke et al., *Mol. Cell. Biol.*, 9:1908, 1989.
Edlund et al., *Science*, 230:912-916, 1985.
Fechheimer et al., *Proc. Nat'l Acad. Sci. USA*, 84:8463-8467, 1987.
Feng and Holland, *Nature*, 334:6178, 1988.
Feucht et al., *Hepatology*, 26:491-494, 1997.
Firak and Subramanian, *Mol. Cell. Biol.*, 6:3667, 1986.
Foecking and Hofstetter, *Gene*, 45(1):101-105, 1986.
Fogeda et al., *J. Virol.* 73:4052-4061, 1999.
Fraley et al., *Proc. Natl. Acad. Sci. USA*, 76:3348-3352, 1979.
Freshney, In: *Animal Cell Culture: a Practical Approach*, 2$^{nd}$ Ed., Oxford/NY, IRL Press, Oxford University Press, 1992.
Fujita et al., *Cell*, 49:357, 1987.
Gabizon et al., *Cancer Res.*, 50(19):6371-6378, 1990.
Ghosh and Bachhawat, In: *Liver diseases, targeted diagnosis and therapy using specific receptors and ligands*, Wu and Wu (Eds.), NY, Marcel Dekker, 87-104, 1991.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Gossen et al., *Proc. Natl. Acad. Sci. USA*, 89:5547-5551, 1992.
Gossen et al., *Science*, 268:1766-69, 1995.
Graham and Van Der Eb, *Virology*, 52:456-467, 1973.
Greene et al., *Immunology Today*, 10:272, 1989
Grosschedl and Baltimore, *Cell*, 41:885, 1985.
Harland and Weintraub, *J. Cell Biol.*,10 1: 1094-1099, 1985.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Herr and Clarke, *Cell*, 45:461, 1986.
Hirochika et al., *J Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Huang et al., *Cell*, 27:245, 1981.
Huang et al., *Nature Med.*, 2:1240-1243, 1996.
Hug et al., Mol. *Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Katinka et al., *Cell*, 20:393, 1980.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Koch et al., *Mol. Cell. Biol.*, 9:303, 1989.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kyte and Doolittle, *J. Mol. Biol.*, 157:105-132, 1982.
Lareyre, et al., *J. Bio. Chem.*, 274(12):8282-90, 1999.
Larsen et al., *Proc Natl. Acad. Sci. USA.*, 83:8283, 1986.
Laskus et al., *J. Virol.*, 72:3072-3075. 1998.
Laspia et al., *Cell*, 59:283, 1989.
Latimer et al., *Mol. Cell. Biol.*, 10:760, 1990.
Leary et al., *J. Med. Virol.*, 48:60-67. 1996.
Lee et al., *DNA Cell Biol.*, 16(11):1267-1275, 1997.
Lee et al., *Nature*, 294:228, 1981.
Lee et al., *Nucleic Acids Res.*, 12:4191-206, 1984.
Lefrere et al., *J. Infect. Dis.*, 179:783-789, 1999.
Levenson et al., *Hum. Gene Ther.*, 9(8):1233-6, 1998.
Levinson et al., *Nature*, 295:79, 1982.
Lin et al., *Mol. Cell. Biol.*, 10:850, 1990.
Linnen et al., *Science*, 271:505-508. 1996.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Maniatis, et al., In: *Molecular Cloning*, A Laboratory Manual, Cold Spring Harbor Press, Cold Spring Harbor, N.Y., 1990.
Marks et al., *Bio/Technol.*, 10:779-783, 1992.
McNeall et al., *Gene*, 76:81, 1989.
Merrifield, *Science*, 232: 341-347, 1986
Miksicek et al., *Cell*, 46:203, 1986.

Mordacq and Linzer, *Genes and Dev.,* 3:760, 1989.
Moreau et al., *Nucl. Acids Res.,* 9:6047, 1981.
Muesing et al., *Cell,* 48:691, 1987.
Nerurkar et al., *J. Med. Virol.,* 56:123-127, 1998.
Ng et al., *Nuc. Acids Res.,* 17:601, 1989.
Nicolas and Rubenstein, In: *Vectors: A survey of molecular cloning vectors and their uses,* Rodriguez and Denhardt (eds.), Stoneham: Butterworth, 493-513, 1988.
Nicolau and Sene, *Biochim. Biophys. Acta,* 721:185-190, 1982.
Nomoto et al., *Gene,* 236(2):259-271, 1999.
Ondek et al., *EMBO J.,* 6:1017, 1987.
Ornitz et al., *Mol. Cell. Biol.,* 7:3466, 1987.
Palmiter et al., *Nature,* 300:611, 1982.
Pech et al., *Mol. Cell. Biol.,* 9:396, 1989.
Pelletier and Sonenberg, *Nature,* 334(6180):320-325, 1988.
Perez-Stable and Constantini, *Mol. Cell. Biol.,* 10:1 116, 1990.
Pessoa et al., *Hepatol.,* 27:877-880, 1998.
Picard and Schaffner, *Nature,* 307:83, 1984.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Potter et al., *Proc. Natl. Acad. Sci. USA,* 81:7161-7165, 1984.
Queen and Baltimore, *Cell,* 35:741, 1983.
Quinn et al., *Mol. Cell. Biol.,* 9:4713, 1989.
Redondo et al., *Science,* 247:1225, 1990.
Reisman and Rotter, *Mol. Cell. Biol.,* 9:3571, 1989.
Remington's Pharmaceutical Sciences, 18th Ed. Mack Printing Company, 1389-1404, 1990,
Resendez Jr. et al., *Mol. Cell. Biol.,* 8:4579, 1988.
Ridgeway, In: *Vectors: A survey of molecular cloning vectors and their uses,* Rodriguez and Denhardt (Eds.), Stoneham: Butterworth, 467-492, 1988.
Ripe et al., *Mol. Cell. Biol.,* 9:2224, 1989.
Rippe et al., *Mol. Cell Biol.,* 10:689-695, 1990.
Rittling et al., *Nuc. Acids Res.,* 17:1619, 1989.
Robertson et al., *Arch. Virol.,* 143:2493-2503, 1998.
Rosen et al., *Cell,* 41:813, 1988.
Rowland-Jones, *J. Infect.,* 38:67-70, 1999.
Sabin et al., *J. Acquir. Immune Defic. Syndr.,* 19:546-547, 1998.
Sakai et al., *Genes and Dev.,* 2:1144, 1988.
Sambrook et al., In: *Molecular cloning,* Cold Spring Harbor Laboratory Press, Cold Spring Harbor, N.Y., 2001.
Satake et al., *J. Virology,* 62:970, 1988.
Schaffner et al., *J. Mol. Biol.,* 201:81, 1988.
Searle et al., *Mol. Cell. Biol.,* 5:1480, 1985.
Seipp et al., *J. Hepatol.,* 30:570-579, 1999.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Shimizu, *J. Virol.,* 73:8411-8414, 1999.
Simons et al., *J. Virol.,* 70:6126-6135. 1996.
Simons et al., *Nature Med.,* 1:564-569, 1995a.
Simons et al., *Proc. Natl. Acad. Sci. USA,* 92:3401-3405, 1995b.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Stephens and Hentschel, *Biochem. J.,* 248:1, 1987.
Stewart and Young, In: *Solid Phase Peptide Synthesis,* 2d. ed., Pierce Chemical Co., 1984.
Stuart et al., *Nature,* 317:828, 1985.
Sullivan and Peterlin, *Mol. Cell. Biol.,* 7:3315, 1987.
Swartzendruber and Lehman, *J. Cell. Physiology,* 85:179, 1975.
Tacke et al., *Hepatol.,* 26:1626-1633, 1997.
Takebe et al., *Mol. Cell. Biol.,* 8:466,1988.
Tam et al., *J. Am. Chem. Soc.,* 105:6442, 1983.
Tanaka et al., *J. Hepatol.,* 27:1110-1112, 1997.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Temin, In: *Gene Transfer,* Kucherlapati (ed.), NY: Plenum Press, 149-188, 1986.
Thiesen et al., *J. Virology,* 62:614, 1988.
Thomas et al., *J. Infect. Dis.,* 177:539-542, 1998.
Toyoda et al., *J. Acquir. Immune Defic. Syndr.,* 17:209-213, 1998.
Treisman, *Cell,* 42:889, 1985.
Tronche et al., *Mol. Biol. Med.,* 7:173, 1990.
Trudel and Constantini, *Genes and Dev.,* 6:954, 1987.
Tsumaki et al., J. *Biol. Chem.,* 273(36):22861-22864, 1998.
Tur-Kaspa et al., *Mol. Cell Biol.,* 6:716-718, 1986.
Tyndell et al., *Nuc. Acids. Res.,* 9:6231, 1981.
Vannice and Levinson, *J. Virology,* 62:1305, 1988.
Vasseur et al., *Proc Natl. Acad. Sci. USA,* 77:1068, 1980.
Wang and Calame, *Cell,* 47:241, 1986.
Weber et al., *Cell,* 36:983, 1984.
Weinberger et al. *Mol. Cell. Biol.,* 8:988, 1984.
Winoto and Baltimore, *Cell,* 59:649, 1989.
Winoto and Baltimore, *Cell,* 59:649, 1989.
Wu and Wu, *Biochem.,* 27:887-892, 1988.
Wu and Wu, *J. Biol. Chem.,* 262:4429-4432, 1987.
Wu et al., *Biochem. Biophys. Res. Commun.,* 233(1):221-6, 1997.
Wu et al., *J. Med. Virol.,* 52:83-85. 1997.
Xiang et al., *J. Viral Hepat.,* 6:S16-S22, 1999.
Yang et al., *Proc. Natl. Acad. Sci USA,* 87:9568-9572, 1990.
Yutzey et al. *Mol. Cell. Biol.,* 9:1397, 1989.
Zhao-Emonet, et al., *Biochim. Biophys. Acta,* 1442(2-3):109-19, 1998.

What is claimed is:

1. A method for treating HIV infection comprising administering to a subject a composition comprising HCV or GBV-C NS5A peptide or polypeptide, wherein said NS5A peptide or polypeptide inhibits HIV replication and thereby treats HIV infection, and further wherein the NS5A peptide or polypeptide further comprises a targeting signal.

2. The method of claim 1, wherein the targeting signal is a nuclear targeting signal.

3. The method of claim 1, wherein the targeting signal targets a cell surface receptor.

4. The method of claim 3, wherein the cell surface receptor is the CD4 receptor.

5. A method for treating HIV infection comprising administering to a subject a composition comprising GBV-C NS5A peptide or polypeptide, wherein said NS5A peptide or polypeptide inhibits HIV replication and thereby treats HIV infection.

6. The method of claim 5, wherein the NS5A polypeptide comprises residues 152-237 of GBV-C NS5A.

* * * * *

UNITED STATES PATENT AND TRADEMARK OFFICE
CERTIFICATE OF CORRECTION

PATENT NO. : 7,951,531 B2
APPLICATION NO. : 11/345662
DATED : May 31, 2011
INVENTOR(S) : Jack T. Stapleton et al.

Page 1 of 1

It is certified that error appears in the above-identified patent and that said Letters Patent is hereby corrected as shown below:

In column 1, lines 10-13, delete
"The U.S. Government own rights in this invention pursuant to grant number AI58740 from NIH and merit grants awarded to Jack Stapleton and Jinhua Xiang from the Veterans Administration." and insert
--This invention was made with government support under grant number AI58740 awarded by the National Institutes of Health and merit grants awarded to Jack Stapleton and Jinhua Xiang from the Veterans Administration. The government has certain rights in the invention--.

Signed and Sealed this
Twenty-seventh Day of September, 2011

David J. Kappos
*Director of the United States Patent and Trademark Office*